(12) United States Patent
Vidyasagar et al.

(10) Patent No.: US 11,576,884 B2
(45) Date of Patent: Feb. 14, 2023

(54) AMINO ACID COMPOSITIONS AND USES THEREOF

(71) Applicants: University of Florida Research Foundation, Incorporated, Gainesville, FL (US); ENTRINSIC, INC., Norwood, MA (US)

(72) Inventors: Sadasivan Vidyasagar, Gainesville, FL (US); Reshu Gupta, Gainesville, FL (US); Liangjie Yin, Gainesville, FL (US); Astrid Grosche, Gainesville, FL (US); Paul Gerson Okunieff, Gainesville, FL (US); Stephen Gatto, Norwood, MA (US); Daniel Dennison, Tallahassee, FL (US)

(73) Assignees: UNIVERSITY OF FLORIDA RESEARCH FOUNDATION, INC., Gainesville, FL (US); ENTRINSIC, LLC, Norwood, MA (US)

( * ) Notice: Subject to any disclaimer, the term of this patent is extended or adjusted under 35 U.S.C. 154(b) by 764 days.

(21) Appl. No.: 16/339,461

(22) PCT Filed: Oct. 4, 2017

(86) PCT No.: PCT/US2017/055167
§ 371 (c)(1),
(2) Date: Apr. 4, 2019

(87) PCT Pub. No.: WO2018/067717
PCT Pub. Date: Apr. 12, 2018

(65) Prior Publication Data
US 2021/0283081 A1    Sep. 16, 2021

Related U.S. Application Data

(60) Provisional application No. 62/421,443, filed on Nov. 14, 2016, provisional application No. 62/403,965, filed on Oct. 4, 2016.

(51) Int. Cl.
*A61K 31/198* (2006.01)
*A61K 31/405* (2006.01)

(52) U.S. Cl.
CPC .......... *A61K 31/198* (2013.01); *A61K 31/405* (2013.01)

(58) Field of Classification Search
CPC ..... A61K 31/198; A61K 31/405; A61P 11/06; A61P 11/00
See application file for complete search history.

(56) References Cited

U.S. PATENT DOCUMENTS

| | | |
|---|---|---|
| 5,522,378 A | 6/1996 | Ritson et al. |
| 5,775,320 A | 7/1998 | Patton et al. |
| 5,934,272 A | 8/1999 | Lloyd et al. |
| 5,960,792 A | 10/1999 | Lloyd et al. |
| 5,976,574 A | 11/1999 | Gordon |
| 5,985,248 A | 11/1999 | Gordon et al. |
| 6,001,336 A | 12/1999 | Gordon |
| 7,557,087 B2 | 7/2009 | Rothbard et al. |
| 8,691,213 B2 * | 4/2014 | Langford ............... A23L 33/21 424/93.4 |
| 8,993,522 B2 | 3/2015 | Vidyasagar et al. |
| 10,322,109 B2 | 6/2019 | Vidyasagar et al. |
| 10,350,185 B2 * | 7/2019 | Vidyasagar ............ A61P 29/00 |
| 10,758,507 B2 * | 9/2020 | Vidyasagar .......... A61K 31/198 |
| 2002/0042086 A1 | 4/2002 | Schwarz et al. |
| 2007/0010459 A1 | 1/2007 | Liu et al. |
| 2008/0027007 A1 | 1/2008 | Benner et al. |
| 2011/0183040 A1 * | 7/2011 | Ermolin ................ A61P 37/04 426/72 |

(Continued)

FOREIGN PATENT DOCUMENTS

| | | |
|---|---|---|
| EP | 0810829 B1 | 4/2000 |
| JP | 2011105640 | 6/2011 |

(Continued)

OTHER PUBLICATIONS

Fogarty et al., "Amino acids and asthma: a case-control study", 2004, European Respiratory Journal, 23(4), pp. 565-568. (Year: 2004).*
Matsuda et al., "Development of atopic dermatitis-like skin lesion with IgE hyperproduction in NC/Nga mice," International Immunology, vol. 9, No. 3, pp. 461-466, abstract (1997).
International Search Report to corresponding International Application No. PCT/US17/55167 dated Feb. 13, 2018 (7 pages).
International Written Opinion to corresponding International Application No. PCT/US 17/55167 dated Feb. 13, 2018 (13 pages).
International Preliminary Report on Patentability to corresponding International Application No. PCT/US2017/055167 dated Feb. 13, 2018 (14 pages).

(Continued)

*Primary Examiner* — My-Chau T. Tran
(74) *Attorney, Agent, or Firm* — Greenberg Traurig, LLP

(57) ABSTRACT

The present disclosure provides compositions and methods for promoting stem cell and/or progenitor cell proliferation and/or differentiation. The provided compositions may be useful in treating a disease or condition that is related to mucosal barrier function, e.g., wound healing, treating skin conditions (e.g., atopic dermatitis, psoriasis, bed sores, or condition related to the aging of skin), treating a lung disorders (e.g., asthma), a condition related to improving mucosal barrier function, and/or treating injury to GI mucosa in a subject in need thereof. The present disclosure also provides methods for promoting the proliferation and/or differentiation of stem cells and/or the progenitor cells in a subject in need of such treatment by administering a composition. The ability to stimulate the proliferation and/or differentiation of stem cells and/or the progenitor cells in vivo, ex vivo and/or in vitro provides tremendous benefit. The present disclosure can be used to increase stem cell populations in in vivo, ex vivo and/or in vitro. Stem cell transplantation provides treatments and/or cures of many disease states, degeneration and/or injury.

21 Claims, 25 Drawing Sheets

(56) References Cited

U.S. PATENT DOCUMENTS

| | | |
|---|---|---|
| 2012/0077748 A1 | 3/2012 | Vidyasagar et al. |
| 2013/0018080 A1 | 1/2013 | Conti et al. |
| 2013/0071439 A1 | 3/2013 | Losick et al. |
| 2015/0196534 A1 | 7/2015 | Vidyasagar et al. |
| 2016/0106715 A1 | 4/2016 | Plumb |
| 2016/0271049 A1 | 9/2016 | Schulze zur Wiesche et al. |
| 2019/0046504 A1 | 2/2019 | Vidyasagar et al. |
| 2019/0307724 A1 | 10/2019 | Vidyasagar et al. |

FOREIGN PATENT DOCUMENTS

| | | |
|---|---|---|
| WO | 96/32149 A1 | 10/1996 |
| WO | 97/41833 A1 | 11/1997 |
| WO | 98/29096 A1 | 7/1998 |
| WO | 01/78532 A1 | 10/2001 |
| WO | 2009/020394 A1 | 2/2009 |
| WO | 2011/064297 A1 | 6/2011 |
| WO | 2013/093947 A1 | 6/2013 |
| WO | 2013093947 A1 | 6/2013 |
| WO | 2013/119917 A1 | 8/2013 |
| WO | 2014/164736 A1 | 10/2014 |
| WO | 2016/085735 A1 | 6/2016 |

OTHER PUBLICATIONS

Naylor, J.M., et al., "Effect of Glutamine or Glycine Containing Oral Electrolyte Solutions on Mucosal Morphology, Clinical and Biochemical Findings, in Calves with Viral Induced Diarrhea", Can J Vet Res 1997; 61: 43-48.

Cho, Chung-Hyun, et al., "Designed angiopoietin-1 variant, COMP-Ang1, protects against radiation-induced endothelial cell apoptosis", PNAS, Apr. 13, 2004, vol. 101, No. 15, pp. 5553-5558.

Epperly, M., et al., "Prevention of late effects of irradiation lung damage by manganese superoxide dismustase gene therapy", Gene Theraphy (1998) 5, pp. 196-208.

Wheeler, M.D., et al., "Dietary glycine blunts lung inflammatory cell influx following acute endotoxin", American Journal Physiol. Lung Cell Mol. Physiol, 279: L390-L398, 2000.

Notice of Opposition to a European Patent, European Patent No. 2968241 (Application No. 14779732.8), filed Jul. 29, 2019, 20 pages.

Yin et al., "An Amino Acid Mixture Mitigates Radialion-Induced Gastrointestinal Toxicity," Health Physics, 106(6), pp. 734-744 (2014).

Examination Report to corresponding Australian Application No. 2017338887 dated Jul. 31, 2020, 9 pages (2020).

Zhang, Kai, et al., "Protection against acute radiation-induced lung injury: A novel role for the anti-angiogenic agent Endostar", Molecular Medicine Reports 6: 309-315, (2012).

Detrick, Lawrence E., et al., "Influence of X-Ray Irradiation on Glucose Transport in the Rat Intestine", Radiation Research Society, www.jstor.org, Oct. 6, 1954, 7 pgs.

Nalin, D.R., et al., "Effect of glycine and glucose on sodium and water absorption in patients with cholera", Gut, 1970, 11, pp. 768-772.

* cited by examiner

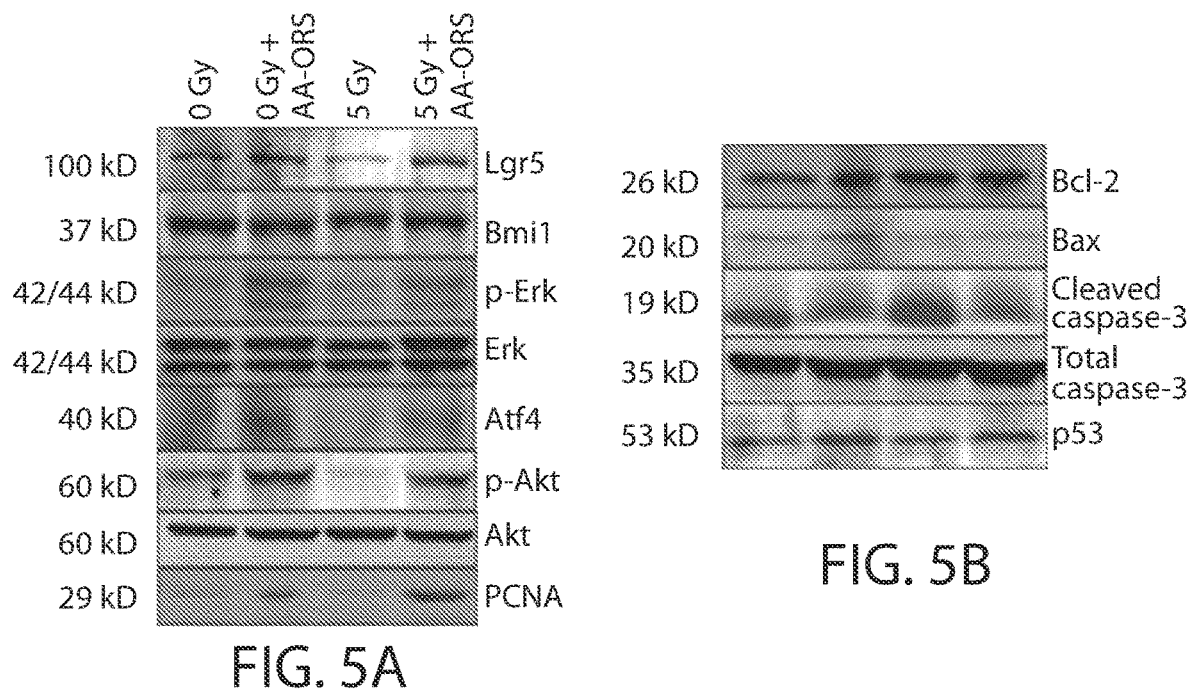
FIG. 5A
FIG. 5B
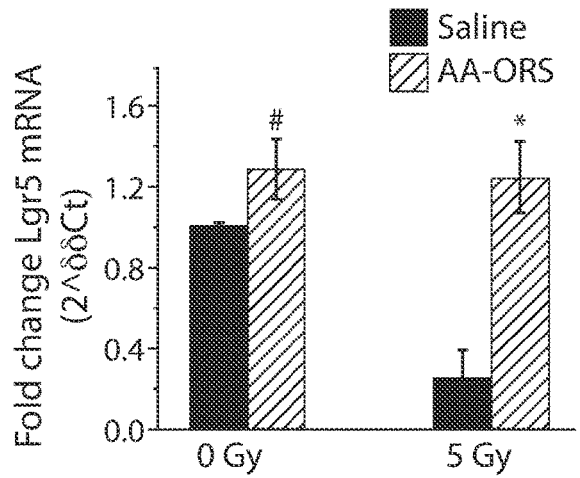
FIG. 5C
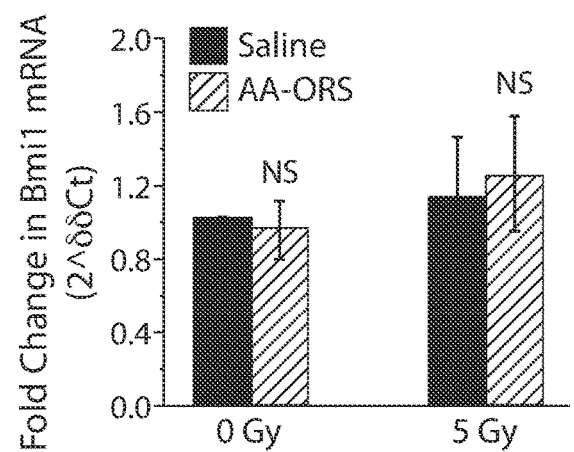
FIG. 5D

| Test | LAR (Control)* | LAR (Treated) | AHR (Control)+ | AHR (Treated) |
|---|---|---|---|---|
| 1h pre Aerosol | 111.8±11.6 | 62.8±6.2 | 0.27 | 0.82 |
| 30 min pre Aerosol | 110.5±8.3 | 50.0±5.9 | 0.42 | 0.92 |
| 30 post Aerosol | 113.0±8.8 | 44.5±6.2 | 0.53 | 1.02 |
| 2h post Aerosol | 107.5±9.3 | 32.2±3.4 | 0.56 | 0.97 |
|  |  |  |  |  |
| 2h post Oral | 112.7±8.8 | 38.8±11.9 | 0.52 | 0.83 |
| 30 min post Oral | 100.3±9.8 | 66.7±8.2 | 0.52 | 0.89 |

AMINO ACID COMPOSITIONS AND USES THEREOF

RELATED APPLICATIONS

This application claims priority to International Application No. PCT/US2017/055167 filed Oct. 4, 2017, entitled "AMINO ACID COMPOSITIONS AND USES THEREOF, which claims priority to U.S. Provisional Application Ser. No. 62/403,965, filed on Oct. 4, 2016, entitled "MATERIALS AND METHODS FOR PROMOTING STEM CELL AND/OR PROGENITOR CELL PROLIFERATION AND/OR DEVELOPMENT", and U.S. Provisional Application Ser. No. 62/421,443 filed Nov. 14, 2016, entitled "AMINO ACID COMPOSITIONS AND USES THEREOF", the entire content of which is hereby incorporated by reference in its entirety.

BACKGROUND OF THE INVENTION

Human intestinal epithelial cells are generated from a fixed population of stem cells functionally situated in the lower portion of the intestinal crypts, including fast cycling crypt base columnar cells (CBCs) and more quiescent "+4" cells above Paneth cells in mice.[14-16] These stem cells give rise to absorptive enterocytes, mucus cells, Paneth cells, and enteroendocrine The differentiation of each cell type occurs when cells either move upwards into the villus (absorptive, mucus, and endocrine cells) or concentrate downwards at the bottom of the crypt (Paneth cells). The multiple mechanisms responsible for these complex events are not fully understood.

Radiation and/or chemotherapy can cause severe damage to the lining of the gastrointestinal (GI) tract. Moderate to high doses of radiation and/or chemotherapy result in the destruction of cells with clonogenic potential, which are essential for the continuous replacement of cells that are shed from the top of the villi during the normal proliferation, maturation, and differentiation process.

Toxic effects of radiation exposure and/or chemotherapy on the gastrointestinal system cause symptoms, such as nausea, vomiting, diarrhea, electrolyte imbalance and dehydration, and adversely affect a patient's health in the course of cancer therapy. Radiation exposure affects intestinal epithelial cells undergoing rapid mitosis in submucosal crypts. In therapeutic radiation exposure, gastrointestinal toxicity quite often becomes a dose-limiting factor for treatment and can affect a patient's quality of life. Therapeutic compounds and supportive care are often used to minimize toxicity, but these approaches are not fully effective.

There has been a growing interest in developing mitigation agents for short-term and long-term GI toxicity in cancer patients and victims of radiation disasters.[5,15,34,37] There are only two FDA approved agents; Neupogen® and Pegfilgrastim (Granulocyte-colony stimulating factor) are the two FDA-approved medical countermeasures that are currently available to treat radiation syndrome. Both work to increase survival in patients exposed to myelosuppressive doses of radiation. However, there are no agents that specifically address gastrointestinal toxicity. Treatment of GI toxicity is mostly symptomatic, with antidiarrheals used to prevent fluid loss, smectite to absorb bile salts, opioids to relieve stomach or rectal pain, steroids to relieve inflammation, and in extreme cases parenteral feeding to correct malabsorption of nutrients and electrolytes. Other agents that could potentially be used for mitigating GI toxicity are; 1) statin and/or angiotensin-converting enzyme, these agents have been found effective when used during radical pelvic radiotherapy works by its anti-inflammatory, antifibrotic, and antithrombotic actions; 2) antioxidants such as vitamin E and/or selenium; 3) teduglutide, a glucagon-like peptide-2 analogue that must be given prior to radiation; 4) Sucralfate, a highly sulphated polyanionic disaccharide helps in epithelial healing, but has not been shown to be useful in radiation-induced GI toxicity; 5) nitroxides such as hydroxylamines (tempol), works by its antioxidant properties; 6) dithiolthione (Oltipraz), works by increasing sulfhydryl in cells; 7) isoflavone (genistein), a tyrosine kinase inhibitor and antioxidant; 8) Cox-inhibitors (celecoxib, aspirin), work by increasing Cox2 activity and prostaglandin synthesis; and 8) probiotics, a preparation containing viable and well defined microorganisms in large numbers to alter hosts microflora and may have some effect on radiation-induced GI toxicity,[5] (Stacey, R. & Green, J. T. Radiation-induced small bowel disease: latest developments and clinical guidance. *Ther. Adv. Chronic Disease*, 5, 15-29, doi:10.1177/2040622313510730 (2014).

The crypt to the villus migration takes between 5-7 days. Therefore, gastrointestinal toxicity manifests itself in the first week following radiation exposure and/or chemotherapy and is the most significant dose-limiting factor in cancer therapy. Even at low doses, a continuous loss of the villous and brush border of the small bowel is observed within days after irradiation and/or chemotherapy. While crypt cells can rapidly repopulate the region following mild to moderate doses of irradiation and/or chemotherapy, they became lost at a logarithmic rate after irradiation and/or chemotherapy at high doses.

Irradiation and/or chemotherapy is particularly destructive to the villous epithelium, where nutrient and electrolyte absorption occurs. The villous epithelium undergoes a continuous cellular loss and regeneration process, in which a constant supply of immature enterocytes, originating from progenitor cells located within the lower poles of the crypts of Lieberkuhn, migrate out of the proliferative compartment at the base of the crypt to the top of the villous. During their short lifespan, these enterocytes gradually mature along the crypt-villous axis into villous cells. Radiation and/or chemotherapy therapy destroys not only the existing villous cells, but also stem cell and/or progenitor cells from which new villous cells form, and thus, can deplete almost the entire villous epithelium even at moderate doses.

Mature and differentiated villus cells are involved in fluid absorption secondary to sodium, chloride, and nutrient absorption, whereas the less differentiated, immature epithelial cells located in the crypt are predominantly involved in chloride (Cl⁻) secretion and fluid loss. The lack of absorptive villus epithelial cells leads to a malabsorptive state in which unabsorbed nutrients, electrolytes, and water are dumped into the distal segments of the GI tract, resulting in nausea, vomiting, and diarrhea.

Stem cell-mediated repopulation of villus cells through proliferation of in situ cells and/or potential migration into tissues via the circulation of progenitor cells from distant sites is responsible for recovery from acute irradiation and/or chemotherapy effects at the tissue level.[11-13] Therefore, the loss of crypt stem cells or villus endothelial cells is thought to be responsible or radiation and/or chemotherapy-induced intestinal damage.

Damage to the GI tract not only results in the malabsorption and loss of nutrients, minerals, and fluids, but also disrupts intestinal barrier function. The leaky gut allows for easy entry of pathogens and other antigenic substances from food into the systemic compartment, across the mucosal barrier, causing inflammation, bacteremia, and endotoxemia. For instance, acute radiation enteritis, diarrhea, and abdominal pain can develop within days post irradiation even at doses as low as 5-12 Gy (a conventional fractionated course of radiation uses 1.8-2 Gy per fraction), although GI toxicity usually occurs at higher doses. Chronic radiation enteritis can develop between 18 months and 6 years after radiotherapy, while it may develop even 15 years later.[27-29]

Treatment options for radiation and/or chemotherapy enteritis are limited. Conventional treatment regimens include the administration of antidiarrheals to prevent fluid loss, smectite as an adsorbant of bile salts, opioids to relieve stomach or rectal pain, and steroids to relieve inflammation.

A common approach in the therapy of radiation and/or chemotherapy enteritis is using total parenteral nutrition (TPN) to provide intestinal rest; however, whether parenteral nutrition satisfies the nutritional needs of patients, or actually has therapeutic effects on radiation and/or chemotherapy-induced enteritis remains to be determined. Although TPN may correct nutrition imbalance in certain patients, severe radiation and/or chemotherapy induced enteritis may still develop.[37] TPN also causes intestinal atrophy, usually within 48 hours of administration. TPN also weakens mechanical and immunological barriers.[38]

The formulation used in U.S. Pat. No. 8,993,522 works by correcting rehydration via amino acid-coupled sodium transport, decreasing anion secretion from the crypt by choosing a set of amino acids with anti-secretory property, and by tightening the mucosa by using the amino acids that were shown to tighten the mucosal barrier.

A need exists for improved compositions for the treatment of irradiation and/or chemotherapy-induced GI injury secondary to loss of proliferating stem and/or progenitor cells. There is also a need for compositions for treating a disease or conditions that is related to mucosal barrier function, e.g., wound healing, treating skin conditions (e.g., atopic dermatitis, psoriasis, bed sores, or condition related to the aging of skin), treating lung disorders (e.g., asthma), improving mucosal barrier function, and/or treating injury to GI mucosa in a subject in need thereof.

SUMMARY OF THE INVENTION

Described herein are compositions of amino acids for treating GI, lung, and skin disorders. In one aspect, the present disclosure provides compositions and methods for promoting cell survival, proliferation, migration, maturation, and/or cell differentiation. In certain embodiments, the disclosure provides compositions and methods for promoting stem cell and/or progenitor cell survival, proliferation, and/or development. The cell development may include, for example, migration, maturation, and/or differentiation. The disclosure also provides compositions and methods for treating a disease or conditions that is related to mucosal barrier function, e.g., wound healing, treating skin conditions (e.g., atopic dermatitis, psoriasis, bed sores, or condition related to the aging of skin), treating lung disorders (e.g., asthma), improving mucosal barrier function, and/or treating injury to GI mucosa in a subject in need thereof.

This cell proliferation and/or development can be used to improve proliferation and function of stem cells and progenitor cells located in various organ systems and places in the body. The stem and/or the progenitor cells may be, for example, in the small intestine or from other tissues, including, but not limited to, skin, bone marrow, lungs, neurons, pancreas, muscle, skeletal tissues, vascular endothelial cells, and corneal epithelial cells. The stem and/or the progenitor cells may be adult stem cells, embryonic stem cells, or cancer stem cells. In one embodiment, the composition useful in treating the conditions described herein comprises one or more free amino acids selected from the group consisting of the group consisting of threonine, valine, tyrosine, tryptophan, aspartic acid, and serine; and, optionally, an acceptable carrier.

In certain embodiments, the composition of the present disclosure does not include one or more amino acids selected from the group consisting of lysine, glycine, isoleucine, and asparagine. In certain embodiments, the composition does not include lysine, glycine, aspartic acid, isoleucine, and asparagine. In another specific embodiment, the composition does not include, or only includes negligible amounts of, serine, lysine, glycine, aspartic acid, isoleucine, and asparagine. certain embodiments, the composition does not include glutamine and/or methionine; and any di-, oligo-, or polypeptides or proteins that can be hydrolyzed into glutamine and/or methionine. In certain embodiments, the composition does not include methionine.

Or, in certain embodiments, even if these amino acids are present in the composition, they are not present in an amount that would inhibit stem cell and/or progenitor cell survival, proliferation, and/or development. In some embodiments, the composition does not include serine. In some embodiments, the composition does not include cysteine. In certain embodiments, even if these amino acids are present in the composition, they are not present in an amount that would affect the treatment of a disease or conditions that is related to mucosal barrier function, e.g., wound healing, treating skin conditions (e.g., atopic dermatitis, psoriasis, bed sores, or condition related to the aging of skin), treating lung disorders (e.g., asthma), improving mucosal barrier function, and/or treating injury to GI mucosa.

These amino acids, if present in the composition, may be present in, for example, the following concentrations: threonine at about 0.4 to about 1.5, about 0.7 to about 1.3, or about 0.9 to about 1.1 grams/liter; valine at about 0.7 to about 1.7, about 0.9 to about 1.5, or about 1.1 to about 1.3 grams/liter; serine at about 0.6 to about 1.6, about 0.8 to about 1.4, about 1.0 to about 1.2 grams/liter; tyrosine at about 0.05 to about 0.4, or about 0.1 to about 0.3 grams/liter; and tryptophan at about 1.1 to about 2.1, about 1.3 to about 1.9, or about 1.5 to about 1.7 grams/liter. In certain embodiments, the concentration is grams amino acid per liter of solution. In certain embodiments, the solution comprises water. In a certain embodiment, the therapeutic composition comprises threonine (approximately 1.0 grams/liter), valine (approximately 1.2 grams/liter), serine (approximately 1.1 grams/liter), tyrosine (approximately 0.2 grams/liter), and tryptophan (approximately 1.6 grams/liter). In one embodiment, the composition does not include serine. In some embodiments, the composition does not include methionine. In some embodiments, the composition does not include cysteine.

In certain embodiments, the total osmolarity of the composition is from about 100 mosm to about 280 mosm, or about 150 to about 280 mosm.

The composition may have a pH from, for example, about 2.5 to about 8.5. In certain embodiments, the composition has a pH from about 2.5 to about 6.5, about 3.0 to about 6.0, about 3.5 to about 5.5, about 3.9 to about 5.0, or about 4.2 to about 4.6. In other embodiments, the pH is about 6.5 to about 8.5, about 7.0 to about 8.0, or about 7.2 to about 7.8.

In certain embodiments, the composition is administered as a solution or drink, a powder, a pill, a gel, cream, ointment, as part of a matrix, or on a bandage. In certain embodiments, the composition is administered as part of a matrix delivery system.

The composition may be administered systemically or locally. In certain embodiments, the composition is used to promote cellular survival, proliferation, and/or development ex vivo or in vitro. In certain embodiments, the composition is used for treating a disease or conditions that is related to mucosal barrier function, e.g., wound healing, treating skin conditions (e.g., atopic dermatitis, psoriasis, bed sores, or condition related to the aging of skin), treating lung disorders (e.g., asthma), improving mucosal barrier function, and/or treating injury to GI mucosa.

In certain embodiments, the composition also comprises additives (e.g., nutrients, electrolytes, vitamins, minerals, etc.).

Without wishing to be bound by any particular theory, the compositions and methods are thought to prevent DNA damage and are therefore useful in preventing damage to DNA and/or repairing damaged DNA. In another embodiment, the compositions and methods promote the survival, proliferation, and development of stem cells by preventing damage to DNA and/or repairing damaged DNA.

In another aspect, the present disclosure provides methods of treating a lung disorder in a subject in need thereof. In another aspect, the present disclosure provides compositions and methods for improving lung healing, decreasing pneumonitis, decreasing airway resistance, and/or improving lung function in a subject in need thereof. In certain embodiments, the lung condition is a lung injury, pneumonitis, or asthma. In certain embodiments, the lung condition is associated with increased airway resistance. In certain embodiments, the lung condition is associated with decreased barrier function. In certain embodiments, the composition is administered systemically or administered via inhalation. In certain embodiments, the compositions and methods are useful for improving lung healing, decreasing pneumonitis, decreasing airway resistance, and improving lung function, for example, following radiation exposure and/or chemotherapy.

In another embodiment, the compositions and methods of the present disclosure to treat bone marrow suppression that is caused by, for example, a drug, virus, bacteria, toxins, chemicals, or vitamin deficiency. For example, in certain embodiments the compositions and methods are used to treat a patient with a low platelet count (thrombocytopenia) caused by, for example, Dengue virus infection.

In another aspect, the present disclosure provides methods of treating a GI disorder or GI tract disorder (e.g., radiation injury, ischemic colitis, infection, trauma), or any other condition related to mucosal barrier function and/or integrity. In certain embodiments, provided are methods of treating a disease or condition that is related to mucosal barrier function. In certain embodiments, the disease or condition that is related to mucosal barrier function is dysfunction of a mucosal barrier. In certain embodiments, the treatment of a disease or condition that is related to mucosal barrier function is wound healing. treating injury to GI mucosa in a subject in need thereof. In certain embodiments, provided are methods of treating injury to GI mucosa in a subject in need thereof. In certain embodiments, the GI mucosa are small intestine mucosa. In certain embodiments, the composition is used for treatment after surgery (e.g., bowel surgery). In certain embodiments, the composition is used to treat any disease or conditions that would lead to ischemic bowel, including, for example, hypotension, shock, thrombosis, bowel obstruction, etc.

One composition useful for the treatment of radiation enteritis is an amino acid-based oral rehydration solution (AA-ORS) described in U.S. Pat. No. 8,993,522, which is incorporated herein by reference. AA-ORS is a composition for improving small intestine health, wherein the composition is formulated for enteral administration and comprises threonine, valine, tryptophan, serine, and tyrosine, as free amino acids; and water; wherein the composition does not include free amino acid glutamine or a glutamine-containing dipeptide, or, if free amino acid glutamine and/or a glutamine-containing dipeptide is present, the total concentration of the free amino acid glutamine and the glutamine-containing dipeptide is less than 50 mg/l; wherein the composition does not include glucose or, if glucose is present, the concentration of glucose is less than 1 g/l; and wherein the composition does not include free amino acid methionine or a methionine-containing peptide, optionally lysine, glycine, aspartic acid, and/or isoleucine, and optionally electrolytes, vitamins, minerals, and/or flavoring agents.

In another aspect, the present disclosure provides methods of treating a skin condition (e.g., atopic dermatitis, psoriasis, or condition related to the aging of skin) in a subject in need thereof, the method comprising administering to the subject a composition described herein. In certain embodiments, the skin condition is atopic dermatitis, psoriasis, the aging of skin, related to the aging of skin, or bed sores. In certain embodiments, the composition and methods described herein are useful for beauty applications where, for example, rejuvenation of the various layers of the skin and/or the underlying tissues is desired.

Definitions

The terms "improving skin condition" or "treating a skin condition" include prophylactically preventing or therapeutically treating a skin condition, and may involve one or more of the following benefits: thickening of skin, preventing loss of skin elasticity, and a reduction in lines or winkles.

The term "epidermis" or "epidermal," as used herein, refers to the outermost layer of the skin.

The term "topical application," as used herein, means to apply or spread the compositions of the present invention onto the surface of the epidermis tissue.

The term "dermatologically-acceptable," as used herein, means that the compositions or components thereof so described are suitable for use in contact with mammalian epidermal tissue without undue toxicity, incompatibility, instability, allergic response, and the like.

The term "therapeutically effective amount," as used herein, refers to an amount of a compound or composition sufficient to induce a positive benefit, preferably a positive skin appearance and/or feel. In accordance with the present disclosure, the therapeutically effective amount is an amount of amino acids, either alone or in combination with other agents, that regulates and/or improves the skin.

The term "amelioration" or any grammatical variation thereof (e.g., ameliorate, ameliorating, and amelioration etc.), as used herein, includes, but is not limited to, delaying the onset, or reducing the severity of a disease or condition. Amelioration, as used herein, does not require the complete absence of symptoms.

The terms "effective amount" or "significant amount" as used herein, refers to an amount that is capable of treating or ameliorating a disease or condition or otherwise capable of producing an intended therapeutic effect.

The term "health functional food" refers to a food prepared or processed into tablet, capsule, powder, granule, liquid, pill, or any other form using raw materials or ingredients with useful functions for the human body.

The term "functional" means a useful effect for human health, such as structural or functional regulation of nutrients, the immune system, inflammation, fluid balance, physiological action, or the like.

The term "carrier" refers to a diluent, adjuvant, excipient, or vehicle with which the compound is administered. Examples of suitable pharmaceutical carriers are described in "Remington's Pharmaceutical Sciences" by E. W. Martin.

The term "treatment" or any grammatical variation thereof (e.g., treat, treating, and treatment etc.), as used herein, includes but is not limited to, alleviating a symptom of a disease or condition; and/or reducing, suppressing, inhibiting, lessening, or affecting the progression, severity, and/or scope of a disease or condition.

The term "consisting essentially of," as used herein, limits the scope of the ingredients and steps to the specified materials or steps and those that do not materially affect the basic and novel characteristic(s) of the present invention, i.e., compositions and methods for promoting stem cell development.

BRIEF DESCRIPTION OF THE DRAWINGS

FIG. 1A shows semi-log survival curve showing the effect of AA-ORS on crypt count. AA-ORS shifted the graph to the left. The crypt survival curve was modeled using a single-hit, multi-target cell survival model to assess the biological effect. The probability of survival of the mitotic cells in the crypt following radiation was calculated using the equation $[S=1-(1-e^{-D/D_0})^n]$. S represents the fraction of mitotic cells in the crypts that survived in each of the radiation doses, D represents radiation dose; $D_0$, a measure of the intrinsic radiation resistance of the crypt reproductive units. Dq values for saline treated mice and AA-ORS treated mice are represented by black arrow and gray arrow respectively. Dq is calculated from the formula $Dq=D_0$ ln n. Without constraining constant cell sensitivity, the N values were 10.4±0.2 and 5.3±0.1 (P<0.001), indicating a near doubling of progenitor units per circumference from a control. When a constant $D_0$ (4.8±0.1 Gy) was constrained, the difference remained significant at 8.8±0.4 to 6.1±0.3 (P<0.001). FIG. 1B shows the height of villus following treatment using saline and AA-ORS in irradiated mice. Significant increase in villus height with AA-ORS treated mice compared to mice receiving saline as treatment. Crypts per circumference were counted, and villus length was measured from 10 sections obtained from the ileum. Data are shown as the mean±S.E.M. for 6 mice per group. * indicates statistically significant difference (P<0.01). Normal saline (saline) was used as control and both saline and AA-ORS was given by gastric gavage.

FIGS. 5A-5G show protein levels and mRNA expression of Lgr5, BMI1, p-AKT, AKT, pERK, and ERK in villus epithelial cells from mice treated with normal saline and AA-ORS following 0 and 5 Gy irradiation.

FIG. 10 (tryptophan); FIG. 11 (serine); FIG. 12 (tyrosine)

FIG. 13 shows changes in Lgr5 protein levels with threonine treatment for a period of 6 days.

Effect on antigen-induced airway responses: Baseline dose response curves to aerosol carbachol are obtained 1-3 days before antigen challenge. On the challenge day baseline values of lung resistance (RL) are obtained and then the sheep are challenged with *Ascaris suum* antigen. Measurements of RL are obtained immediately after challenge, hourly from 1-6 h after challenge and on the half-hour from 6½-8 h after challenge. Measurements of RL are obtained 24 hours after challenge followed by the 24 hour post challenge dose response curve. In FIGS. 14-19, for the Figures showing airway responsiveness (PC400), BSL is baseline, and PASC is post-antigen challenge.

Figure 1A:
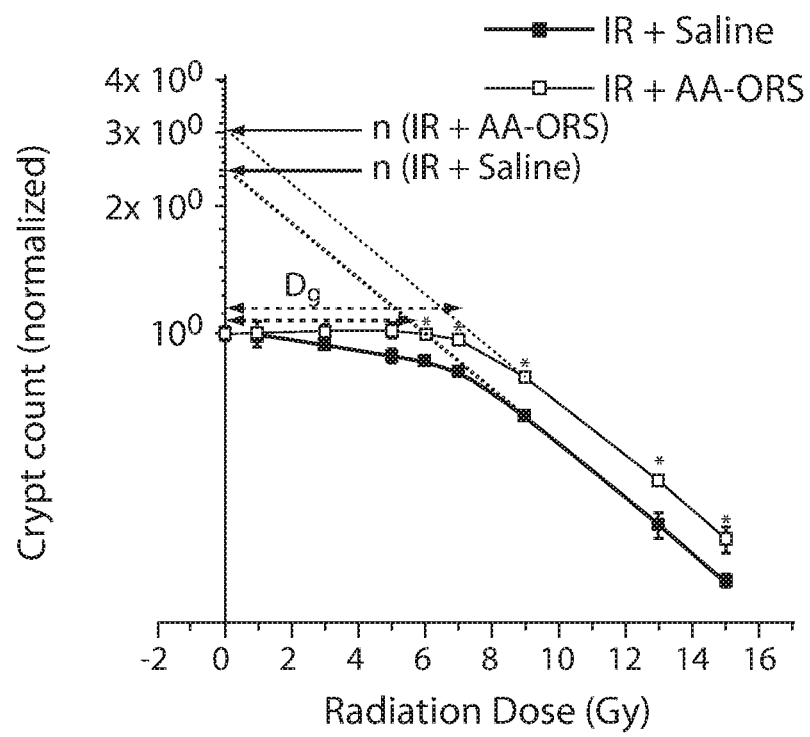
FIGS. 1A-1B show AA-ORS increased crypt count & villus length following irradiation. Normal saline (saline) was used as a control; saline and AA-ORS were given by gastric gavage. 6 mice per radiation group (0, 1, 3, 5, 6, 7, 9, 13 and 15 Gy) with and without treatment.

For the initial studies, sheep receive a nebulized compound (of an amino acid formulation consisting of tyrosine (1.2 mM), threonine (8 mM), valine (10 mM), serine (10 mM) and tryptophan (8 mM), wherein 4 mL of the amino acid formulation solution is administered) using the nebulization system described above) either 30 minutes before, 1 hour before, 30 minutes after, or 2 hours after antigen challenge. Measurements of RL are repeated after treatment. Thereafter, follow on studies will assess the effects after providing the compound orally. In the oral studies, sheep receive an amino acid formulation consisting of tyrosine (1.2 mM), aspartic acid (8 mM), threonine (8 mM), valine (10 mM), serine (10 mM), wherein 8 oz of the amino acid formulation solution is administered orally, and measurements of RL and airway responsiveness (PC 400) are taken as described above.

Figure 14:
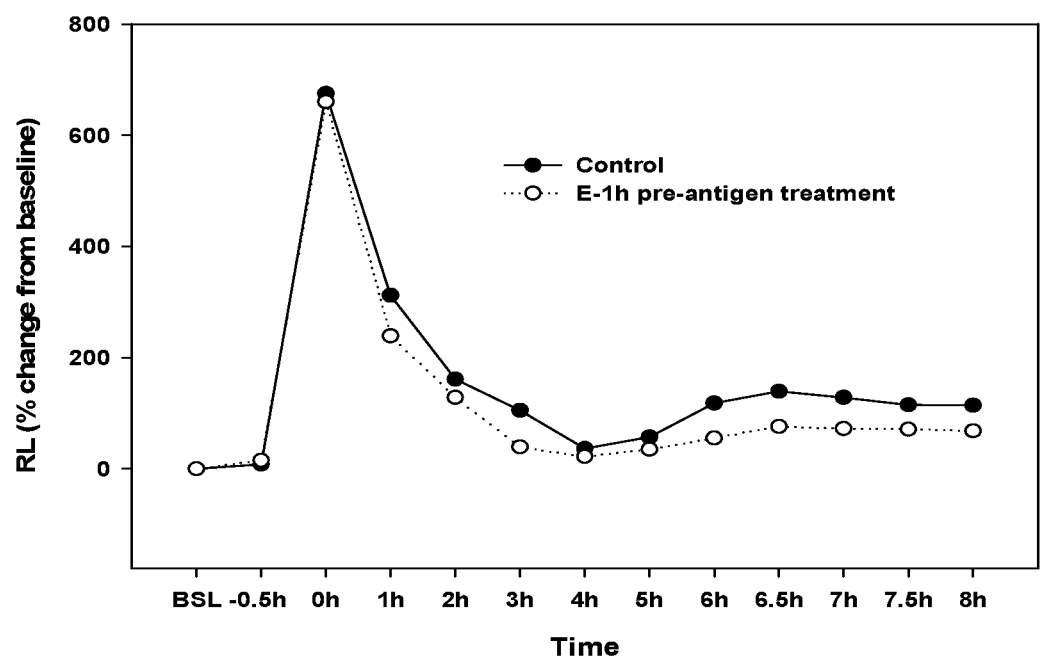
FIGS. 14 through 20 show results for an allergic asthma and anti-inflammatory airway function for treatment with an amino acid formulation in a sheep model. In the study, the animals will have demonstrated both early and late airway responses to inhalation challenge with *Ascaris suum* antigen. Venous blood samples (~3 ml) can be obtained from the external jugular vein for pharmacokinetic data. Measurement of Airway Mechanics: The unsedated sheep are restrained in a cart in the prone position with their heads immobilized. After topical anesthesia of the nasal passages with 2% lidocaine solution, a balloon catheter will be advanced through one nostril into the lower esophagus. The animals will be intubated with a cuffed endotracheal tube through the other nostril. (The cuff of the endotracheal tube will be inflated only for the measurement of airway mechanics and during aerosol challenges to prevent undue discomfort. This procedure has no effect on airway mechanics). Pleural pressure will be estimated with the esophageal balloon catheter (filled with one ml of air) which will be positioned 5-10 cm from the gastroesophageal junction. In this position the end expiratory pleural pressure ranges between −2 and −5 cm $H_2O$. Once the balloon is placed, it will be secured so that it remains in position for the duration of the experiment. Lateral pressure in the trachea will be measured with a sidehole catheter (inner dimension, 2.5 mm) advanced through and positioned distal to the tip of the endotracheal tube. Transpulmonary pressure, the difference between tracheal and pleural pressure, will be measured with a differential pressure transducer catheter system. For the measurement of pulmonary resistance (RL), the proximal end of the endotracheal tube will be connected to a pneumotachograph. The signals of flow and transpulmonary pressure will be recorded on an oscilloscope recorder which is linked to a computer for on-line calculation of RL from transpulmonary pressure, respiratory volume (obtained by digital integration) and flow. Analysis of 5-10 breaths will be used for the determination of RL in L×cm $H_2O/L/S$.
Figure 14:
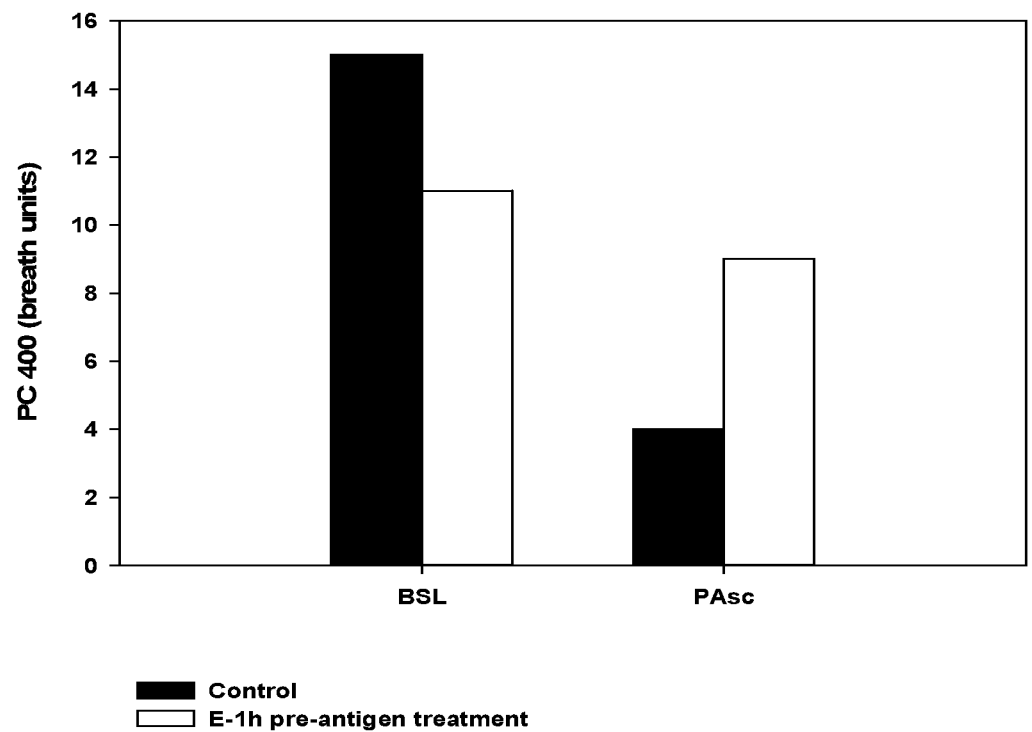

FIG. 14 shows the results for the lung resistance (RL) and PC 400 (breath units) for sheep having received the nebulized compound one hour before antigen challenge, compared with the control.

Figure 15:
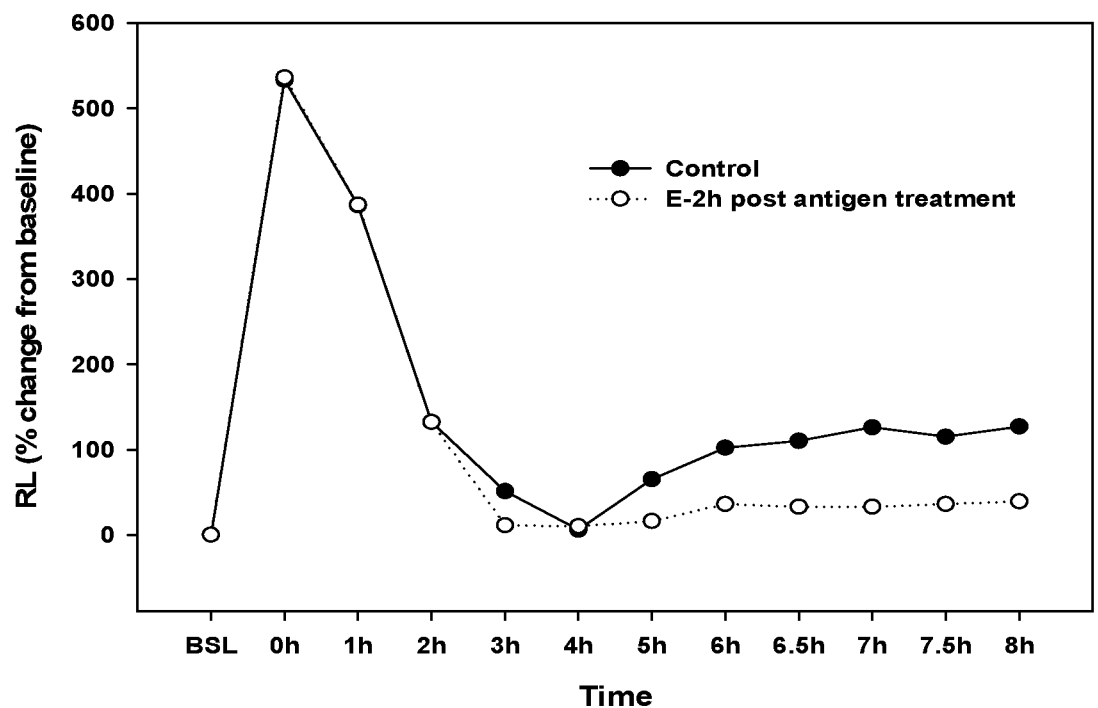
Figure 15:
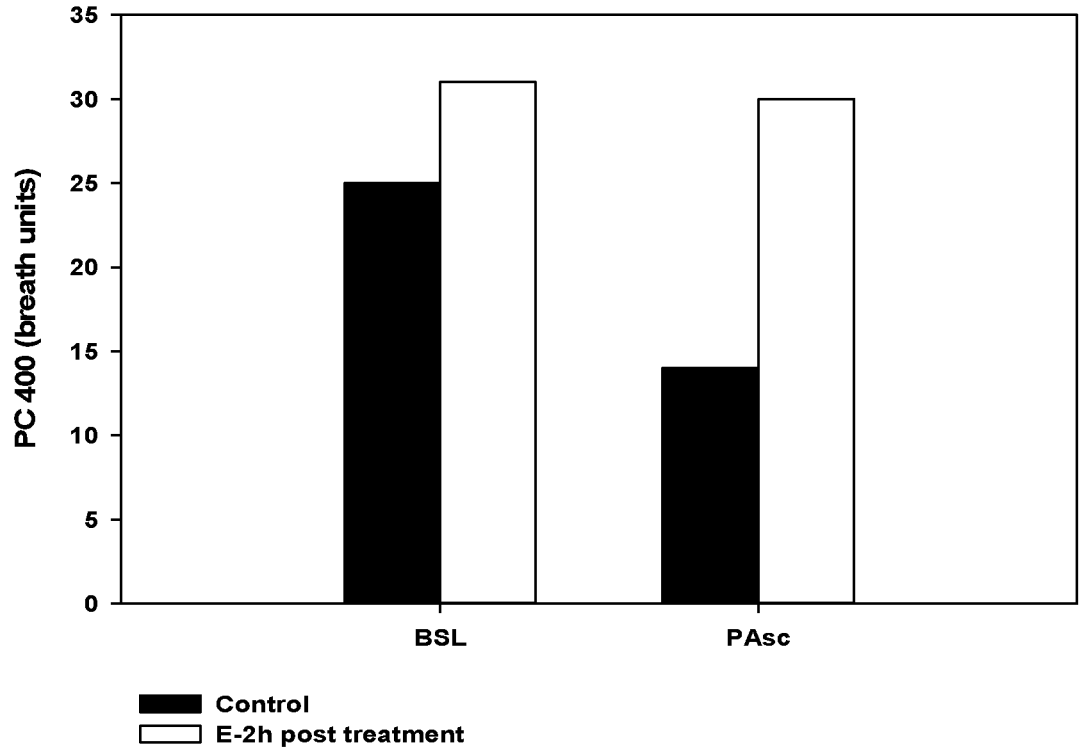

FIG. 15 shows the results for the lung resistance (RL) and PC 400 (breath units) for sheep treated with the nebulized compound two hours after antigen challenge, compared with the control.

Figure 16:
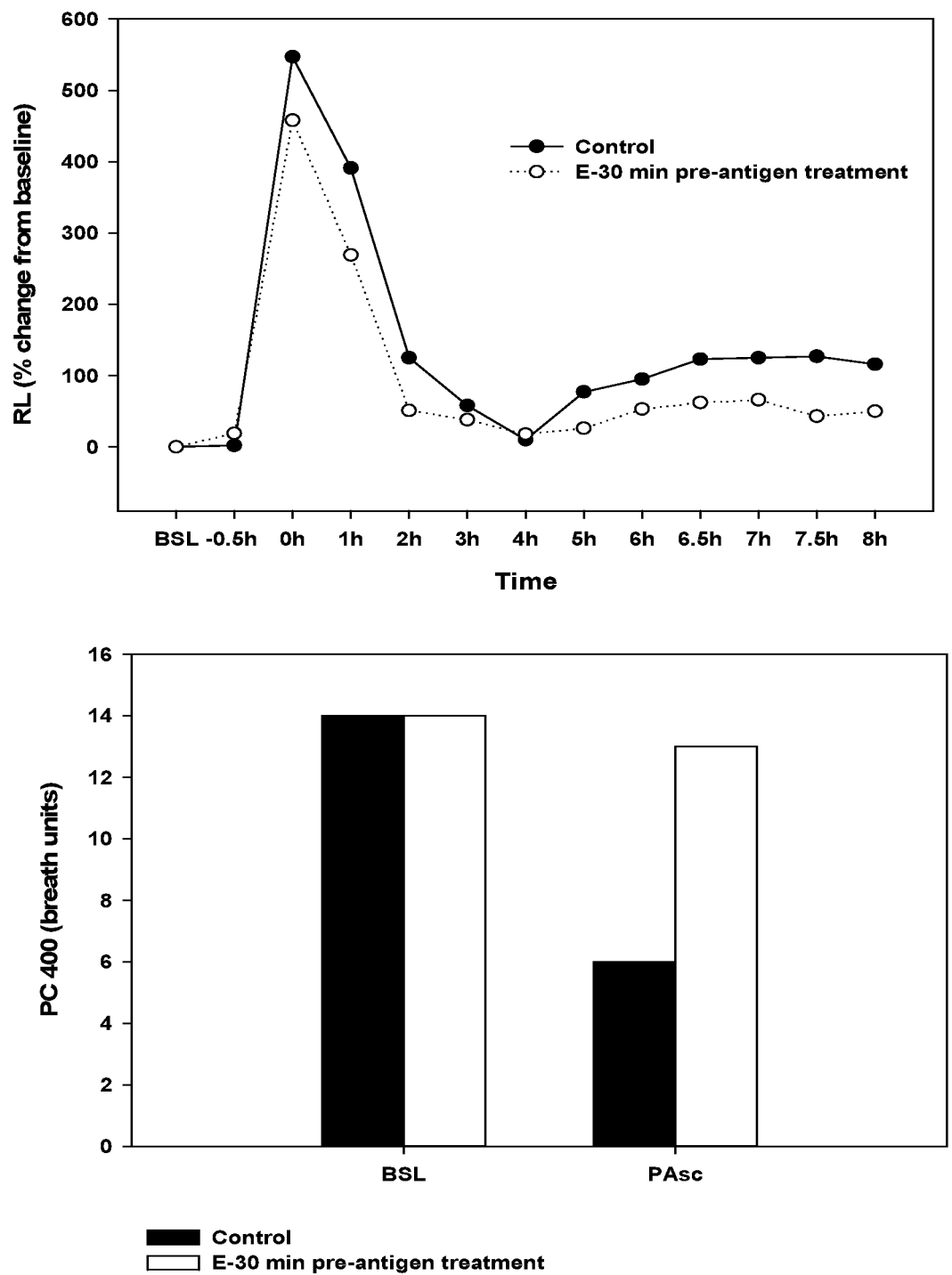

FIG. 16 shows the results for the lung resistance (RL) and PC 400 (breath units) for sheep treated with the nebulized compound 30 minutes before antigen challenge, compared with the control.

Figure 17:
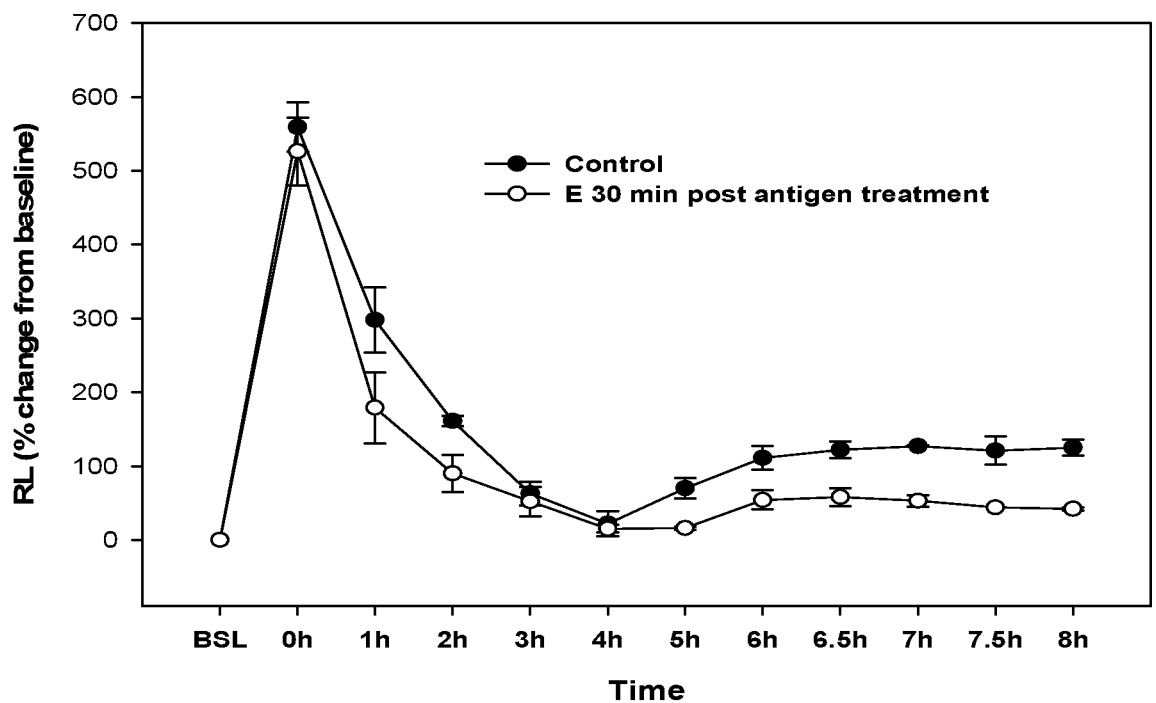
Figure 17:
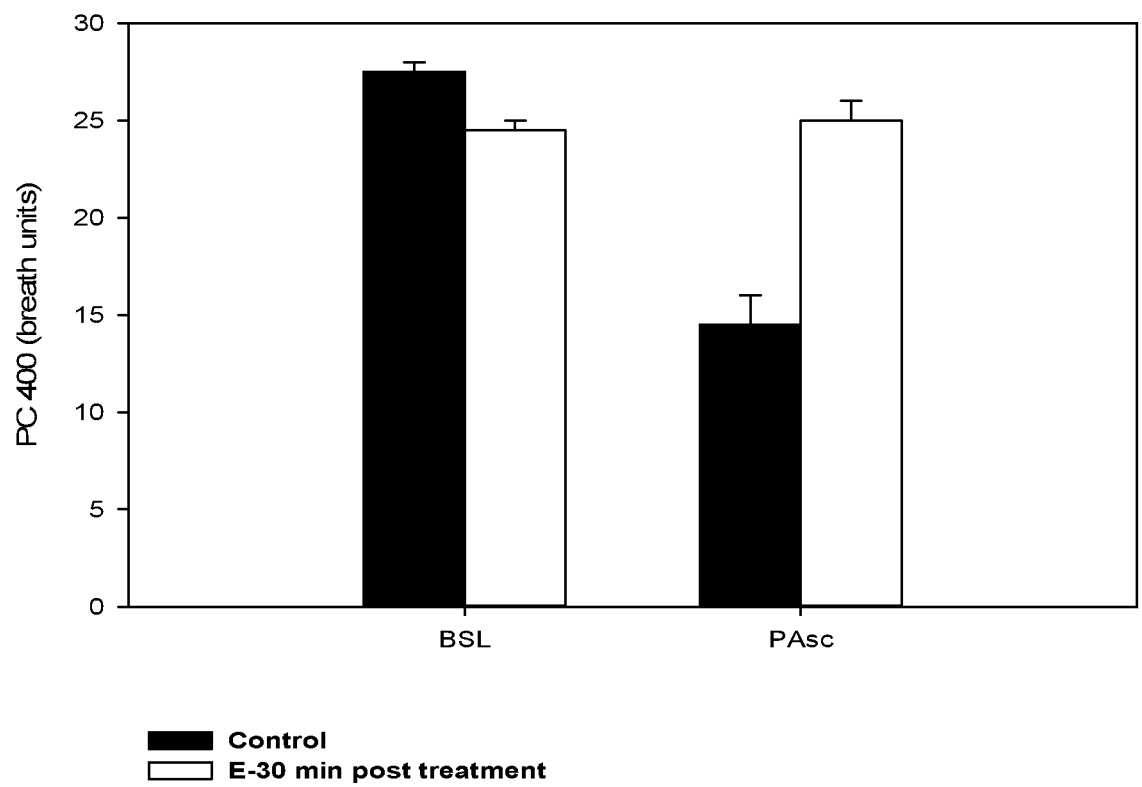

FIG. 17 shows the results for the lung resistance (RL) and PC 400 (breath units) for sheep having received the nebulized compound 30 minutes after antigen challenge, compared with the control.

Figure 18:
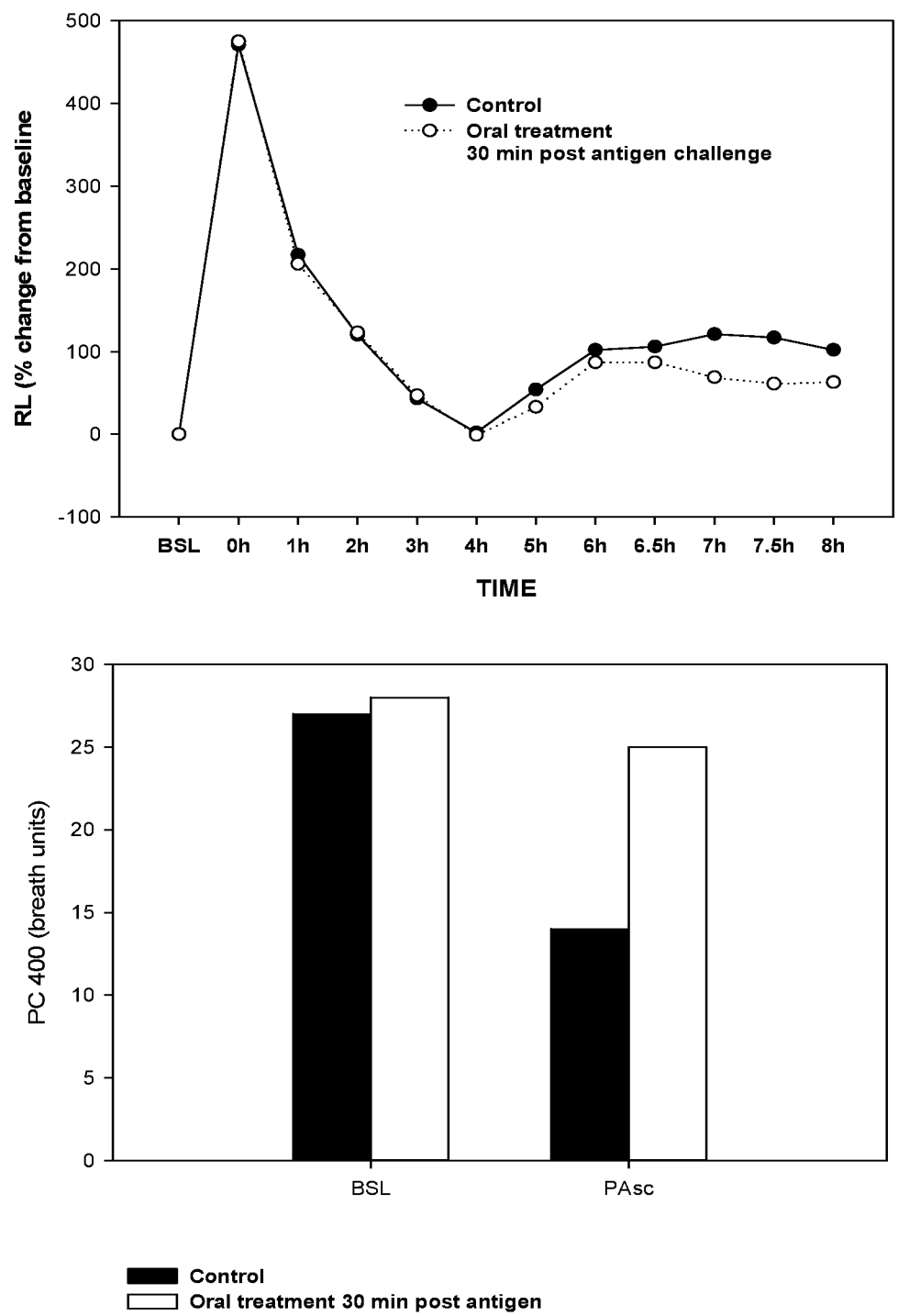

FIG. 18 shows the results for the lung resistance (RL) and PC 400 (breath units) for sheep provided with the compound formulation orally 30 minutes after antigen challenge, compared with the control.

Figure 19:
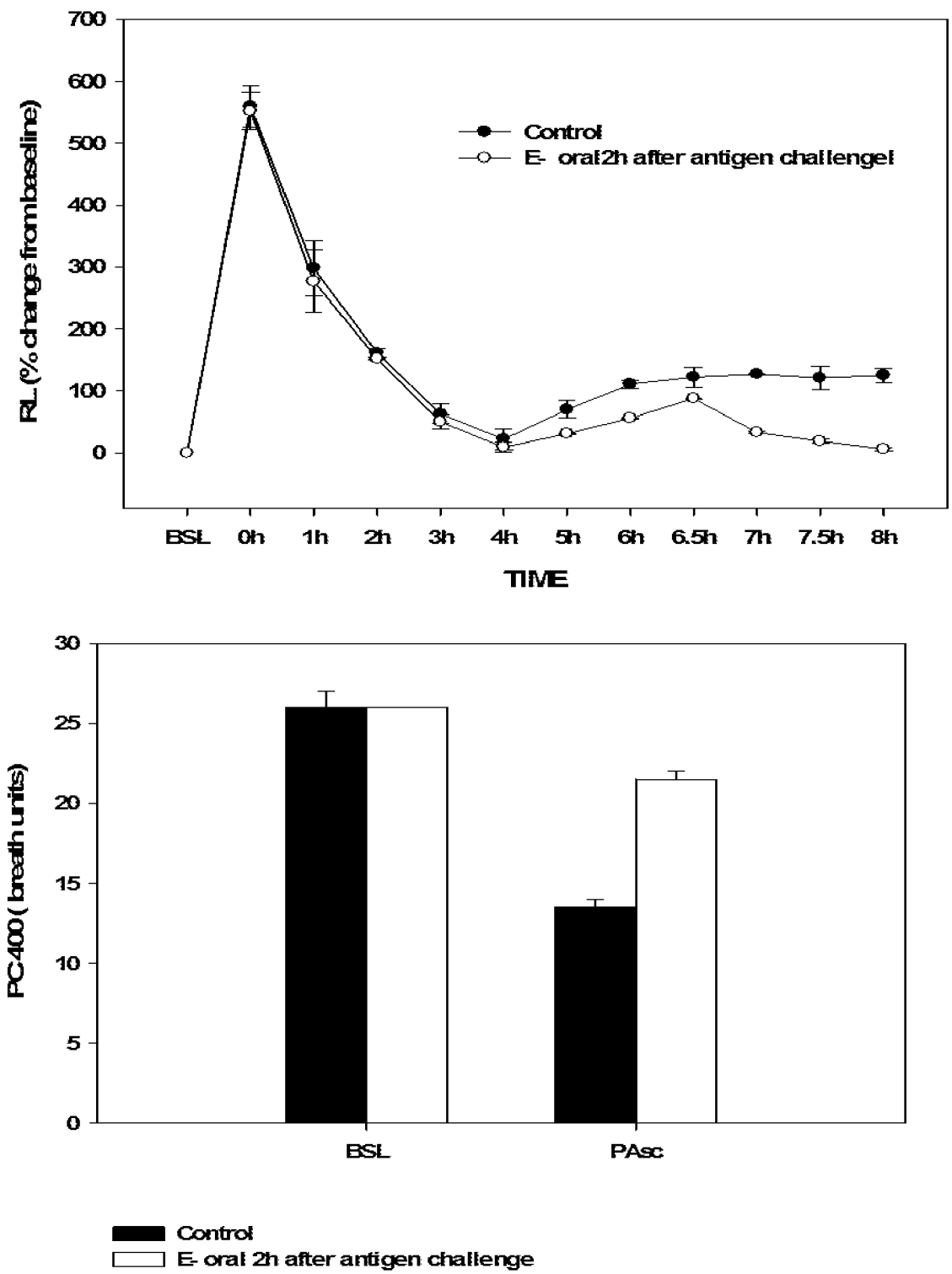

FIG. 19 shows the results for the lung resistance (RL) and PC 400 (breath units) for sheep provided with the formulation orally two hours after antigen challenge, compared with the control.

Figures 20, 21:
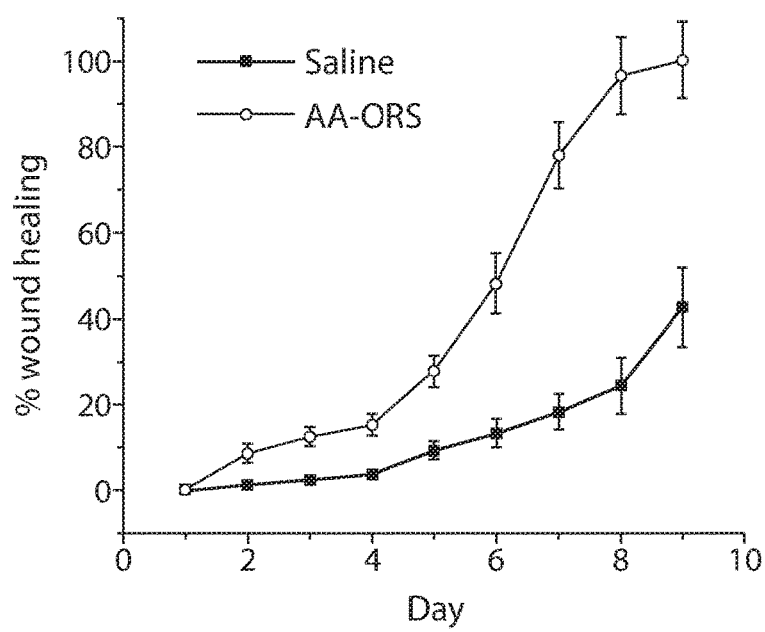

FIG. 20 shows a summary of the results of the asthma studies in sheep, including Average Late Airway Response ("LAR") and airway hyperreponsiveness ("AHR") for the control and sheep treated with the nebulized compound (5-8 hours) or provided with the amino acid formulation orally, before and after the aerosol antigen challenge, for antiinflammatory improved airway function. "*" indicates Average Late Airway Response (5-8 hours). "+" indicates Post Challenge/Pre Challenge PC 400. Ratio close to 1 indicates no airway hyperreponsiveness (AHR)

FIG. 21 shows the results of wound healing studies: Dorsal surface of the mice that was selected for surgery was shaved to remove the fur. All the surgical procedures were under anesthesia using 5% isoflurane in oxygen and the surgical plane of anesthesia was maintained using 1-3% isoflurane. 3 mm size punch biopsies were made on the dorsum of 8 week old NIH Swiss mice. Murine wound models can be affected by wound contraction because of the presence of a subcutaneous muscle layer, a layer that is absent in humans. To prevent wound contracture, a silicon O-ring was used as a splint and held in place by interrupted sutures. AA-ORS or saline was used in transparent occlusive dressing of the wounds. The dressing was changed every day after measuring the wound area using calipers. This procedure therefore measures re-epithelialization and mimics wound healing in humans. The outcome is shown in the figure. The data is from n=6 mice per group.

DETAILED DESCRIPTION

Described herein are compositions of amino acids for treating GI, lung, and skin disorders. In one aspect, described herein are compositions and methods for promoting cellular proliferation and/or development. In a certain embodiment, the cells are stem cells and/or the progenitor cells. As used herein, reference to "development" can include, for example, migration, maturation, and/or differentiation of the cells. The disclosure also provides compositions and methods for treating a wound, a skin condition (e.g., atopic dermatitis, psoriasis, bed sores, condition related to the aging of skin, cosmetic condition), a lung disorder (e.g., lung injury, pneumonitis, or asthma), a GI disorder (e.g., radiation injury, ischemic colitis, infection, trauma), or any other condition related to mucosal barrier function and/or integrity.

The compositions and methods can be used to enhance stem and/or progenitor cell populations in in vivo, ex vivo and/or in vitro. These cells are useful for providing treatment for many disease states, degeneration and injuries.

In one embodiment, provided herein are methods for promoting the proliferation and/or development of stem cells and/or the progenitor cells in a subject in need of such treatment by administering a composition of the present disclosure to the subject.

The subject may be a patient in which promoting the proliferation and/or development of stem cells and/or progenitor cells is needed. The patient may have this need due to, for example, malabsorption, radiation or chemotherapy-induced gastrointestinal toxicity, or secondary to an infection, cancer, or cancer therapy. In one embodiment, the patient is asymptomatic. The subject can be any animal, including, for example, a human. In addition to humans, the animal may be, for example, mammals, such as cattle, horses, sheep, pigs, goats, dogs, and cats. The animals may also be, for example, chickens, turkeys, or fish.

In certain embodiments, the composition comprises one or more free amino acids selected from the group consisting of threonine, valine, tyrosine, tryptophan, aspartic acid, and serine. In certain embodiments, the composition comprises one or more free amino acids selected from the group consisting of threonine, valine, tyrosine, tryptophan, aspartic acid, serine, and derivatives thereof. In certain embodiments, the composition comprises one or more free amino acids selected from the group consisting of threonine, valine, tyrosine, tryptophan, and aspartic acid. The composition preferably comprises one or more free amino acids selected from the group consisting of threonine, valine, serine, tyrosine, and tryptophan. In certain embodiments, the composition comprises two or more free amino acids selected from the group consisting of threonine, valine, tyrosine, tryptophan, aspartic acid, and serine. In certain embodiments, the composition comprises three or more free amino acids selected from the group consisting of threonine, valine, tyrosine, tryptophan, aspartic acid, and serine. In certain embodiments, the composition comprises four or more free amino acids selected from the group consisting of threonine, valine, tyrosine, tryptophan, aspartic acid, and serine. In certain embodiments, the composition comprises threonine, valine, tyrosine, tryptophan, and aspartic acid. In certain embodiments, the composition comprises the free amino acids of threonine, valine, tyrosine, tryptophan, and serine.

In one embodiment, the therapeutic composition comprises, consists essentially of, or consists of, one or more free amino acids selected from the group consisting of, threonine, valine, tyrosine, tryptophan, serine, aspartic acid, and derivatives thereof; and optionally, for example, pharmaceutically acceptable carriers, adjuvants, and other active agents. In certain embodiments, the composition comprises, one or more free amino acids selected from the group consisting of, threonine, valine, tyrosine, tryptophan, serine, and aspartic acid; and optionally, for example, pharmaceutically acceptable carriers, adjuvants, other active agents, and additives (e.g., sugars, electrolytes, vitamins, minerals, etc.).

In one aspect, the composition described herein comprises one or more free amino acids selected from the group consisting of threonine, valine, tyrosine, tryptophan, aspartic acid, or serine.

In some specific embodiments, the composition does not include one or more amino acids selected from the group consisting of lysine, glycine, isoleucine, and asparagine. In certain embodiments, the composition does not include lysine. In certain embodiments, the composition does not include glycine. In certain embodiments, the composition does not include isoleucine. In certain embodiments, the composition does not include asparagine. In certain embodiments, the composition does not include lysine and glycine. In certain embodiments, the composition does not include lysine and isoleucine. In certain embodiments, the composition does not include lysine and asparagine. In certain embodiments, the composition does not include lysine, glycine, and isoleucine. In certain embodiments, the composition does not include lysine, glycine, and asparagine. In certain embodiments, the composition does not include lysine, glycine, isoleucine, and asparagine. In certain embodiments, the composition does not include glycine and isoleucine. In certain embodiments, the composition does not include glycine and asparagine. In certain embodiments, the composition does not include glycine, isoleucine, and asparagine. In certain embodiments, the composition does not include isoleucine and asparagine. In certain embodiments, the composition does not include lysine, glycine, aspartic acid, isoleucine, and asparagine. In another specific embodiment, the composition does not include, or only includes negligible amounts of, serine, lysine, glycine, aspartic acid, isoleucine, and asparagine. certain embodiments, the composition does not include glutamine and/or methionine; and any di-, oligo-, or polypeptides or proteins that can be hydrolyzed into glutamine and/or methionine.

Or, in certain embodiments, even if these amino acids are present in the composition, they are not present in an amount that would inhibit stem cell and/or progenitor cell survival, proliferation, and/or development. In some embodiments the composition has no serine, or negligible amounts of serine. By "negligible" it is meant that the serine present has no effect on stem cell survival, proliferation, and/or development. By "negligible" it is meant that the serine present has no effect on a disease or conditions that is related to mucosal barrier function, e.g., wound healing, treating skin conditions (e.g., atopic dermatitis, psoriasis, bed sores, or condition related to the aging of skin), lung disorders (e.g., asthma), mucosal barrier function, and/or injury to GI mucosa in a subject in need thereof.

These amino acids, if present in the composition, may be present in, for example, the following concentrations: threonine at about 0.4 to about 1.5, about 0.7 to about 1.3, or about 0.9 to about 1.1 grams/liter; valine at about 0.7 to about 1.7, about 0.9 to about 1.5, or about 1.1 to about 1.3 grams/liter; serine at about 0.6 to about 1.6, about 0.8 to about 1.4, about 1.0 to about 1.2 grams/liter; tyrosine at about 0.05 to about 0.4, or about 0.1 to about 0.3 grams/liter; and tryptophan at about 1.1 to about 2.1, about 1.3 to about 1.9, or about 1.5 to about 1.7 grams/liter. In a certain embodiment, the composition comprises threonine (about 1.0 grams/liter), valine (about 1.2 grams/liter), serine (about 1.1 grams/liter), tyrosine (about 0.2 grams/liter), tryptophan (about 1.6 grams/liter), and aspartic acid (about 0.4 to 3.6 grams/liter). In certain embodiments, the composition has no, or negligible, serine. In certain embodiments, the concentration is grams amino acid per liter of solution. In certain embodiments, the solution comprises water.

In one embodiment, the total osmolarity of the composition is from about 100 mosm to about 280 mosm, or preferably, about 150 to about 260 mosm.

The composition may have a pH ranging from about 2.5 to about 8.5. In certain embodiments, the pH of the composition ranges from about 2.5 to about 6.5, about 3.0 to about 6.0, about 3.5 to about 5.5, about 3.9 to about 5.0, or about 4.2 to about 4.6. In other embodiments, the pH of the composition ranges from about 6.5 to about 8.5, about 7.0 to about 8.0, or about 7.2 to about 7.8.

In certain embodiments, the composition has a pH from, for example, about 2.5 to about 8.5. In certain embodiments, the composition has a pH from about 2.5 to about 6.5, about 2.5 to about 6.0, about 3.0 to about 6.0, about 3.5 to about 6.0, about 3.9 to about 6.0, about 4.2 to about 6.0, about 3.5 to about 5.5, about 3.9 to about 5.0, or about 4.2 to about 4.6. In other embodiments, the pH is about 6.5 to about 8.5, about 7.0 to about 8.5, about 7.0 to about 8.0, about 7.2 to about 8.0, or about 7.2 to about 7.8.

In some embodiments, the composition is administered systemically or locally. In certain embodiments, the composition is used to promote cellular survival, proliferation, and/or development ex vivo or in vitro. In certain embodiments, the composition is used for treating a disease or conditions that is related to mucosal barrier function, e.g., wound healing, treating skin conditions (e.g., atopic dermatitis, psoriasis, bed sores, or condition related to the aging of skin), treating lung disorders (e.g., asthma), improving mucosal barrier function, and/or treating injury to GI mucosa. The therapeutic composition can be administered via an enteral route or parenterally or topically or by inhalation. In certain embodiments, the composition is therapeutic, cosmetic, or nutritional.

In some embodiments, the composition (e.g., an amino acid-based oral rehydration solutions (AA-ORS)) described herein, which works by correcting the functional changes that happened at the GI mucosa following radiation. In certain embodiments, the composition is a solution. In certain embodiments, the solution is an amino acid-based oral rehydration solutions (AA-ORS)). The amino acids were selected to counter the increased paracellular permeability, increased $Cl^-$ secretion, and decreased absorption of electrolytes following radiation. Since the composition described herein (e.g., AA-ORS) corrects functional alterations in the GI mucosa, its action is thought to be upstream of the current agents in the pipeline. The composition can be administered with other therapeutic agents. It was recently found that electrolytes, glucose, and some amino acids are poorly absorbed in the GI tract following irradiation. In addition, it was observed that glucose and some amino acids can stimulate electrogenic Cl⁻ secretion in addition to Na⁺ absorption and can increase paracellular permeability, which further complicates radiation-induced diarrhea and increased gut permeability.[51,52] Increased paracellular permeability is known to increase translocation of antigenic substances from the gut lumen into the systemic compartment, causing an increase in pro-inflammatory cytokines.[51]

In one embodiment, the composition of the present disclosure does not include significant amounts of glucose, glutamine, methionine, and/or lactose. In certain embodiments, the composition does not include significant amounts of glucose. In certain embodiments, the composition does not include significant amounts of glutamine. In certain embodiments, the composition does not include significant amounts of methionine. In certain embodiments, the composition does not include methionine. In certain embodiments, the composition does not include significant amounts of lactose.

In one embodiment, the composition described herein is used as a composition for culturing cells for promoting survival, development, and/or proliferation of stem cells and/or progenitor cells. The composition for culturing cells may be used to obtain stem cells and/or progenitor cells in increased quantity in order to treat various diseases. The composition may also be applied to stem cells and/or progenitor cells immediately before and/or after transplantation. The composition may also be used to increase the proliferation of native stem cells present in various parts of the body.

In one embodiment, the present disclosure provides a method of improving therapeutic outcomes of implanted stem cells and/or progenitor cells comprising administering a composition in conjunction with stem cell and/or progenitor cell implantation or as a maintenance or supportive therapy following, for example, bone marrow or liver transplant. In certain embodiments, provided herein is a maintenance or supportive therapy following, for example, bone marrow or liver transplant. The administration of the composition can be at, or proximate to, a target stem and/or progenitor cell implantation site in a human or non-human animal. In an alternative embodiment, the environment may be further modified by providing influencing factors or by cleaning the environment of undesired or toxic agents that may affect administered stem and/or progenitor cells in an undesired way.

The administered cells may be unmodified or may be engineered to be biased toward a target differentiation endpoint. U.S. Patent Publication Nos. 2006/0134789 and 2006/0110440 are herein incorporated by reference in their entireties to provide examples of stem cells engineered for negative and positive differentiation biasing that are contemplated for use with the methods taught herein.

When the composition is applied to stem cells and/or progenitor cells either in culture, or in situ, changes occur in secretory proteins such as cell survival- and proliferation-related factors and transcription factors. As a result, the cellular activity is altered and, in particular, cell proliferation survival and/or development are enhanced. Accordingly, stem and/or progenitor cells produced in enhanced scale with the aid of the compositions according to the present invention may be transplanted into a disease or other site as a cell therapy agent in order to promote regeneration of cells and effectively treat various conditions.

In one embodiment, the composition described herein stimulates the survival, proliferation, and/or development of stem cells and/or progenitor cells as evidenced by one or more of: 1) an increase in proliferation markers, such as p-ERK and p-AKT, at mRNA and/or protein levels, 2) an increase in stem cell markers, such as BMI1 and Lgr5, at mRNA and/or protein levels, 3) an activation of a protein kinase, such as MEK and ERK; and 4) a decrease in apoptosis markers, such as cleaved caspase 3.

ERK is a protein known to communicate cell surface signals to the nucleus for mediating the transcriptional and translational changes necessary to bring about proliferation. ERK1 and ERK2 are 44-kDa and 42-kDa proteins that are an important subfamily of protein kinases that control a broad range of cellular activities and physiological processes, including cell proliferation and differentiation by down-regulating pro-apoptotic molecules and upregulating anti-apoptotic molecules. Activation of MEK1/2 leads to the phosphorylation of ERK1 and ERK2. Upon stimulation, ERK1/2 becomes phosphorylated on threonine and tyrosine residues, and the latter results in the dissociation of ERK1/2 from MEK1/2. ERK1/2 then translocates to the nucleus. In one embodiment, the compositions described herein help maintain the mitogenic stimulus until late G1 for successful S-phase entry.

AKT is a serine/threonine-specific protein kinase that plays a role in cell proliferation and survival and inhibits apoptosis and metabolism. Phosphorylation of AKT activates AKT. Like pERK, AKT is also known to play a role in the cell cycle. AKT could also promote growth factor-mediated cell survival. A variety of studies have documented the key role of the Akt pathway in preventing apoptotic cell death.[9] PCNA, a distinctive protein linked to DNA replication and therefore used as a marker for proliferation was measured with AA-ORS or saline treatment. AA-ORS increased PCNA in 0 Gy and 5 Gy irradiated mice, but not in saline treated mice. Increase in PCNA is an early indication for small intestinal epithelial proliferation. Together these studies suggest enhanced proliferation with treatment using AA-ORS.

Caspase-3 is an executioner, or effector of apoptosis, as cleaving of protein substrates within the cell leads to morphological changes associated with apoptosis, including DNA degradation and chromatin condensation, and membrane blebbing to trigger the apoptotic process. This inactive pro-enzyme is activated by proteolytic cleavage.[7,46] The study showed that radiation increased caspase-3 and that AA-ORS treatment decreased cleaved caspase-3 in the villus epithelial cells of 0 Gy and 5 Gy mice. Bcl-2, a downstream target for Erk1/2, is known to inhibit Bax in the intrinsic pro-apoptotic pathway. Increased Bcl-2 protein levels with AA-ORS suggest a protective mechanism to prevent apoptosis. However, increased protein levels of Bcl-2 in tissues from irradiated mice may suggest a radio-protective mechanism. Similar increase in Bcl-2 protein levels following irradiation has been reported and agree with the previous findings (Ezekwudo, D. et al. Inhibition of expression of anti-apoptotic protein Bcl-2 and induction of cell death in radioresistant human prostate adenocarcinoma cell line (PC-3) by methyl jasmonate. Cancer Lett 270, 277-285, doi: 10.1016/j.canlet.2008.05.022 (2008). However, Bax protein failed to show significant changes with radiation or with treatment, suggesting AA-ORS effect on apoptosis at a step upstream to Bax26. Increased p-Akt in AA-ORS-treated mice suggests its action may be by activation of proliferation or inhibiting apoptosis (FIG. 5). Together with the effects seen on caspase-3 and Bcl-2, these results could explain the pro-survival effect and increased proliferation observed with AA-ORS treatment. However, further studies will be needed to characterize the mechanisms by which AA-ORS activates Erk1/2 and Akt, PCNA caspase-3, Bcl-2 or Bax.

p53

Figure 7:
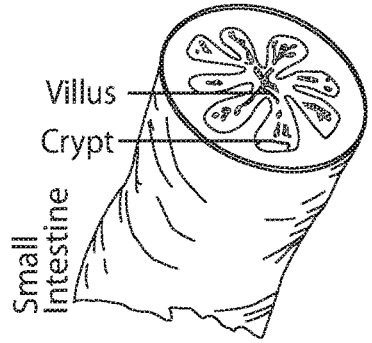
FIG. 7 shows a schematic figure of small intestinal villus and enterocytes: AA-ORS treatment increases rapidly dividing stem cells that are Lgr5 positive as well as proliferation markers p-ERK, p-AKT, and PCNA. The treatment also increases cleaved caspase 3, p53, and Bc1-2. AA-ORS treatment increases villus heights, increased expression of NHE3, SGLT1 and β-galactosidases, thereby increasing electrolyte absorption, sodium-coupled glucose absorption, and break down of disaccharides at the brush border membrane, respectively. A cartoon of the enterocyte on the top right shows the functional improvement in NHE3 mediated $Na^+$ absorption and glucose-coupled sodium transport with AA-ORS.
Figure 7:
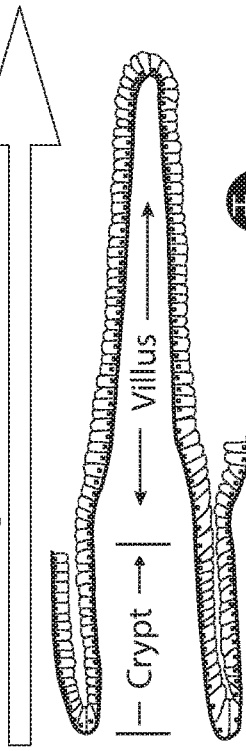
Figure 7:
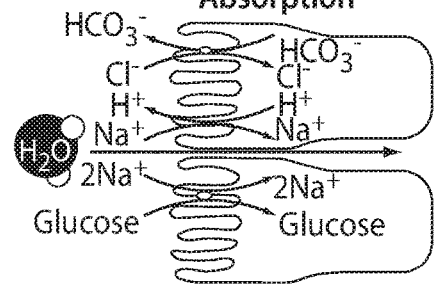
Figure 8A:
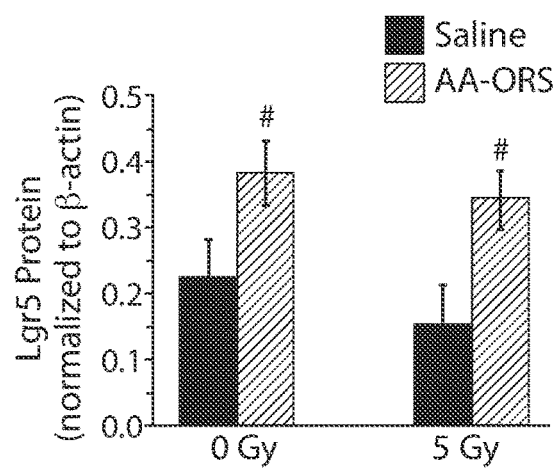
FIG. 8 shows protein density. Protein density was normalized to b-actin. Mice treated with saline are shown as black bars and AA-ORS treated are shown as hatched bars following 0 or 5 Gy irradiation. (Values are means±SEM from n=4 different mice repeated in triplicate. #P<5 compared with saline control. (8A). Lgr5 protein; (8B). Bmil protein; (8C). p-ERK protein; (8D). p-AKT protein; (8E). AKT protein; (8F). Caspase-3 protein (normalized to b-actin).
Figure 8B:
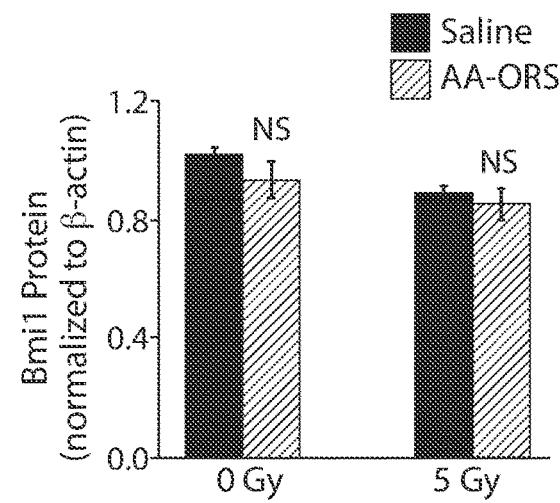
Figure 8C:
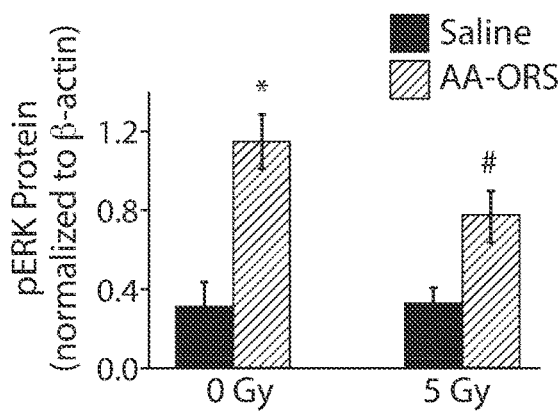
Figure 8D:
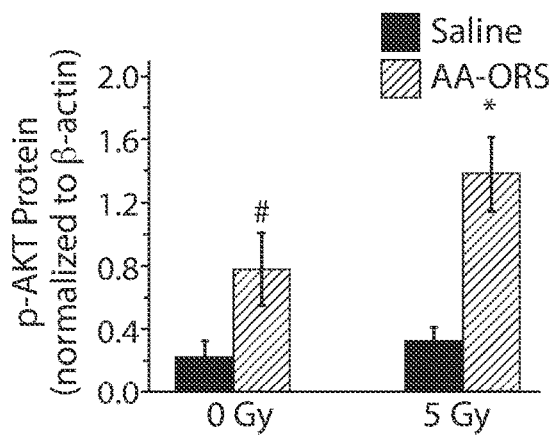
Figure 8E:
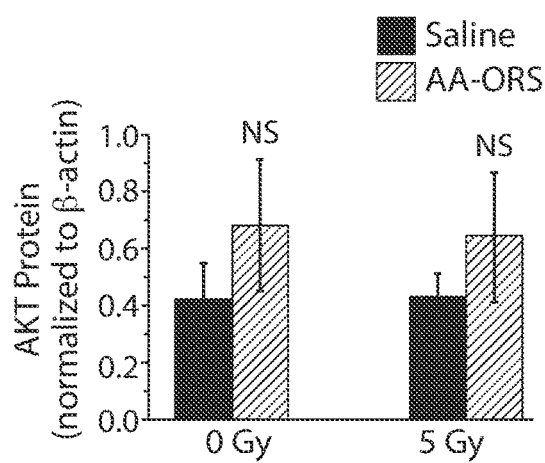
Figure 8F:
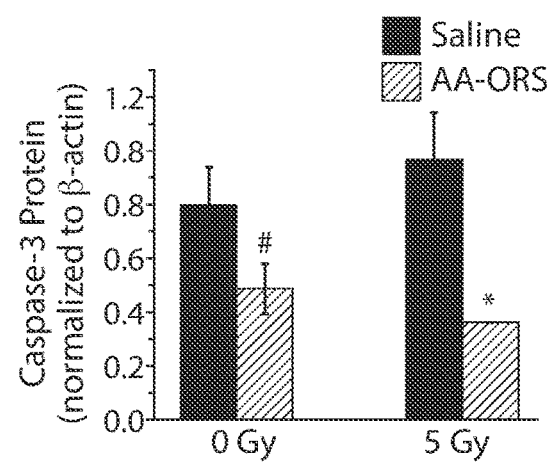
Figure 9A:
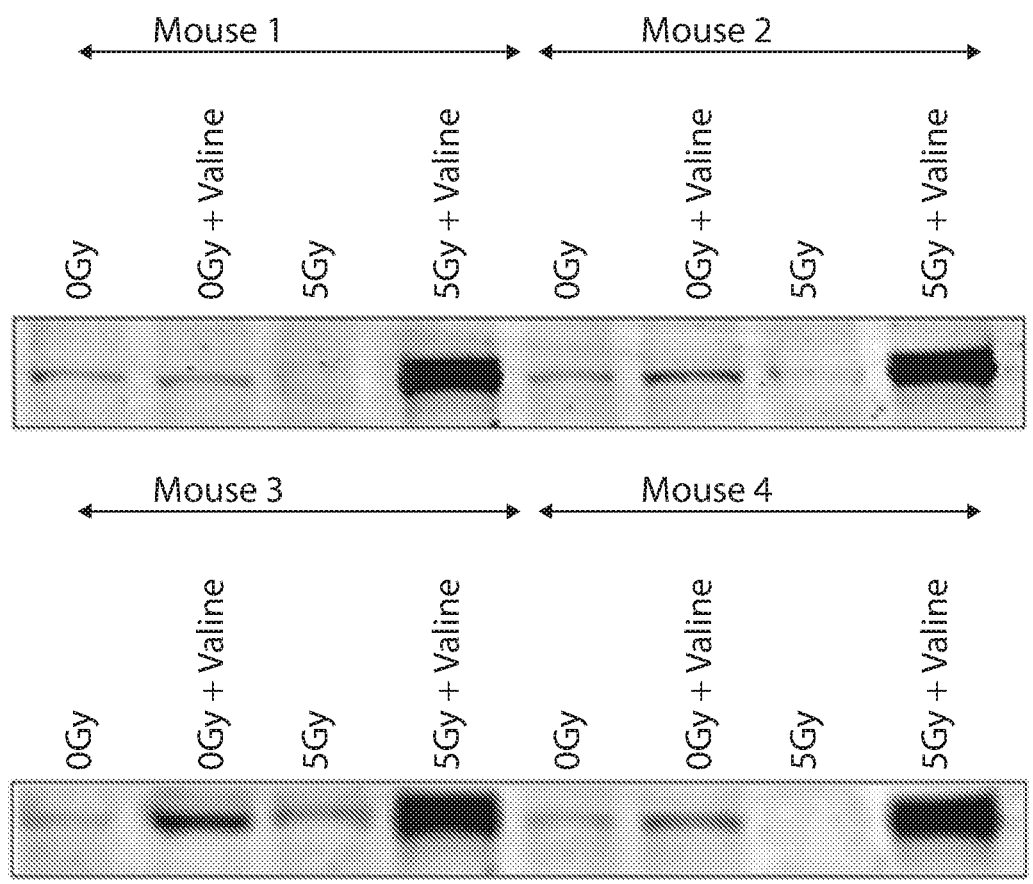
FIG. 9A shows Western analysis results showing that gastric gavage using valine increases Lgr5 protein levels in 0 Gy irradiated and 5 Gy irradiated mice.
Figure 9B:
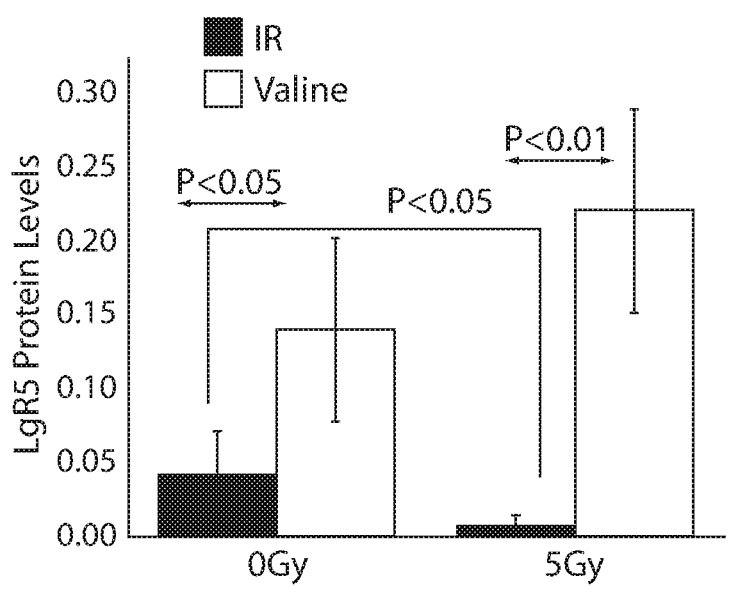
FIG. 9B shows a graphical representation of the protein levels of Lgr5 protein in mice treated with valine for a period of 6 days. For FIGS. 9-13, the data is from Male NIH Swiss mice (8 weeks) treated with individual amino acids (FIG. 9 (valine)
Figure 10A:
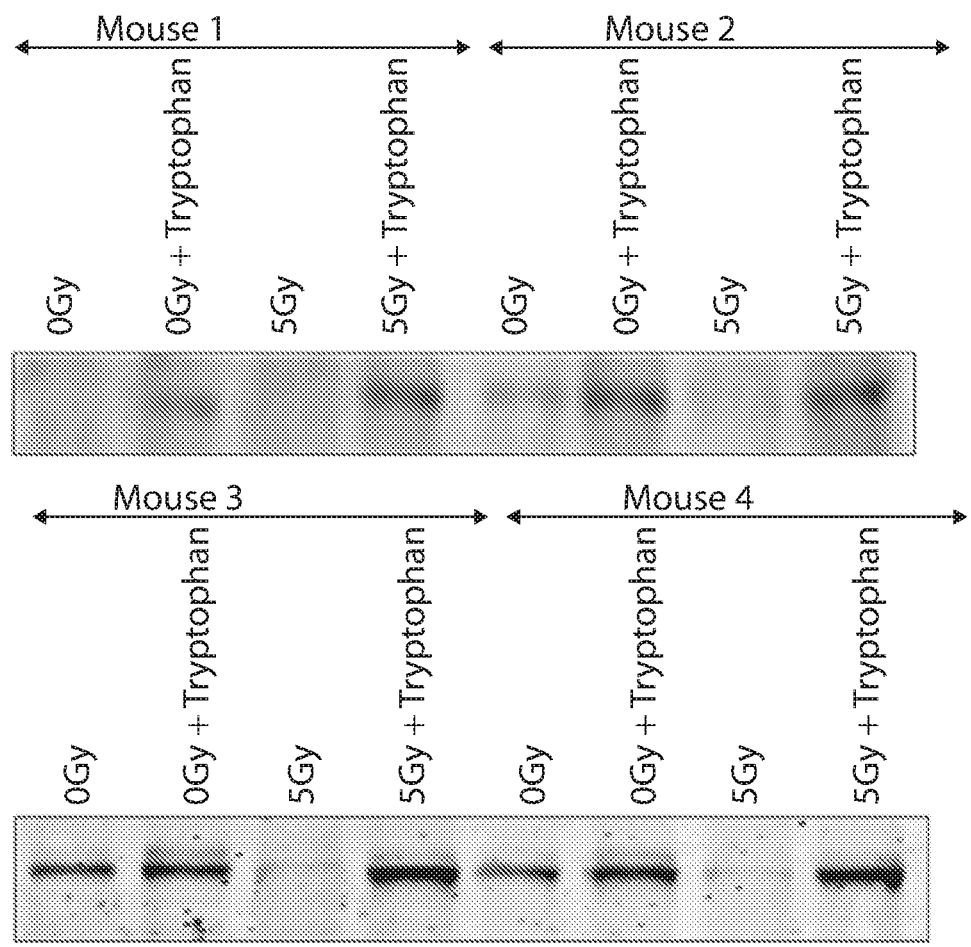
FIG. 10A shows changes in Lgr5 protein levels with tryptophan treatment for a period 6 days.
Figure 10B:
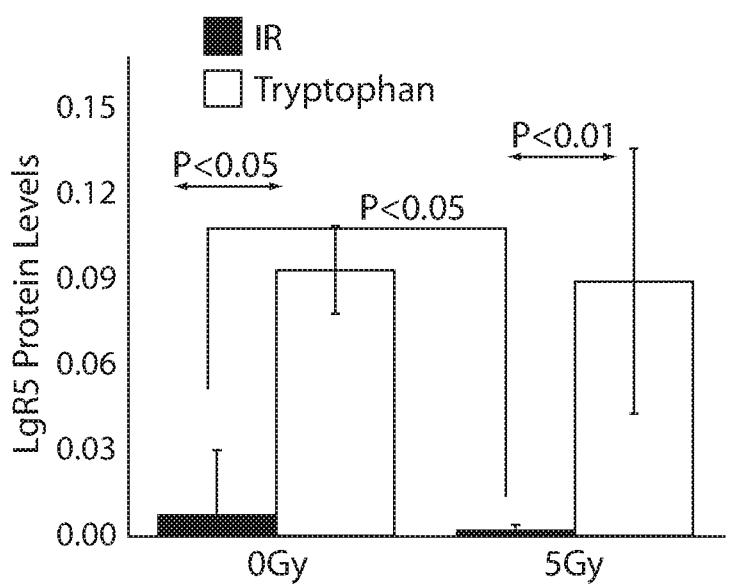
FIG. 10B shows a graphical representation of Lgr5 protein levels in mice treated with tryptophan for a period of 6 days.
Figure 11A:
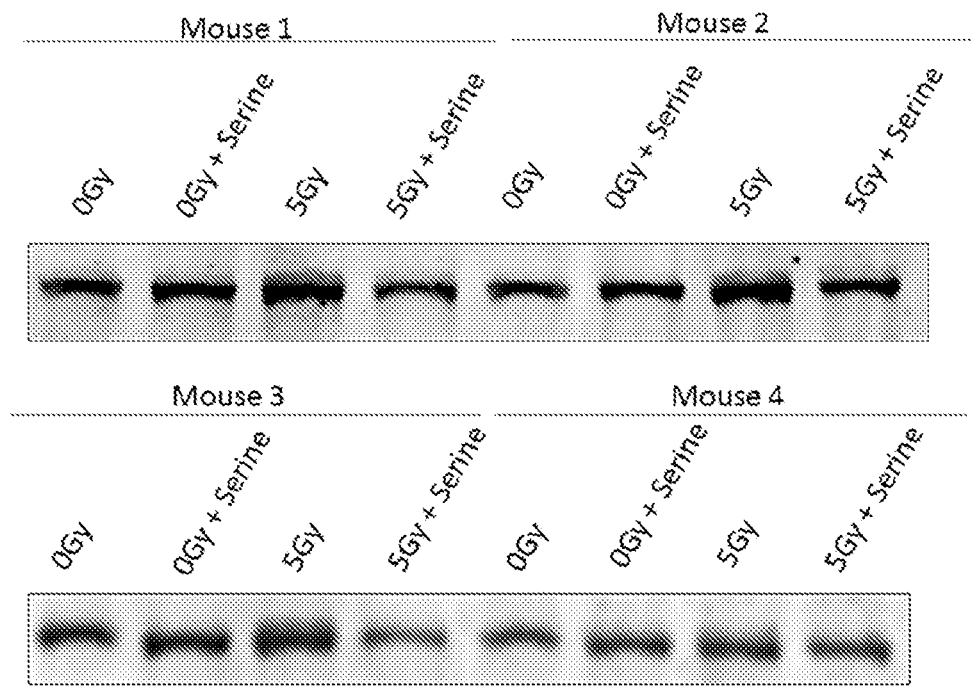
FIG. 11A shows changes in Lgr5 protein levels with serine treatment for a period 6 days.
Figure 11B:
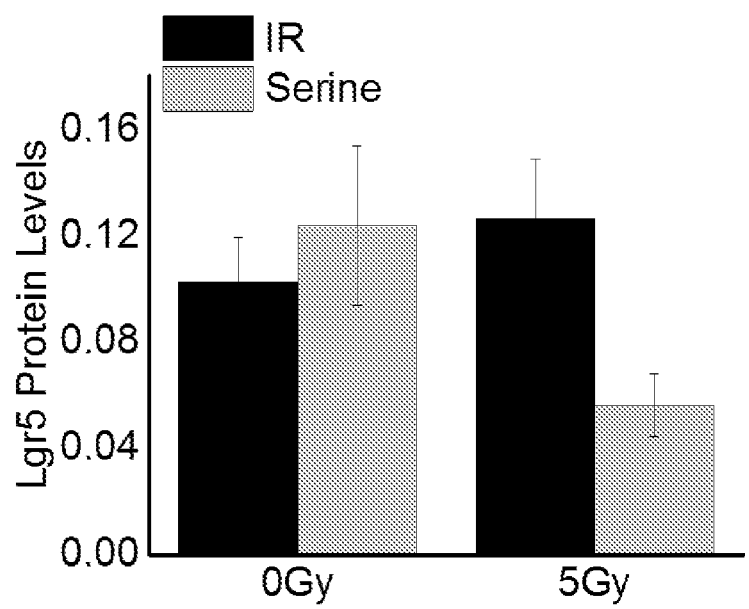
FIG. 11B shows a graphical representation of Lgr5 protein levels in mice treated with serine for a period of 6 days.
Figure 12A:
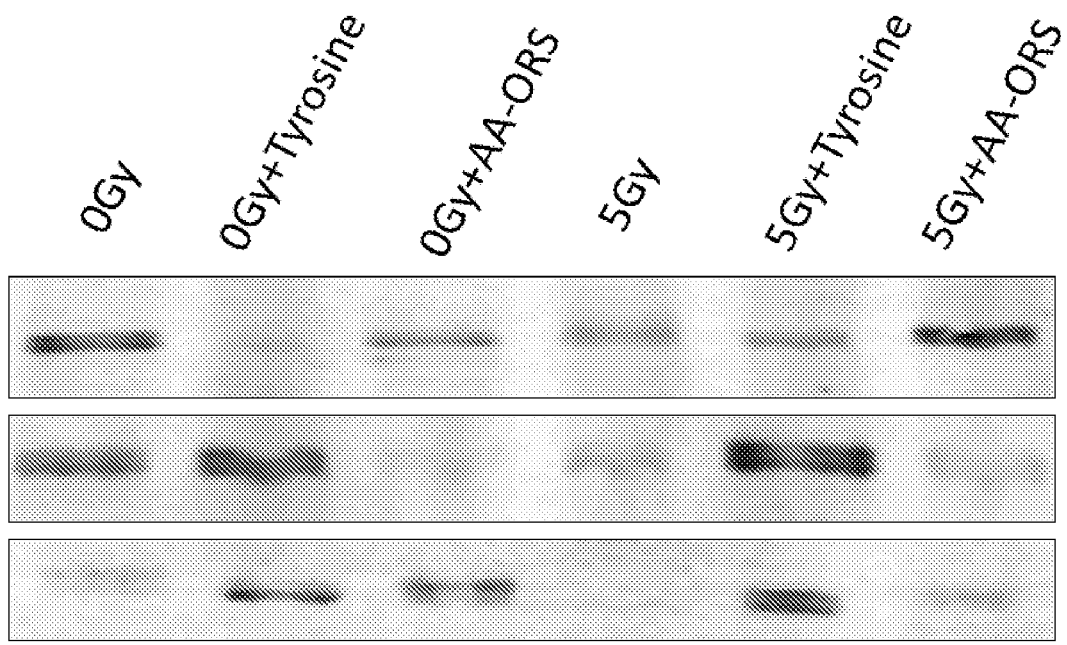
FIG. 12A shows changes in Lgr5 protein levels with tyrosine treatment for a period 6 days.
Figure 12B:
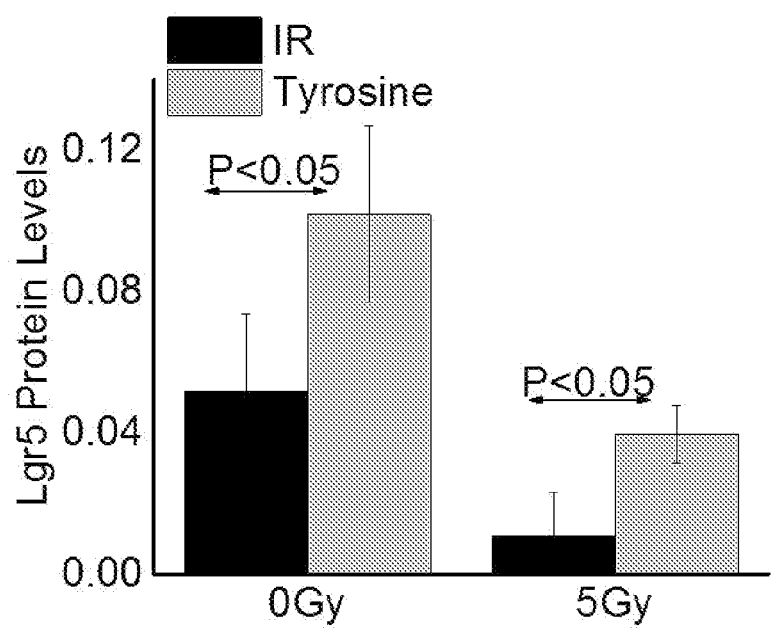
FIG. 12B shows a graphical representation of Lgr5 protein levels in mice treated with tyrosine for a period of 6 days.
Figure 13:
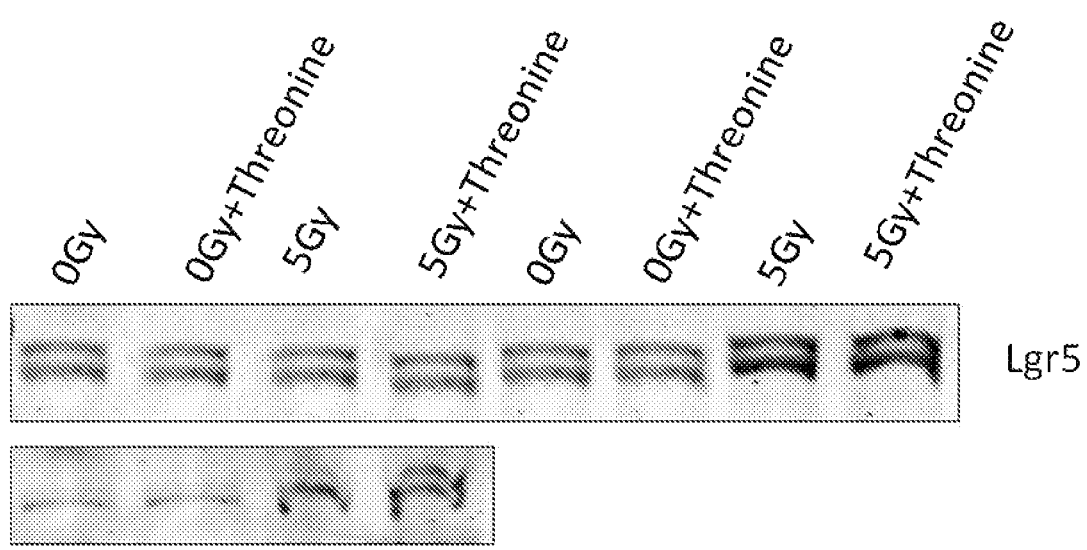
FIG. 13 (threonine)), as by gastric savage (300 ul OD) for a period of 6 days. Animals were sacrificed on day 6 by CO2 euthanasia and tissues collected for resolving the protein by western blot analysis. Lgr5 (100 KD) was used as the marker for crypt stem cell proliferation. These experiments are repeated at least 4 times (data shown) from 4 different mice.

Since Akt could also play prominent roles in malignant transformation,[10] the role of p53, a known tumor suppressor protein, was studied with AA-ORS. Changes in the p53 protein may suggest that AA-ORS has tumor-suppression effects. Mutations in the p53 tumor-suppressor53 gene are the most frequently observed genetic lesions in human cancers. Mice homozygous for the null allele appear normal but are prone to the spontaneous development of a variety of tumors.[11] p53 has also been shown to play an important role in the radiation response; indeed, the level of p53 accumulation in response to irradiation primarily results from the intensity of DNA damage.[12] Studies have shown that stem cell loss plays an important role in radiation-induced acute intestinal injury and lethality and is regulated by the p53 pathway and its transcriptional targets PUMA and p21.[23,34,37] PUMA-dependent apoptosis quickly reduces intestinal stem cells (ISC) and its progenitors in hours following high-dose irradiation, and deficiency of PUMA leads to improved animal survival and crypt regeneration by enhancing p21-dependent DNA repair and is crucial for 38 radiation-induced intestinal damage.[24,38] Together with Lgr5, p-Erk, and p-Akt, the changes in cleaved caspase-3 suggest that AA-ORS increased villus height in intestinal tissues from non-irradiated and irradiated mice not only through proliferation but also through decreased apoptosis and increased cell survival. To assess if the villus epithelial cells resulting from increased proliferation and decreased apoptosis are mature, differentiated, and functionally active, $Na^+$ absorptive capacity and glucose-stimulated $Na^+$ absorption were measured. Both NHE3, the predominant transporter of $Na^+$ absorption in the small intestine, and SGLT1, the transporter for sodium-coupled glucose absorption, were only found in mature and differentiated villus cells; they had increased function (FIGS. 3 & 4) as well as increased mRNA and protein levels. These studies suggest that AA-ORS treatment following irradiation increased electrolyte and glucose absorption (FIGS. 3, 4, & 7).

In one embodiment, the compositions described herein are useful for preventing damage to DNA and/or repairing damaged DNA. In another embodiment, the composition promotes the proliferation and/or development of stem and/or progenitor cells by preventing or reducing damage to DNA and/or repairing damaged DNA.

Irradiation, Crypt Count, Villus Length, and Immunohostichemistry

It was found that increased weight gain and survival could be secondary to increased crypt number and villus height that then increased the surface area of absorption. It was demonstrated that crypt number and villus height increased with AA-ORS treatment beginning 6 days after irradiation. Using the single-hit, multi-target model for crypt survival, it was found that the number of crypt progenitor units per ileal circumference (N) increased significantly (P<0.001) without a change in DO (4.8±0.1 Gy) (FIG. 1A). The Dq values improved the equivalent to an increased radiation tolerance of 1.7 Gy with AA-ORS treatment, indicating improved crypt survival. The crypt survival studies suggested an increase in progenitor units or stem cells per crypt. Thus, it wasexamined the effect of irradiation and AA-ORS on stem cell number using antibodies specific to intestinal stem cell markers and migration of the daughter cells into the villus secondary to proliferation by EdU incorporation.[2,4,36] At least three distinct crypt cell types are postulated to represent intestinal stem cells (ISC).[2] Each member of the population has distinct proliferation kinetics and sensitivities to radiation; therefore, each is thought to serve a unique function.[31] They are believed to dynamically switch from one type to the other in response to inhibitory and stimulatory signals caused by cytokines, hormones, or growth factors.[25] In contrast, slow-cycling intestinal epithelial stem cells (IESC) [label-retaining cells (LRC)] at the "+4 crypt position" contribute to homeostatic regenerative capacity, particularly during recovery from injury.[33] These LRC express various markers, such as Bmil, HopX, Lrigl, and/or Dclkl, and can change to rapidly cycling IESCs in response to injury.[34] Lgr5 can mark both cells, whereas Bmi 1 and HopX were reported to preferentially mark+4 cells. 15 Lgr5+ ISC are necessary for intestinal regeneration following radiation injury.[35] Lgr5- and Bmil are thought to be reserve cells that mount regenerative response following injury or radiation-induced damage. Studies have shown that the loss of Lgr5+ cells is tolerated due to activation of the Bmil-expressing stem cell pool.[2,30]

The amino acid formulation AA-ORS that increases villus height has important implications for disease conditions characterized by a decrease in villus height that are outside of radiation or chemotherapy-induced toxicity, such as Crohn's disease, celiac disease, malnutrition, and environmental enteropathy. This study signifies how a systematic selection of certain nutrients based on their beneficial effect on GI function helped to improve in situ intestinal stem cell proliferation, maturation, and differentiation, leading to functionally active long villus epithelial cells whose function and height were initially compromised by irradiation (FIG. 7). The study also supports the Leibowitz et al. observation that bone marrow derived stem cells have no significant role in the repopulation of intestinal mucosa following high dose radiation (Leibowitz, B. J. et al. Ionizing irradiation induces acute haematopoietic syndrome and gastrointestinal syndrome independently in mice. Nat Commun 5, 3494, doi:10.1038/ncomms4494 (2014)). Future studies should seek to determine the mechanisms by which these amino acids increase the stem cell population, increase their proliferation, and decrease apoptosis and also to rule out malignant transformation. The work highlights the importance of careful selection of different nutrients or individual amino acids to affect various stem cell populations, including hematopoietic stem cells.

Stem Cells and/or Progenitor Cells

The compositions and methods described herein can be used to increase survival, proliferation, and/or development of stem cells and/or progenitor cells. The cells can be, for example, embryonic, pluripotent or totipotent, and can be in vivo or in vitro.

A stem cell is typically capable of differentiation into ectodermal, mesodermal, and endodermal cells. Pluripotent stem cells are undifferentiated cells that have the capability of differentiating into a variety of cell types. Totipotent stem cells are undifferentiated cells with the capability of differentiating into all cell types and, by definition, imply germ-line transmission.

In one embodiment, the stem cells are mesenchymal stem cells that have a potential to differentiate into, for example, osteoblasts, chondrocytes, adipocytes, fibroblasts, smooth muscle cells, stromal cells, tendon cells, epithelial cells, nerve cells, and vascular endothelial cells.

In one embodiment, the cells are embryonic stem (ES) cells, which can proliferate indefinitely in an undifferentiated state. Furthermore, ES cells are totipotent cells, meaning that they can generate all of the cells present in the body (bone, muscle, brain cells, etc.). ES cells have been isolated from the inner cell mass (ICM) of the developing murine blastocyst (Evans et al., Nature 292:154-156, 1981; Martin et al., Proc. Natl. Acad. Sci. 78:7634-7636, 1981; Robertson et al., Nature 323:445-448, 1986). Additionally, human cells with ES properties have been isolated from the inner blastocyst cell mass (Thomson et al., Science 282:1145-1147, 1998) and developing germ cells (Shamblott et al., Proc. Natl. Acad. Sci. USA 95:13726-13731, 1998). Human and non-human primate embryonic stem cells have been produced (see U.S. Pat. No. 6,200,806, which is incorporated by reference herein).

In one embodiment, the cells are adult stem cells, which self-renew and generate differentiated cells. Adult stem cells, also called somatic stem cells, are stem cells that maintain and repair the tissue in which they are found. These cells can be, for example, bone marrow stem cells.

Somatic precursor cells can also be utilized with the methods disclosed herein. Somatic precursor cells can be isolated from a variety of sources using methods known to one skilled in the art. Somatic precursor cells can be of ectodermal, mesodermal, or endodermal origin. Any somatic precursor cells that can be obtained and maintained in vitro can be used in accordance with the present methods. Such cells include cells of epithelial tissues such as the skin and the lining of the gut, embryonic heart muscle cells, and neural precursor cells (Stemple and Anderson, 1992, Cell 71:973-985). Such cells also include pancreatic stem cells, cord blood stem cells, peripheral blood stem cells, and stem cells derived from adipose tissues.

In one embodiment, the stem cells further include pluripotential stem cells obtained by reprogramming somatic cells. Somatic cell reprogramming is the process of converting the epigenetic state of a differentiated somatic cell into a pluripotent state capable of giving rise to any cell type. Somatic cell reprogramming can be achieved by for example, transferring a somatic nucleus into a donor oocyte, which is termed somatic cell nuclear transfer (SCNT). Somatic cell reprogramming can also be achieved by direct reprogramming, termed induced pluripotent stem cells (iPSCs), for example, by the simultaneous retroviral expression of the four transcription factors Oct4, Sox2, Klf4, and C-myc. These iPSCs share all the key characteristics of ES cells.

In another embodiment, other post-embryonic stem cells can be obtained beginning from week 12 after gestation from foetal liver, perinatal umbilical cord blood (UCB), human bone marrow or G-CSF stimulated peripheral blood.

In certain embodiments, the stem cells are neural stem cells (NSCs), skin stem cells, hematopoietic stem cells (HSCs), mesenchymal stem cells (MSCs), tissue stem cells (e.g., muscle stem cells), mesodermal stem cells, organ stem cells (e.g., pancreatic stem cells and liver stem cells), or intestinal stem cells. In certain embodiments, the stem cells are adult stem cells, embryonic stem cells, cancer stem cells, neural stem cells (NSCs), skin stem cells, hematopoietic stem cells (HSCs), mesenchymal stem cells (MSCs), tissue stem cells (e.g., muscle stem cells), mesodermal stem cells, organ stem cells (e.g., pancreatic stem cells and liver stem cells), or intestinal stem cells.

In one embodiment, the cells are neuronal stem cells. In non-limiting examples, the cells are neuronal precursor cells and/or glial precursor cells. Undifferentiated neural stem cells differentiate into neuroblasts and glioblasts, which give rise to neurons and glial cells.

Neural stem and progenitor cells can participate in aspects of normal development, including migration along well-established migratory pathways to disseminated CNS regions, differentiation into multiple developmentally- and regionally-appropriate cell types in response to microenvironmental cues, and non-disruptive, non-tumorigenic interspersion with host progenitors and their progeny.

Human NSCs are capable of expressing foreign transgenes in vivo in these disseminated locations. As such, these cells find use in the treatment of a variety of conditions, including traumatic injury to the spinal cord, brain, and peripheral nervous system; treatment of degenerative disorders including Alzheimer's disease, Huntington's disease, and Parkinson's disease; affective disorders including major depression; stroke; and the like.

In one embodiment, the stem cells are muscle stem cells. Muscle tissue in adult vertebrates regenerates from reserve myoblasts called satellite cells. Satellite cells are distributed throughout muscle tissue and are mitotically quiescent in the absence of injury or disease. Following recovery from damage due to injury or disease or in response to stimuli for growth or hypertrophy, satellite cells reenter the cell cycle, proliferate and undergo differentiation into multinucleate myotubes, which form new muscle fiber. The myoblasts ultimately yield replacement muscle fibers or fuse into existing muscle fibers, thereby increasing fiber girth by the synthesis of contractile apparatus components. Criteria for myogenicity include the expression of myogenic proteins, which include the intermediate filament protein desmin, and myogenic transcription factors MyoD, Myf-5, and Pax-7.

In one embodiment, the stem cells are hair follicle stem cells. The hair follicle bulge area is an abundant, easily accessible source of actively growing, pluripotent adult stem cells. Nestin, a protein marker for neural stem cells, is also expressed in follicle stem cells as well as in their immediate differentiated progeny. The nestin-expressing hair follicle stem cells differentiate into, for example, neurons, glial cells, keratinocytes, and smooth muscle cells in vitro.

In one embodiment, the stem cells are pancreatic stem cells and pancreatic multipotent progenitor (PMP) cells. These cells may be isolated from the pancreatic islet- and duct-derived tissue and further develop to, for example, other PMP cells or neural or pancreatic cells. The pancreatic cells optionally include alpha cells, delta cells, beta cells, pancreatic exocrine cells, and pancreatic stellate cells. α cells are mature glucagon producing cells. In vivo, these cells are found in the pancreatic islets of Langerhans. β-cells are mature insulin producing cells. In vivo, these cells are also found in the pancreatic islets of Langerhans. Pancreatic stem cells are important in treatment of diabetes, in particular, type I diabetes, for providing β-cells.

In one embodiment, the stem cells are bone marrow stem cells. Bone marrow stem cells are cells that are generated in bone marrow and which can differentiate into cells of various body tissues. Bone marrow stem cells are also capable of recovering a lost function of a tissue by differentiating into cells of the tissue under the influence of a differentiation inducer. Examples of the bone marrow stem cells include bone marrow mesenchymal stem cells capable of differentiating into, for example, bone cells, chondrocytes, adipocytes, myocytes, tenocytes, or bone marrow stromal cells, and hematopoietic stem cells capable of differentiating into blood cells, such as erythrocytes and leukocytes.

In one embodiment, the stem cells are of the gastrointestinal tract. Epithelial cells line within the gastrointestinal tract. Turnover of these cells is a constant process under normal homeostasis and increasing after damage. Multipotent stem cells regulate this process by generating all gastrointestinal epithelial cell lineages and even whole intestinal crypts and gastric glands. These stem cells situated in the lower portion of the intestinal crypts, including fast cycling crypt base columnar cells (CBCs) and more quiescent "+4" cells above Paneth cells in mammals.

At least three distinct crypt cell types are postulated to represent intestinal stem cells (ISC). Each member of the population has distinct proliferation kinetics and sensitivities to radiation; therefore, each is thought to serve a unique function. They are believed to dynamically switch from one type to the other in response to inhibitory and stimulatory signals caused by cytokines, hormones, or growth factors. In contrast, slow-cycling intestinal epithelial stem cells (IESC) [label-retaining cells (LRC)] at the "+4 crypt position" contribute to homeostatic regenerative capacity, particularly during recovery from injury. These LRC express various markers, such as BMI1, HOPX, LRIG1, and/or DCLK1, and can change to rapidly cycling IESCs in response to injury. Lgr5 can mark both cells, whereas Bmi1 and HopX were reported to preferentially mark+4 cells. Lgr5+ ISC are necessary for intestinal regeneration following radiation and/or chemotherapy-induced gastrointestinal injury. LgrS− and BMI1 are thought to be reserve cells that mount regenerative response following injury or radiation-induced damage. Similarly, the formulation could be used in subclinical disease conditions such as environmental enteropathy that are associated with increased gut permeability, increased local and systemic inflammation, and decreased villus height. The subjects with environmental enteropathy experience chronic malnutrition secondary to malabsorption of nutrients and minerals.

Compositions for Promoting Proliferation and/or Development of Stem Cells and/or Progenitor Cells, and for Wound Healing, Treating Skin Conditions, Lung Disorders, Mucosal Barrier Conditions, and a Disease or Conditions that are Related to Mucosal Barrier Function, and Treating Injury to GI Mucosa In one aspect, provided herein are therapeutic compositions for promoting the survival, proliferation, and/or development of stem cells and/or progenitor cells. Described herein are compositions and methods for treating a disease or conditions that are related to mucosal barrier function, e.g., wound healing, treating skin conditions (e.g., atopic dermatitis, psoriasis, bed sores, or condition related to the aging of skin), treating lung disorders (e.g., asthma), improving mucosal barrier function, and/or treating injury to GI mucosa in a subject in need thereof.

In one embodiment, the therapeutic composition comprises, consists essentially of, or consists of, one or more free amino acids selected from the group consisting of, threonine, valine, tyrosine, tryptophan, aspartic acid, serine and derivatives thereof; and optionally, pharmaceutically acceptable carriers, adjuvants, and/or additional active ingredients. In one embodiment, the therapeutic composition comprises, consists essentially of, or consists of, one or more free amino acids selected from the group consisting of, threonine, valine, tyrosine, tryptophan, aspartic acid, and serine; and optionally, pharmaceutically acceptable carriers, adjuvants, and/or additional active ingredients. In certain embodiments, the composition is sterile.

In one embodiment, the total osmolarity of the composition is from about 100 mosm to about 280 mosm, or any value therebetween. Preferably, the total osmolarity is from about 150 to about 260 mosm. In another embodiment, the composition has a total osmolarity that is any value lower than about 280 mosm.

The composition may have a pH from, for example 2.5 to 8.5. In certain embodiments, the composition has a pH from about 2.5 to about 6.5, about 3.0 to about 6.0, about 3.5 to about 5.5, about 3.9 to about 5.0, or about 4.2 to about 4.6. In other embodiments, the pH is about 6.5 to about 8.5, about 7.0 to about 8.0, or about 7.2 to about 7.8.

In certain embodiments, the composition comprises one or more free amino acids selected from the group consisting of threonine, valine, tyrosine, tryptophan, aspartic acid, and serine. In certain embodiments, the composition comprises one or more free amino acids selected from the group consisting of threonine, valine, tyrosine, tryptophan, aspartic acid, serine, and derivatives thereof. In certain embodiments, the composition comprises one or more free amino acids selected from the group consisting of threonine, valine, tyrosine, tryptophan, and aspartic acid. The composition preferably comprises one or more free amino acids selected from the group consisting of threonine, valine, serine, tyrosine, and tryptophan. In certain embodiments, the composition comprises two or more free amino acids selected from the group consisting of threonine, valine, tyrosine, tryptophan, aspartic acid, and serine. In certain embodiments, the composition comprises three or more free amino acids selected from the group consisting of threonine, valine, tyrosine, tryptophan, aspartic acid, and serine. In certain embodiments, the composition comprises four or more free amino acids selected from the group consisting of threonine, valine, tyrosine, tryptophan, aspartic acid, and serine. In certain embodiments, the composition comprises threonine, valine, tyrosine, tryptophan, and aspartic acid. In certain embodiments, the composition comprises the free amino acids of threonine, valine, tyrosine, tryptophan, and serine.

These amino acids, if present in the composition, may be present in, for example, the following concentrations: threonine at about 0.4 to about 1.5, about 0.7 to about 1.3, or about 0.9 to about 1.1 grams/liter; valine at about 0.7 to about 1.7, about 0.9 to about 1.5, or about 1.1 to about 1.3 grams/liter; serine at about 0.6 to about 1.6, about 0.8 to about 1.4, about 1.0 to about 1.2 grams/liter; tyrosine at about 0.05 to about 0.4, or about 0.1 to about 0.3 grams/liter; and tryptophan at about 1.1 to about 2.1, about 1.3 to about 1.9, or about 1.5 to about 1.7 grams/liter. In a certain embodiment, the therapeutic composition comprises threonine (about 1.0 grams/liter), valine (about 1.2 grams/liter), serine (about 1.1 grams/liter), tyrosine (about 0.2 grams/liter), and tryptophan (about 1.6 grams/liter). In one embodiment the composition does not include serine.

In a further embodiment, the composition comprises, or consists essentially of only one free amino acid selected from threonine, valine, tyrosine, and tryptophan, and/or derivatives thereof. In a further embodiment, the therapeutic composition comprises, or consists essentially of threonine as a free amino acid. The therapeutic composition may also comprise, or consist essentially of, valine as the free amino acid. In addition, the therapeutic composition comprises, or consists essentially of, tyrosine as a free amino acid. The therapeutic composition comprises, or consists essentially of, tryptophan as a free amino acid. Furthermore, the therapeutic composition comprises, or consists essentially of, aspartic acid as a free amino acid. In certain embodiments, the composition comprises serine as a free amino acid. In another embodiment, the composition may also comprise, or consist essentially of, two free amino acids selected from the group consisting of threonine, valine, serine, tyrosine, tryptophan, and aspartic acid, including the combination of threonine and valine, the combination of threonine and serine, the combination of threonine and tyrosine, the combination of threonine and tryptophan, the combination of valine and serine, the combination of valine and tyrosine, the combination of valine and tryptophan, the combination of serine and tyrosine, the combination of serine and tryptophan, the combination of tyrosine and aspartic acid, the combination of serine and aspartic acid, the combination of valine and aspartic acid, the combination of threonine and aspartic acid, the combination of tryptophan and aspartic acid, and the combination of tyrosine and tryptophan.

In another embodiment, the composition may comprise, or consist essentially of, three free amino acids selected from the group consisting of threonine, valine, serine, tyrosine, tryptophan and aspartic acid, including the combination of threonine, valine, and serine; the combination of threonine, valine, and tyrosine; the combination of threonine, valine, and tryptophan; the combination of threonine, serine, and tyrosine; the combination of threonine, serine, and tryptophan; the combination of threonine, tyrosine, and tryptophan; the combination of valine, serine, and tyrosine; the combination of valine, serine, and tryptophan; the combination of valine, tyrosine, and tryptophan; and the combination of serine, tyrosine, and tryptophan; the combination of threonine, valine, and aspartic acid, the combination of threonine, serine, and aspartic acid; the combination of threonine, tyrosine, and aspartic acid; the combination of threonine, tryptophan and aspartic acid; the combination of valine, serine, and aspartic acid; the combination of valine, tyrosine, and aspartic acid; the combination of valine, tryptophan and aspartic acid; the combination of serine, tyrosine and aspartic acid; the combination of serine, tryptophan and aspartic acid; the combination of tyrosine, tryptophan and aspartic acid.

In another embodiment, the composition may comprise, or consist essentially of, four free amino acids selected from the group consisting of threonine, valine, serine, tyrosine, tryptophan, and aspartic acid, including the combination of threonine, valine, serine, and tyrosine; the combination of threonine, valine, serine, and tryptophan; the combination of threonine, valine, tyrosine, and tryptophan; the combination of threonine, serine, tyrosine, and tryptophan; and the combination of valine, serine, tyrosine, and tryptophan; the combination of threonine, valine, serine, and aspartic acid; the combination of threonine, valine, tyrosine, and aspartic acid; the combination of threonine, valine, tryptophan, and aspartic acid; the combination of threonine, serine, tyrosine, and aspartic acid; the combination of threonine, serine, tryptophan, and aspartic acid; the combination of threonine, tyrosine, tryptophan, and aspartic acid; the combination of valine, serine, tyrosine, and aspartic acid; the combination of valine, serine, tryptophan, and aspartic acid; the combination of valine, tyrosine, tryptophan, and aspartic acid; the combination of serine, tyrosine, tryptophan, and aspartic acid.

In another embodiment, the composition may comprise, or consist essentially of, five free amino acids selected from the group consisting of threonine, valine, serine, tyrosine, tryptophan, and aspartic acid, including the combination of threonine, valine, serine, tyrosine and tryptophan; the combination of threonine, valine, serine, tyrosine, and aspartic acid; the combination of threonine, valine, serine, tryptophan, and aspartic acid; the combination of threonine, valine, tyrosine, tryptophan, and aspartic acid; the combination of threonine, serine, tyrosine, tryptophan, and aspartic acid.

In another embodiment, the composition may comprise, or consist essentially of, threonine, valine, serine, tyrosine, tryptophan, and aspartic acid as free amino acids.

In certain embodiments, the compositions may comprise natural amino acids or derivatives thereof that retain substantially the same, or better, activity in terms of enhancing the survival, proliferation, and/or development of stem cells and/or progenitor cells. In certain embodiments, the compositions may comprise natural amino acids or derivatives thereof that retain substantially the same, or better, activity in terms of wound healing, treating skin conditions (e.g., atopic dermatitis, psoriasis, bed sores, or condition related to the aging of skin), treating lung disorders (e.g., asthma), improving mucosal barrier function, and/or treating injury to GI mucosa in a subject in need thereof. The derivatives may be, for example, enantiomers, and include both the D- and L-forms of the amino acids. The derivatives may be, for example, iodotyrosine, or norvaline. Other amino acid derivatives include, for example, norleucine, ornithine, penicillamine, pyroglutamine derivatives, or other derivatives of alanine, asparagine, aspartic acid, cysteine, glutamic acid, glycine, isoleucine, leucine, lysine, methionine, proline, phenalalanine, serine, threonine, tryptophan, or valine. In certain embodiments, the amino acid derivatives are derivatives of threonine, valine, tyrosine, tryptophan, aspartic acid, or serine. Other amino acid derivatives include, but are not limited to, those that are synthesized by, for example, acylation, methylation, and/or halogenation of the amino acid. These include, for example, β-methyl amino acids, C-methyl amino acids, and N-methyl amino acids.

In some specific embodiments, the composition of the present disclosure does not comprise one or more amino acids selected from the group consisting of serine, lysine, glycine, isoleucine, and asparagine. Or, in certain embodiments, even if these amino acids are present in the composition, they are not present in an amount that would inhibit stem cell and/or progenitor cell proliferation and/or development.

In certain specific embodiments, the composition of the present disclosure does not include, or only comprises negligible amounts of, one of the free amino acids selected from the group consisting of serine, lysine, glycine, isoleucine, and asparagine. In further embodiments; the therapeutic composition does not include lysine as a free amino acid, or the therapeutic composition does not include glycine as a free amino acid; or the therapeutic composition does not include aspartic acid as a free amino acid; or the therapeutic composition does not include isoleucine as a free amino acid; or the therapeutic composition does not include asparagine as a free amino acid.

In some embodiments, the therapeutic composition does not include any two free amino acids selected from the group consisting of serine, lysine, glycine, isoleucine, and asparagine, including the combination of lysine and glycine, the combination of lysine and aspartic acid, the combination of lysine and isoleucine, the combination of lysine and asparagine, the combination of glycine and aspartic acid, the combination of glycine and isoleucine, the combination of glycine and asparagine, the combination of aspartic acid and isoleucine, the combination of aspartic acid and asparagine, and the combination of isoleucine and asparagine.

In other embodiments, the composition does not include any three free amino acids selected from the group consisting of serine, lysine, glycine, isoleucine, and asparagine, including the combination of lysine, glycine, and aspartic acid; the combination of lysine, glycine, and isoleucine; the combination of lysine, glycine, and asparagine; the combination of lysine, aspartic acid, and isoleucine; the combination of lysine, aspartic acid, and asparagine; the combination of lysine, isoleucine, and asparagine; the combination of glycine, aspartic acid, and isoleucine; the combination of glycine, aspartic acid, and asparagine; the combination of glycine, isoleucine, and asparagine; and the combination of aspartic acid, isoleucine, and asparagine.

In further embodiments, the composition does not include any four free amino acids selected from the group consisting of serine, lysine, glycine, aspartic acid, isoleucine, and asparagine, including the combination of lysine, glycine, aspartic acid, and isoleucine; the combination of lysine, glycine, aspartic acid, and asparagine; the combination of lysine, aspartic acid, isoleucine, and asparagine; the combination of lysine, glycine, isoleucine, and asparagine; and the combination of glycine, aspartic acid, isoleucine, and asparagine.

In a specific embodiment, the composition of the present disclosure does not include lysine, glycine, aspartic acid, isoleucine, and asparagine. In another specific embodiment, the composition does not include, or only includes negligible amounts of, serine, lysine, glycine, aspartic acid, isoleucine, and asparagine. In one embodiment, the composition does not include glutamine and/or methionine; and any di-, oligo-, or polypeptides or proteins that can be hydrolyzed into glutamine and/or methionine.

In certain specific embodiments, the therapeutic composition may comprise lysine, wherein the total concentration of lysine is less than 300 mg/l, 100 mg/l, 50 mg/l, 10 mg/l, 5 mg/l, 1 mg/l, 0.5 mg/l, or 0.01 mg/l. The therapeutic composition may also comprise aspartic acid, wherein the total concentration of aspartic acid is less than 300 mg/l, 100 mg/l, 50 mg/l, 10 mg/l, 5 mg/l, 1 mg/l, 0.5 mg/l, or 0.01 mg/l. The therapeutic composition may also comprise glycine, wherein the total concentration of glycine is less than 300 mg/l, 100 mg/l, 50 mg/l, 10 mg/l, 5 mg/l, 1 mg/l, 0.5 mg/l, or 0.01 mg/l. The therapeutic composition may further comprise isoleucine, wherein the total concentration of isoleucine is less than 300 mg/l, 100 mg/l, 50 mg/l, 10 mg/l, 5 mg/l, 1 mg/l, 0.5 mg/l, or 0.01 mg/l. The therapeutic composition may further comprise asparagine, wherein the total concentration of asparagine is less than 10 mg/l, 5 mg/l, 1 mg/l, 0.5 mg/l, or 0.01 mg/l.

In an alternative embodiment, the composition may comprise free amino acid glutamine, and, optionally, one or more glutamine-containing di peptides, wherein the total concentration of the free amino acid glutamine and the glutamine-containing dipeptide(s) is less than 300 mg/l, or any concentrations lower than 300 mg/l, such as 100 mg/l, 50 mg/l, 10 mg/l, 5 mg/l, 1 mg/l, 0.5 mg/l, or 0.01 mg/l. In certain embodiments, the composition may comprise free amino acid glutamine, and, optionally, one or more glutamine-containing peptides, wherein the total concentration of the free amino acid glutamine and the glutamine-containing peptide(s) is less than 300 mg/l, or any concentrations lower than 300 mg/l, such as 100 mg/l, 50 mg/l, 10 mg/l, 5 mg/l, 1 mg/l, 0.5 mg/l, or 0.01 mg/l.

In another alternative embodiment, the therapeutic composition may comprise free amino acid methionine, and, optionally, one or more methionine-containing dipeptides, wherein the total concentration of the free amino acid methionine and the methionine-containing dipeptide(s) is less than 300 mg/l, or any concentrations lower than 300 mg/l, such as 100 mg/l, 50 mg/l, 10 mg/l, 5 mg/l, 1 mg/l, 0.5 mg/l, or 0.01 mg/l. In certain embodiments, the composition may comprise free amino acid methionine, and, optionally, one or more methionine-containing dipeptides, wherein the total concentration of the free amino acid methionine and the methionine-containing peptide(s) is less than 300 mg/l, or any concentrations lower than 300 mg/l, such as 100 mg/l, 50 mg/l, 10 mg/l, 5 mg/l, 1 mg/l, 0.5 mg/l, or 0.01 mg/l.

In certain embodiments, the composition also comprises additives (e.g., nutrients, electrolytes, vitamins, minerals, etc.). In certain embodiments, the composition comprises iron or zinc. In certain embodiments, the therapeutic composition comprises one or more electrolytes selected from, for example, $Na^+$; $K^+$; $HCO_3^-$; $CO_3^{2-}$; $Ca^{2+}$; $Mg^{2+}$; $Fe^2$; $Cl^-$; phosphate ions, such as $H_2PO_4^-$, $HPO_4^{2-}$, and $PO_4^{3-}$; zinc; iodine; copper; iron; selenium; chromium; and molybdenum. In an alternative embodiment, the composition does not contain $HCO_3^-$ or $CO_3^{2-}$. In another alternative embodiment, the composition comprises $HCO_3^-$ and $CO_3^{2-}$ at a total concentration of less than 5 mg/l, or concentrations lower than 5 mg/l. In certain embodiments, the composition does not contain electrolytes. For example, in certain embodiments, the composition does not include one or more, or any, of $Na^+$; $K^+$; $HCO_3^-$; $CO3^{2-}$; $Ca^{2+}$; $Mg^{2+}$; $Fe^2$; $Cl^-$; phosphate ions, such as $H_2PO_4^-$, $HPO_4^{2-}$, and $PO_4^{3-}$; zinc; iodine; copper; iron; selenium; chromium; and molybdenum.

In certain embodiments, the composition does not contain one or more of the ingredients selected from oligo-, polysaccharides, and carbohydrates; oligo- or polypeptides, or proteins; lipids; small-, medium-, and/or long-chain fatty acids; and/or food containing one or more of the above-mentioned nutrients. In certain embodiments, the composition does not include glucose or sucrose.

In one embodiment, phosphate ions, such as $H_2PO_4^-$, $HPO_4^{2-}$, and $PO_4^{3-}$, are used to buffer the composition of the present disclosure. In one embodiment, the therapeutic composition uses $HCO_3^-$ or $CO_3^{2-}$ as a buffer. In another embodiment, the therapeutic composition does not use $HCO_3^-$ or $CO_3^{2-}$ as buffer.

In certain embodiments, the composition comprises: valine, threonine, tyrosine, electrolytes, Na+ (about 10 mmol to 60 mmol), and K+ (about 1 mmol to 20 mmol). In certain embodiments, the composition comprises a buffer.

Stem Cell and/or Progenitor Cell Therapies and Therapies for Wound Healing, Treating Skin Conditions Lung Disorders, Improving Mucosal Barrier Function, and/or Treating Injury to GI Mucosa Described herein are compositions of amino acids as therapies for treating GI, lung, and skin disorders. The present disclosure provides compositions and methods enhancing the survival, proliferation, and/or development of stem cells and/or progenitor cells. The present disclosure provides compositions and methods for treating a disease or conditions that is related to mucosal barrier function, e.g., wound healing, treating skin conditions (e.g., atopic dermatitis, psoriasis, bed sores, or condition related to the aging of skin), treating lung disorders (e.g., asthma), improving mucosal barrier function, and/or treating injury to GI mucosa in a subject in need thereof. The number of stem cells and/or progenitor cells can be increased by increasing survival, proliferation, and/or development of the cells. In one embodiment, the method comprises exposing the stem cells and/or the progenitor cells to a composition of the present disclosure. The stem cells and/or the progenitor cells can be exposed to the composition in culture, ex vivo, in situ, or in vivo, including after being administered, implanted/, or delivered into a subject.

The subject can be, for example, a human in which promoting the survival, proliferation and/or development of stem cells and/or progenitor cells is needed. The subject can be, for example, a human subject with a disease or condition in need of treatment. In addition to humans the animal can be of any species, including, but not limited to, mammalian species including, but not limited to, domesticated and laboratory animals such as dogs, cats, mice, rats, guinea pigs, and hamsters; livestock such as horses, cattle, pigs, sheep, goats, ducks, geese, and chickens; other primates such as apes, chimpanzees, orangutans, and monkeys; fish; amphibians such as frogs and salamanders; reptiles such as snakes and lizards; and other animals such as fox, camels, bears, antelopes, llamas, weasels, rabbits, mink, beavers, ermines, otters, sable, seals, coyotes, chinchillas, deer, muskrats, and possum.

In one embodiment, the methods lead to an increase in the survival, proliferation, and/or development of stem cells and/or the progenitor cells. In certain embodiments, the methods lead to an improvement in the condition of a subject with a disease or conditions that is related to mucosal barrier function, e.g., wounds, skin conditions (e.g., atopic dermatitis, psoriasis, bed sores, or condition related to the aging of skin), lung disorders (e.g., asthma), mucosal barrier function, and/or injury to GI mucosa.

In one embodiment, the method comprises introducing the composition according to the present invention to stem and/or progenitor cells in culture for promoting survival, proliferation, and/or development. The composition may thus be used to obtain enhanced quantities of the cells for use in treating various diseases and conditions.

In one embodiment, the present disclosure provides a method of improving therapeutic outcomes of implanted stem cells comprising administering a composition of the present disclosure in conjunction with stem cell implantation. The administration of the composition can be at, or proximate to, a target stem cell implantation site in a human or nonhuman animal. In certain embodiments, provided herein is a method for treating a disease or conditions that is related to mucosal barrier function, e.g., wound healing, treating skin conditions (e.g., atopic dermatitis, psoriasis, bed sores, or condition related to the aging of skin), treating lung disorders (e.g., asthma), improving mucosal barrier function, and/or treating injury to GI mucosa in a subject in need thereof, the method comprising administering a composition described herein to the subject in need thereof.

In one embodiment, recipients of administered stem and/or progenitor cells can be immunosuppressed, either through the use of immunosuppressive drugs such as cyclosporin, or through local immunosuppression strategies employing locally applied immunosuppressants, but such immunosuppression need not necessarily be a prerequisite in certain immunoprivileged tissues such as, for example, brain and eye tissues.

In certain embodiments, administered stem and/or progenitor cells are autologous in nature, i.e., prepared from the recipient's own tissue. In such instances, the progeny of stem cells can be generated from dissociated or isolated tissue and proliferated in vitro using the composition of the present disclosure. Upon suitable expansion of cell numbers, the cells can be harvested and readied for administration into the recipient's affected tissue.

In one embodiment, the present disclosure provides a method for promoting the proliferation and differentiation of stem cells in a subject in such need, wherein said method comprises: identifying a subject in such need, and administering, to the subject, an effective amount of a composition comprising, consisting essentially of, or consisting of one or more free amino acids selected from the group consisting of threonine, valine, tyrosine, tryptophan, aspartic acid and serine; and optionally, one or more pharmaceutically acceptable carriers, adjuvants and/or other active agents, wherein the composition has a total osmolarity from about 100 to about 280 mosm and a pH of about 2.5 to about 6.5. In certain embodiments, provided herein is a method for treating a disease or conditions that is related to mucosal barrier function, e.g., wound healing, treating skin conditions (e.g., atopic dermatitis, psoriasis, bed sores, or condition related to the aging of skin), treating lung disorders (e.g., asthma), improving mucosal barrier function, and/or treating injury to GI mucosa, wherein said method comprises: identifying a subject in such need, and administering, to the subject, an effective amount of a composition comprising, consisting essentially of, or consisting of one or more free amino acids selected from the group consisting of threonine, valine, tyrosine, tryptophan, aspartic acid and serine; and optionally, one or more pharmaceutically acceptable carriers, adjuvants and/or other active agents, wherein the composition has a total osmolarity from about 100 to about 280 mosm and a pH of about 2.5 to about 6.5.

In another embodiment, the compositions and methods of the present disclosure can be used for overcoming bone marrow suppression secondary to drugs, chemicals, and viral or bacterial infections of unknown cause.

In certain embodiments, the present disclosure can be used to promote the proliferation and development of stem cells and/or the progenitor cells in diseases and conditions including, but not limited to, malignancy; paneth cell deficiency; hypopituitarism; coeliac disease such as coeliac disease unresponsive to gluten-free diet; tropical sprue; radiation-associated ischemia; drug-induced villous atrophy, such as villous atrophy induced by neomycin and azathioprin, severe alimentary intolerance; congenital Crohn disease; autoimmune enteropathy; enterocolitis; hepatitis; intestinal cancer; intestinal lymphoma; type 1 diabetes; allergy; ocular conditions, such as cornea laceration; eosinophillic gastroenteritis; viral gastroenteritis, and immunodeficiency syndromes.

In some embodiments, the present disclosure can be used to promote the proliferation and differentiation of stem cells in viral, fungal, or bacterial infection-induced conditions and diseases, for example, viral, fungal, or bacterial infection-induced bone marrow suppression. For example, the compositions and methods can be used to treat a patient with a low platelet count caused by, for example, the Dengue virus.

The compositions described herein can also be used to treat, or ameliorate the symptoms of, for example, deficits caused by a neurodegenerative disease, traumatic injury, neurotoxic injury, ischemia, developmental disorders, disorders affecting vision, injuries or disease of the spinal cord, demyelinating diseases, autoimmune diseases, infections, inflammatory diseases, or corporal diseases.

In certain embodiments, implanted stem cells are capable of proliferating, migrating to an area of tissue damage, and/or differentiating in a tissue-specific manner and functioning in a manner that reduces the deficit.

In one embodiment, the method and composition according to the present disclosure is particularly useful for patients that are exposed to radiation, or receive radiation, chemo-, and/or proton therapy.

In another aspect, the present disclosure provides methods of treating injury to the GI tract (e.g., small intestine mucosa, esophagus, stomach, large intestines, etc.), genitourinary tract, or an organ with mucosal lining in a subject in need thereof, the method comprising administering to the subject a composition described here. In another aspect, the present disclosure provides methods of treating a condition related to the mucosal barrier in a subject in need thereof, the method comprising administering to the subject a composition described here.

The compositions of the present disclosure can be used in the treatment or amelioration of any diseases or conditions in need of proliferation and/or development of stem and/or progenitor cells. In a specific embodiment, the compositions and methods of the present disclosure can be used in the treatment or amelioration of radiation-induced injury to the small intestine by promoting the proliferation of stem cells. In another specific embodiment, the present disclosure can be used in the treatment or amelioration of injury to the small intestine caused by radiation therapy, particularly pelvic and abdominal radiation therapy. In a specific embodiment, the radiation therapy is for cancer treatment.

Additionally, the present disclosure can be used to promote proliferation of stem cells for the treatment or amelioration of injury to the small intestine caused by chemotherapeutic agents including, but not limited to, cisplatin, 5-fluorouracil (5-FU), hydroxyurea, etoposide, arabinoside, 6-mercaptopurine, 6-thioguanine, fludarabine, methothexate, steroids, and/or a combination thereof. Exemplary chemotherapeutic agents include, but are not limited to, anti-estrogens (e.g. tamoxifen, raloxifene, and megestrol), LHRH agonists (e.g. goscrclin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib ORESSAC®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVARC), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

In certain embodiments, the present disclosure can be used to promote the survival and proliferation of stem cells for the treatment or amelioration of diseases involving injury to the small intestine including, but not limited to, inflammatory bowel disease (IBD), ulcerative colitis, duodenal ulcers, Crohn's disease, and/or coeliac disease (also known as celiac disease). The present disclosure can be used in the treatment or amelioration of injury to the small intestine due to pathogenic infection, such as viral, bacterial, fungal, or other microbial infection.

In one embodiment, the stem cells and/or progenitor cells have been subjected to radiation prior to treatment with the composition of the present disclosure. In another embodiment, the stem cells and/or progenitor cells will be subjected to radiation after treatment with the composition of the present disclosure. The radiation may be administered to the cells, for example, 1 minute, 5 minutes, 30 minutes, 1 hour, 6 hours, 12 hours, 1 day, 5 days, 7 days, 14 days, 30 days, 60 days, 3 months, 6 months, 1 year, 2 years, or 3 years or more, before or after treatment of the cells with the composition described herein. The dose of radiation may be, for example, at least 1, 2, 3, 4, 5, 6, 7, 8, 9, 10, 15, 20, 25, 30, 35, 40, 45, 50, 55, 60, 65, 70, 80, 85, 90, 95, 100, 120, or 150 Gy.

In one embodiment, the present disclosure can be used in the context of bone marrow transplants. Bone marrow stem and/or progenitor cells can be treated in vivo or ex vivo with a composition of the present disclosure. Such treatment enhances the survival, proliferation, and/or development of the cells.

In another embodiment, the present disclosure can be used in the context of Prochymal, which is used in the management of acute graft-vs-host disease in children. It is an allogenic stem therapy based on mesenchymal stem cells (MSCs) derived from the bone marrow of adult donors. The survival, proliferation, and/or development of the MSCs can be enhanced by contacting them, either in vivo or ex vivo with the composition of the present disclosure.

In another embodiment, the compositions and methods of the present disclosure can be used in cardiac treatments. Stem-cell therapy for treatment of myocardial infarction often makes use of autologous bone-marrow stem cells; however, other types of adult stem cells may be used, such as adipose tissue-derived stem cells. In one embodiment, use of stem cell therapy results in cardiac tissue regeneration to reverse the tissue loss underlying the development of heart failure after cardiac injury.

In another embodiment, the compositions and methods of the present disclosure can be used in blood cell formation and expansion. Fully mature human red blood cells may be generated ex vivo by hematopoietic stem cells (HSCs), which are precursors of red blood cells. In this process, HSCs can be grown together with stromal cells, creating an environment that mimics the conditions of bone marrow, the natural site of red-blood-cell growth. In addition to using compositions of the present disclosure, erythropoietin, a growth factor, can be added, coaxing the stem cells to complete terminal differentiation into red blood cells. The compositions and methods can also be used to expand populations of red blood cells, white blood cells, and/or platelets to improve, for example, oxygen carrying capacity (such as for athletes), the immune system (including for treating immune-compromised subjects), and for improving clotting.

In another embodiment, cochlear hair can be re-grown using embryonic stem cells treated with the compositions of the present disclosure.

In another embodiment, stem cells treated according to the present disclosure can be used to treat blindness and vision impairment. In a specific embodiment, the compositions and methods are used to treat cornea laceration.

In another embodiment, the present disclosure can be used in the context of enhancing the success of tissue transplantations, including the transplantation of insulin-producing pancreatic beta cells. These cells can be prepared from, for example, embryonic stem cells that have been caused to differentiate into the beta cells. These cells may be treated in vivo or ex vivo with the compositions of the present disclosure.

In another aspect, the present disclosure provides methods of treating a wound and/or promoting wound healing in a subject in need thereof, the method comprising administering to the subject a composition described herein. In certain embodiments, the present disclosure provides methods of treating a wound in a subject in need thereof, the method comprising administering to the subject a composition described herein. In certain embodiments, the present disclosure provides methods of treating a wound or burn in a subject in need thereof, the method comprising administering to the subject a composition described herein. In certain embodiments, the present disclosure provides methods of treating a burn in a subject in need thereof, the method comprising administering to the subject a composition described herein. In certain embodiments, the wound is a partial thickness or full thickness wound. In certain embodiments, the burn is a partial thickness or full thickness burn.

The present disclosure can also be utilized in the context of wound healing. In an adult, wounded tissue is most often replaced by scar tissue, which is characterized by disorganized collagen structure, loss of hair follicles, and irregular vascular structure. In one embodiment, stem cell "seeds" are placed inside a tissue bed in a wound bed and allowing the stem cells to stimulate differentiation in the tissue bed cells. This method can be greatly enhanced by contacting the wound, with or without the addition of stem cells, with the composition of the present disclosure. In certain embodiments, the composition is applied to the skin. In certain embodiments, the composition is applied to stem cells and/or progenitor cells.

In other embodiments, the composition and methods described herein are useful for cosmetic applications where, for example, rejuvenation of the various layers of the skin and/or the underlying tissues is desired. This rejuvenation can be aided by, for example, the enhanced survival, proliferation, and/or development of stem cells and/or progenitor cells. This rejuvenation can be aided by, for example, by treating a disease or conditions that is related to mucosal barrier function, e.g., wounds, skin conditions (e.g., atopic dermatitis, psoriasis, bed sores, or condition related to the aging of skin), lung disorders (e.g., asthma), mucosal barrier function, and/or injury to GI mucosa.

In this embodiment, the methods of the present disclosure generally include the step of topically applying the compositions to the skin (e.g., epidermis) of the patient needing such treatment, wherein a therapeutically effective amount of such composition is applied. In one embodiment, the composition is applied to the face.

Advantageously, the present invention provides compositions and methods that combat the aging of skin, wherein combating the aging of skin can include, for example, treating the appearance of wrinkles, fine lines, and other forms of undesirable skin texture. By presenting the composition to the dermal and/or epidermal layer(s) of the skin, the form, strength, as well as function of the skin is enhanced. In certain embodiments, the composition and methods described herein are useful for beauty applications where, for example, rejuvenation of the various layers of the skin and/or the underlying tissues is desired.

In another aspect, the present disclosure provides methods of treating and/or preventing a skin condition (e.g., atopic dermatitis, psoriasis, or condition related to the aging of skin) in a subject in need thereof, the method comprising administering to the subject a composition described herein. In certain embodiments, the skin condition is atopic dermatitis, psoriasis, the aging of skin, a condition related to the aging of skin, or bed sores. In some embodiments, the skin condition is pruritus (itch), psoriasis, eczema, burns, or dermatitis. In certain embodiments, the skin condition is psoriasis. In certain embodiments, the skin condition is pruritus.

In certain embodiments, the compositions of the present disclosure comprise agents, in addition to the amino acids, that are useful in delaying, minimizing, or eliminating skin aging, wrinkling, and/or other histological changes typically associated with the intrinsic conditions (such as aging, menopause, acne, etc.) and extrinsic conditions (such as environmental pollution, wind, heat, sunlight, radiation, low humidity, harsh surfactants, etc.).

The present invention is useful for therapeutically and/or prophylactically improving visible and/or tactile characteristics in skin. For example, in one embodiment, the length, depth, and/or other dimension of lines and/or wrinkles are decreased.

In another aspect, the present disclosure provides methods of treating a lung disorder in a subject in need thereof, the method comprising administering to the subject a composition described herein. In certain embodiments, the composition is administered systemically or administered via inhalation. In another aspect, the present disclosure provides methods of improving lung function, lung healing, decreasing pneumonitis, decreasing airway resistance, and/or improving lung function in a subject in need thereof, the method comprising administering to the subject a composition described herein. In certain embodiments, the lung condition is a lung injury, pneumonitis, a condition associated with airway resistance, asthma, or inflammatory conditions of the lung. In certain embodiments, the composition is administered systemically or administered via inhalation.

In one embodiment, the composition applied to the skin or other tissue can further comprise collagen and/or hyaluronic acid (HA). In one embodiment, the HA is cross-linked HA. The composition can further comprise components such as, but not limited to, dermatologically acceptable carriers, desquamation agents, anti-acne agents, anti-wrinkle agents/anti-atrophy agents, vitamin B3 compounds, retinoids, hydroxyl acids, anti-oxidants/Radical scavengers, chelators, flavonoids, anti-inflammatory agents, anti-cellulite agents, topical anesthetics, tanning agents, skin lightening agents, skin soothing and skin healing agents, antimicrobial and antifungal agents, sunscreen agents, conditioning agents, structuring agents, thickening agent (including thickeners and gelling agents), composition preparation and preservatives. In this regard, international PCT application publication, WO 2008/089408 is incorporated herein, by reference, in its entirety.

The composition of the present disclosure can also be administered at a surgical site, including at a site of minimally invasive surgery, to improve healing and the surgical outcome.

Stem cells can also be used, in accordance with the present disclosure to treat infertility. In certain embodiments, a person is first diagnosed with a condition for which stem cell survival, proliferation and/or development would be beneficial. For example, the subject may be diagnosed with the condition and the composition of the subject application is then administration via a route, and in an amount, that results in stem cell survival, proliferation and/or development. Preferably, such administration then results in treatment (e.g., an improvement) of the condition.

Use of the Composition to Promote Intestinal Stem and/or Progenitor Cell Proliferation and/or Development, and to Treat a Disease or Conditions Related to Mucosal Barrier Function, Skin Conditions, Lung Disorders, Improve Mucosal Barrier Function, and Injury to GI Mucosa Described herein are uses of compositions of amino acids for treating GI, lung, and skin disorders. In specific embodiments, the composition of the invention can be used to induce intestinal epithelial cell proliferation resulting in increased villous height wherein the villi are comprised of mature, differentiated epithelial cells that lead to increased electrolyte and nutrient absorption. In one embodiment, the composition according to the present disclosure stimulates the proliferation and differentiation of stem cells and/or the progenitor cells as evidenced by increasing expression levels of NHE3 and SGLT1 in the brush border membrane. The composition therefore increases villous height and in addition increases the expression of key transporters for electrolyte and nutrient absorption.

Thus, in one embodiment, the present disclosure provides a pharmaceutical composition for preventing or treating gastrointestinal injury associated with the loss of small intestine epithelial cells, particularly in the villous region and the brush border, and/or for treating or ameliorating diseases or conditions associated with the alteration of absorptive capacity in the small intestine by promoting differentiation or proliferation of stem cells. These stem cells situated in the lower portion of the intestinal crypts, including fast cycling crypt base columnar cells (CBCs) and more quiescent "+4" cells above Paneth cells in mammals.

The present disclosure further provides methods for the treatment or amelioration of diseases or conditions associated with the loss of small intestine epithelial cells, particularly in the villous region and brush border, and diseases or conditions associated with the alteration of transport protein function in the small intestine epithelium by promoting the differentiation and proliferation of stem cells. The method comprises administering to a subject in need of such treatment, an effective amount of the composition of the present disclosure. In another aspect, the present disclosure provides methods for treating a disease or conditions that is related to mucosal barrier function, e.g., wound healing, treating skin conditions (e.g., atopic dermatitis, psoriasis, bed sores, or condition related to the aging of skin), treatinga lung disorders (e.g., asthma), a condition related to improving mucosal barrier function, and/or treating injury to GI mucosa in a subject in need thereof.

Formulations and Kits

The present disclosure provides for therapeutic or pharmaceutical compositions comprising a therapeutically effective amount of the subject composition and, optionally, one or more pharmaceutically acceptable carriers. The present disclosure provides for therapeutic, pharmaceutical, cosmetic, or nutritional compositions comprising a therapeutically effective amount of the subject composition and, optionally, one or more pharmaceutically acceptable carriers. Such pharmaceutical carriers can be liquids, such as water. The therapeutic composition can also comprise excipients, adjuvants, flavoring agents, etc. that facilitate processing of the active compounds into preparations that can be used pharmaceutically. Proper formulation is dependent upon the route of administration chosen. In an embodiment, the therapeutic composition and all ingredients contained therein are sterile. Examples of suitable pharmaceutical carriers are described in "Remington's Pharmaceutical Sciences" by E. W. Martin. Such compositions contain a therapeutically effective amount of the therapeutic composition, together with a suitable amount of carrier so as to provide the form for proper administration to the patient. The formulation should suit the enteral mode of administration.

In one embodiment, the administration of the composition can be systemic. Oral, intravenous, intra-arterial, subcutaneous, intra-peritoneal, intra-muscular, intra-ventricular, intranasal, transmucosal, subcutaneous, topical, rectal, and other modes of administration are all contemplated.

In one embodiment, for injection, the active ingredient can be formulated in aqueous solutions, preferably in physiologically compatible buffers. For transmucosal administration, penetrants appropriate to the barrier to be permeated are used in the formulation. Such penetrants are generally known in the art. For oral administration, the active ingredient can be combined with carriers suitable for inclusion into tablets, pills, dragees, capsules, liquids, gels, syrups, slurries, suspensions and the like. Formulations can also be prepared for use in inhalation therapy. For administration by inhalation, the composition can be delivered in the form of an aerosol spray presentation from pressurized packs or a nebuliser, with the use of a suitable propellant. The composition can also be administered via inhalation or other route as a powder.

Therapeutically effective doses of the presently described composition can be determined by one of skill in the art, with a goal of achieving a desired number of stem cells and/or precursor cells. An increase in the number of stem cells and precursor cells can be assessed using markers of these cells, or by determining an increase in the number of differentiated progeny of these cells. Method for measuring increased numbers of differentiated cells are known in the art. For example, immunohistochemistry, behavioral assessments or electrophysiological techniques can also be utilized. One of skill in the art can readily detect an increase in the number of cells of a specific phenotype.

In particular embodiments, the methods according to the present disclosure include administering the therapeutic composition by sustained-release systems. Suitable examples of sustained-release systems include suitable polymeric materials (such as, semi-permeable polymer matrices in the form of shaped articles, for example films, or microcapsules), suitable hydrophobic materials (for example as an emulsion in an acceptable oil) or ion exchange resins, and sparingly soluble derivatives (such as, for example, a sparingly soluble salt). Sustained-release compositions can be administered orally, parenterally, intracistemally, intraperitoneally, topically (as by powders, ointments, gels, drops or transdermal patch), or as an oral or nasal spray. Sustained-release matrices include polylactides (U.S. Pat. No. 3,773,919, EP 58,481), copolymers of L-glutamic acid and gamma-ethyl-L-glutamate (Sidman et al., Biopolymers 22:547-556, 1983, poly(2-hydroxyethyl methacrylate)); (Langer et al., J. Biomed. Mater. Res. 15:167-277, 1981; Langer, Chem. Tech. 12:98-105, 1982, ethylene vinyl acetate (Langer et al., Id.) or poly-D-(−)-3-hydroxybutyric acid (EP 133,988).

In one embodiment, implantable drug infusion devices may be used to provide patients with a constant and long-term dosage or infusion of a therapeutic composition. Such device can be categorized as either active or passive.

In one embodiment, polymers can be used for ion-controlled release. Various degradable and nondegradable polymeric matrices for use in controlled drug delivery are known in the art (Langer, Accounts Chem. Res. 26:537, 1993). For example, the block copolymer, polaxamer 407, hydroxyapatite, and liposomes.

The pharmaceutical composition of the present invention may be used either alone or in combination with one or more drugs known to be effective for treating diseases. The compositions can also be formulated in combination with at least one other agent, such as stabilizing or buffer compounds, which can be administered in any sterile, biocompatible pharmaceutical carrier, including, but not limited to, saline, buffered saline, dextrose, and water. In addition to the critical components of compositions discussed herein, cells or influencing factors, the compositions can contain suitable pharmaceutically acceptable carriers comprising excipients and auxiliaries that facilitate processing of the active compounds into preparations that can be used pharmaceutically. The composition may be prepared as a single-dosage form using a pharmaceutically acceptable carrier or excipient or may be contained in a multiple-dosage container.

In one embodiment, the composition may further contain other proliferation and/or differentiation inducing agents. The proliferation or differentiation inducing agent may be any one known as a proliferation or differentiation inducing agent. Examples include fibroblast growth factor (FGF), epidermal growth factor (EGF), and retinoic acid.

The composition may further contain other commonly used additives such as an anti-oxidant, a buffer, a bacteriostat, etc., and may be formulated into an injectable formulation such as aqueous solution, suspension, emulsion, etc. a pill, a capsule, a granule, a tablet, etc., by further adding a diluent, a dispersant, a surfactant, a binder, a lubricant, etc.

A food composition of the present invention may be contained in a health functional food.

The health functional food of the present invention may be prepared according to a method commonly employed in the art, and commonly used raw materials and ingredients may be added when preparing the health functional food.

When the composition of the present invention is included in a health functional food, the composition may be added alone or together with another health functional food or other food ingredient(s), according to commonly employed methods. The amount of the active ingredient may be determined appropriately depending on the purpose of use (e.g., prevention, health improvement, or therapeutic intervention). The food composition may further comprise, for example, a pre-biotic or pro-biotic substance.

The kind of food is not limited. Examples of the food to which the composition can be added include meat, sausage, bread, chocolate, candy, snack, confectionery, pizza, ramen, other noodles, gum, dairy products including ice cream, soup, beverage, tea, drink, alcoholic beverage, vitamin complex, etc.

Also encompassed by the disclosure are kits (e.g., pharmaceutical, therapeutic, cosmetic, or nutritional packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a composition described herein. In certain embodiments, the kits are useful for treating a disorder (e.g., GI, lung, and skin disorders) in a subject in need thereof. In certain embodiments, the kits are useful for preventing a disorder (e.g., GI, lung, and skin disorders) in a subject in need thereof.

In certain embodiments, a kit described herein further includes instructions for using the composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating and/or preventing a disorder (e.g., GI, lung, and skin disorders) in a subject in need thereof. A kit described herein may include one or more additional pharmaceutical or other agents described herein as a separate composition.

Methods of Administration

In one embodiment, the present disclosure involves the administration of the composition according to the present disclosure to a subject and further administering stem and/or progenitor cells to the subject. The composition is administered at a locus in said subject so as to allow contact with the cells. This may be at the same location, proximate to the location or distal to the location of where stem cells are administered.

Stem and/or progenitor cells may be administered by, for example, injecting one or a plurality of cells with a syringe, inserting the stem cells with a catheter or surgically implanting the stem cells. In certain embodiments, the stem cells are administered into a body cavity fluidly connected to a target tissue. In certain preferred embodiments, the body cavity is a brain ventricle. In other embodiments, the cells are inserted using a syringe or catheter, or surgically implanted directly at the target tissue site. In other embodiments, the stem and/or progenitor cells are administered parenterally. Parenteral administration is defined as administration via a route that bypasses the gastrointestinal tract. Parenteral administration includes intraventricular administration.

Generally compositions can be administered by any of a number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Factors can be administered at the same location as administered stem cells. Administration of influencing factors and stem cells can be conducted simultaneously, or one prior to the other, and at the same or different locations so long as the relative locations and timing allow for the factors to influence the stem and/or progenitor cells.

For instance, by using "consisting essentially of," the therapeutic composition does not contain any unspecified ingredients including, but not limited to, free amino acids, di-, oligo-, or polypeptides or proteins; and mono-, di-, oligo-, polysaccharides, and carbohydrates that have a direct beneficial or adverse therapeutic effect on promoting stem cell development. Also, by using the term "consisting essentially of," the compositing may comprise substances that do not have therapeutic effects on promoting stem cell development; such ingredients include carriers, excipients, adjuvants, flavoring agents, etc. that do not affect the promotion and/or development of stem cells.

It should be understood that the examples and embodiments described herein are for illustrative purposes only and that various modifications or changes in light thereof will be suggested to persons skilled in the art and are to be included within the spirit and purview of this application.

EXAMPLES

Materials and Methods

Animal model: Eight-week-old, male, NIH Swiss mice were fed a normal diet and housed at 4 mice per cage. The mice were irradiated using a Gammacell 40 Exactor Low-Dose Research Irradiator (Best Theratronics, Ottawa, Ontario) housing two cesium-137 sources in a parallel and opposed geometry to deliver isotropic irradiation with a dose uniformity within ±3%. Mice received a single fraction of TBI at a dose rate of 0.9 Gy/minute. Mice were secured in the middle of the irradiation chamber with a plastic jig that allowed 5 mice to be irradiated simultaneously. Mice treated with the formulation were given AA-ORS by gastric gavage once daily (0.3 ml/mouse). Control groups were given normal saline. The amino acid formulation was given as a supportive therapy and was not part of replacement therapy. Mice fasted for 8 hours prior to gavage. Animals were humanely euthanized through $CO_2$ inhalation followed by cervical dislocation (per the AVMA Guidelines for the Euthanasia of Animals) 6 days after irradiation when peak anion secretion occurs. Toxicity was predominantly due to acute GI syndrome and only minimally perturbed by bone marrow syndrome.[18] Following exsanguination, the ileal mucosa was obtained as previously described.[18,20] All experiments were approved by the University of Florida Institutional Animal Care and Use Committee (IACUC) and carried out in accordance with IACUC protocol #3875.

Crypt count and villus length measurements: Paraffin sections (5 µm) were obtained from intestinal segments oriented such that the sections were cut perpendicular to the long axis of the intestine. Crypts per circumference were counted, and villus length was measured from 10 sections obtained from the ileum. For determination of the cell survival curve parameters, the crypt counts were normalized and analyzed using the classical method.[21] AA-ORS treatment was given for a period of 6 days. Normal saline was used as a control.

Cell proliferation and crypt-to-villus migration assay: Incorporation of 5-ethynyl-2'-deoxyuridine (EdU, a thymidine analogue) into cellular DNA and the subsequent reaction of the EdU with a fluorescent azide in a copper-catalyzed reaction were used to study cell proliferation in the crypt cell region. Mice were injected with 0.5 mg of EdU in 150 ml of PBS (16. 7 mg/Kg) to assess mitotic activity in the crypt cells (these studies reveal S-phase in the crypts) and euthanized at 24, 48, and 72 hours after injection. Paraffin sections from the mouse ileum were prepared, and incorporated EdU (Thermo Fisher Scientific catalog #A10044) was visualized following the manufacturer's instructions (Alexa 647 imaging kit, catalog #C 10340). The sections were then mounted in fluorescent mounting media with DAPI (VectaShield, Cat #H-1200). Cells were scored per entire crypt and villus unit. At least 60 crypts and corresponding villi were analyzed per mouse. EdU-labeled cells were normalized to the total cell number per crypt or villus. Positively stained enterocytes are shown migrating from the base of the crypt to the tip of the villus.

Flux studies for sodium and chloride absorption: Stripped ileal sheets were mounted in between 2 halves of an Ussing chamber with 0.3 $cm^2$ of exposed surface area (P2304, Physiologic Instruments, San Diego, Calif., USA). The Ringer solution contained ($mmol.^{-1}$) $Na^+$ 140, $Cl^-$ 119.8, $K^+$ 5.2, $HPO_4^-$ 2.4, $H_2PO_4^-$ 0.4, $Mg^{2+}$ 1.2, $Ca^{2+}$ 1.2, and $HCO_3^-$ 25, was bubbled with 95% $O_2$ and 5% $CO_2$ bilaterally, and was maintained at 37° C. After the tissues were allowed to stabilize for 45 minutes, the basal short-circuit current ($I_{sc}$), expressed as $\mu eq \cdot h^{-1} \cdot cm^{-2}$, and conductance (G), expressed as $mS \cdot cm^{-2}$, were recorded using a computer-controlled voltage/current clamp device (VCC MC-8, Physiologic Instruments), as previously described.[18,20] For flux studies, radioisotopes of sodium ($^{22}Na$) and chloride ($^{36}Cl$) were used to study sodium and chloride fluxes across the ileal mucosa, as previously described.[18,20,22] Na activity was measured using a gamma counter (Wizard 2, 2480 Automatic Gamma Counter, Perkin Elmer, USA), while $^{36}Cl$ was measured using a liquid scintillation counter (LS 6500 Multipurpose Scintillation Counter, Beckman Coulter, Inc., Brea, Calif., USA).

Real-time quantitative polymerase chain reaction (PCR): RNA from intestinal tissue samples of nonirradiated and irradiated mice (0 Gy, 5 Gy, and 7 Gy) was extracted using the TRIZOL method. C-DNA was prepared with a c-DNA kit (iScript™ Select cDNA Synthesis Kit, Bio-Rad, Hercules, Calif.); semi-quantitative and real-time PCR was performed using specific oligonucleotide primers for caspase3, Lgr5, sgltl, and BMI1. c-DNA (2 µL) was added to 25 µt of PCR mixture for semi-quantitative PCR, and 20 µL of SyBr green mixture was added for quantitative PCR; 30 cycles of PCR (or more as indicated in Results) were carried out using a Veriti Thermal Cycler (Thermo Fisher Scientific, Waltham, Mass.) for semi-quantitative PCR and a CFX Connect Real-time System Cycler (Bio-Rad) for real-time PCR. One cycle consisted of 30 sec at 94° C. for denaturation, 60 sec for annealing, and 90 sec at 72° C. for extension. Amplicons were resolved by agarose gel electrophoresis and detected by ethidium bromide staining. CFX Manager™ Software (Bio-Rad) was used for real-time analysis. Standardization used the delta-delta Ct (DDCt) method. Briefly, DCt=Ct (target gene-treated)−Ct (ref gene-treated) and DCt=Ct (target gene-control)−Ct (ref gene-control). Therefore, DDCt=DCt (treated)−Ct (control). Fold change was calculated from the formula $2^{(-DDQ)}$.

Western Blot: Total cell lysate from nonirradiated and irradiated AA-ORS-treated or saline-treated mice was prepared in ice-cold RIPA buffer [50 mmol/L Tris-HCl (pH 7.4), 150 mmol/L NaCl, 1% IGEP AL, 1 mmol/L EDTA, 0.25% sodium deoxycholate, 1 mmol/L sodium fluoride, 1 mmol/L sodium orthovanadate, 0.5 mmol/L PMSF, 10 µg/mL aprotinin, 10 µg/mL leupeptin]. The protein concentration in each extract was determined by BCA assay (Sigma, St. Louis, Mo.). Cell extracts were subjected to sodium dodecyl sulfate polyacrylamide gel electrophoresis (SDS-PAGE); proteins were transferred to polyvinylidene difluoride (PVDF) membranes and probed with primary antibodies that detect Lgr5, SGL Tl, Bmi 1, caspase 3, p-ERK, and total ERK. Signals were detected with Odyssey CLX from LI-COR. Reversible Ponsceau S stain (Cat #786-575, G Biosciences) was used, according to the manufacturer's instructions, to check equal loading of gels. The abundance of the protein of interest was normalized to the total amount of protein in each lane. This technique minimized variations associated with comparing protein density to a single protein.

Immunohistochemical identification of the nuclear proteins PCNA and Ki-67, and the stem cellspecific membrane protein Lgr5 was performed using polyclonal rabbit antimouse GPCR (Lgr5) (Abeam Cat #ab75732), Ki-67 (Abeam Cat #ab15580) and PCNA (Abeam Cat #ab 18197) antibodies. A rabbit specific ABC detection kit (Abeam Cat #ab64261) was used to visualize the expression of the protein according to the manufacture's instruction. Briefly, formalin-fixed, paraffin-embedded full-thickness ileum samples were cut into 4 µm thick cross-sections, mounted on Superfrost Plus glass slides, de-paraffinized and rehydrated. For antigen retrieval heat pretreatment was applied using a pressure cooker (125° C. for 30 sec, and 90° C. for 10 sec) and retrieval buffer; Deloaker RTU Buffer (Biocare Medical Cat #RV1000MMRTU) at pH 6.0. After quenching endogenous peroxidase and blocking nonspecific bindings, sections were incubated with primary antibody diluted in PBS (Lgr5—1:100, Ki-67—1:1000, PCNA—1:4000, for 2 hours; 15 min; and 2 hours respectively at room temperature). PBS was used as a negative control. Tissues were then incubated with biotinylated goat anti-rabbit secondary antibody for 10 minutes. After incubation with streptavidin peroxidase, the desired stain intensity was obtained with Di-amino-benzidine by visualizing under the microscope. Sections were counterstained with Mayer's hematoxylin (Electron Microscopic Sciences (EMS) Cat #26043-05), dehydrated and mounted in Permount mounting medium (Fisher Scientific Cat #SP15-100). Slides were evaluated by light microscopy using a 20× objective for PCNA and Ki-67, and a 40× objective with oil immersion for Lgr5. The number of positive-brown cells were counted from 50 crypts per group and analyzed.

Statistics: Results are presented as mean±standard error of mean (S.E.M). Statistical analysis was performed in 2 steps: 1) overall difference was tested using analysis of variance (ANOVA) (or its non-parametric equivalent Kruskal-Wallis); and 2) Bonferroni-adjusted Pvalues were computed for all pair-wise comparisons.

Figure 1B:
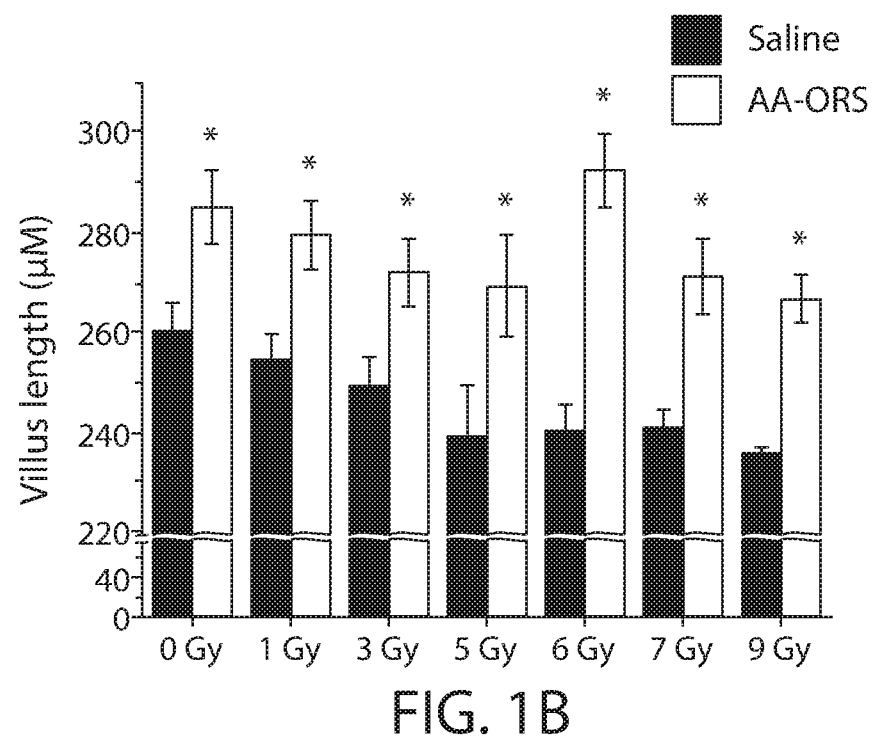

Example 1—AA-ORS Increased Crypt Count and Villus Length in Intestinal Tissues from Irradiated Mice The intestinal tissues of irradiated mice (5-15 Gy) treated with AA-ORS exhibited a significant increase in crypt count per circumference (N). As crypts are formed by regenerative units, these results indicate an increased number of progenitor epithelial cells. Similarly, villus length significantly increased across all radiation doses with AA-ORS treatment when compared to saline treatment (FIG. 1B). This is consistent with increased progenitor proliferation and/or longer survival of epithelial cells before natural sloughing.

The crypt survival curve was modeled using a single-hit, multi-target cell survival model to assess the biological effect. Without constraining constant cell sensitivity, the N values were 10.4±0.2 and 5.3±0.1 (P<0.001), indicating a near doubling of progenitor units per circumference from a control. When a constant Do (4.8±0.1 Gy) was constrained, the difference remained significant at 8.8±0.4 to 6.1±0.3 (P<0.001). The quasi-threshold dose (Dq) values, a composite measure of crypt tolerance of radiation, were 10.5±0.5 Gy for AA-ORS-treated mice and 8.8±0.4 Gy for saline-treated mice (P<0.01).

The AA-ORS group, as compared to the saline group, had a "broad shoulder" in the low radiation dose region, suggesting an increased number of progenitors per bowel circumference (less senescence) (FIG. 1A).

As expected, the terminal portion followed an exponential relationship. Since 5 Gy was the lowest radiation dose at which a significant increase in both crypt count and villus height occurred, all subsequent studies were undertaken in 0 and 5 Gy irradiated mice.

It was found that increased weight gain and survival could be secondary to increased crypt number and villus height that then increased the surface area of absorption. It was have demonstrated that crypt number and villus height increased with AA-ORS treatment beginning 6 days after irradiation. Using the single-hit, multi-target model for crypt survival, it was found that the number of crypt progenitor units per ileal circumference (N) increased significantly (P<0.001) without a change in Do (4.8±0.1 Gy) (FIG. 1A). The Dq values improved the equivalent to an increased radiation tolerance of 1.7 Gy with AA-ORS treatment, indicating improved crypt survival. The crypt survival studies suggested an increase in progenitor units or stem cells per crypt. Thus, the effect of irradiation and AA-ORS on stem cell number was examined using antibodies specific to intestinal stem cell markers and migration of the daughter cells into the villus secondary to proliferation by EdU incorporation.[14-16]

Example 2—AA-ORS Promotes Intestinal Epithelial Cell Migration

Ileal sections from irradiated mice treated with AA-ORS showed an increased crypt count. With the continuous renewal of villus epithelial cells, there is also a continuous migration of cells along the crypt-villus axis.[23] As the cells move along the villus, the epithelial cells undergo further maturation and differentiation and then migrate into the tip of the villi where they are shed by anoikis.[24] Cell proliferation was studied using EdU incorporation.

Figure 2A:
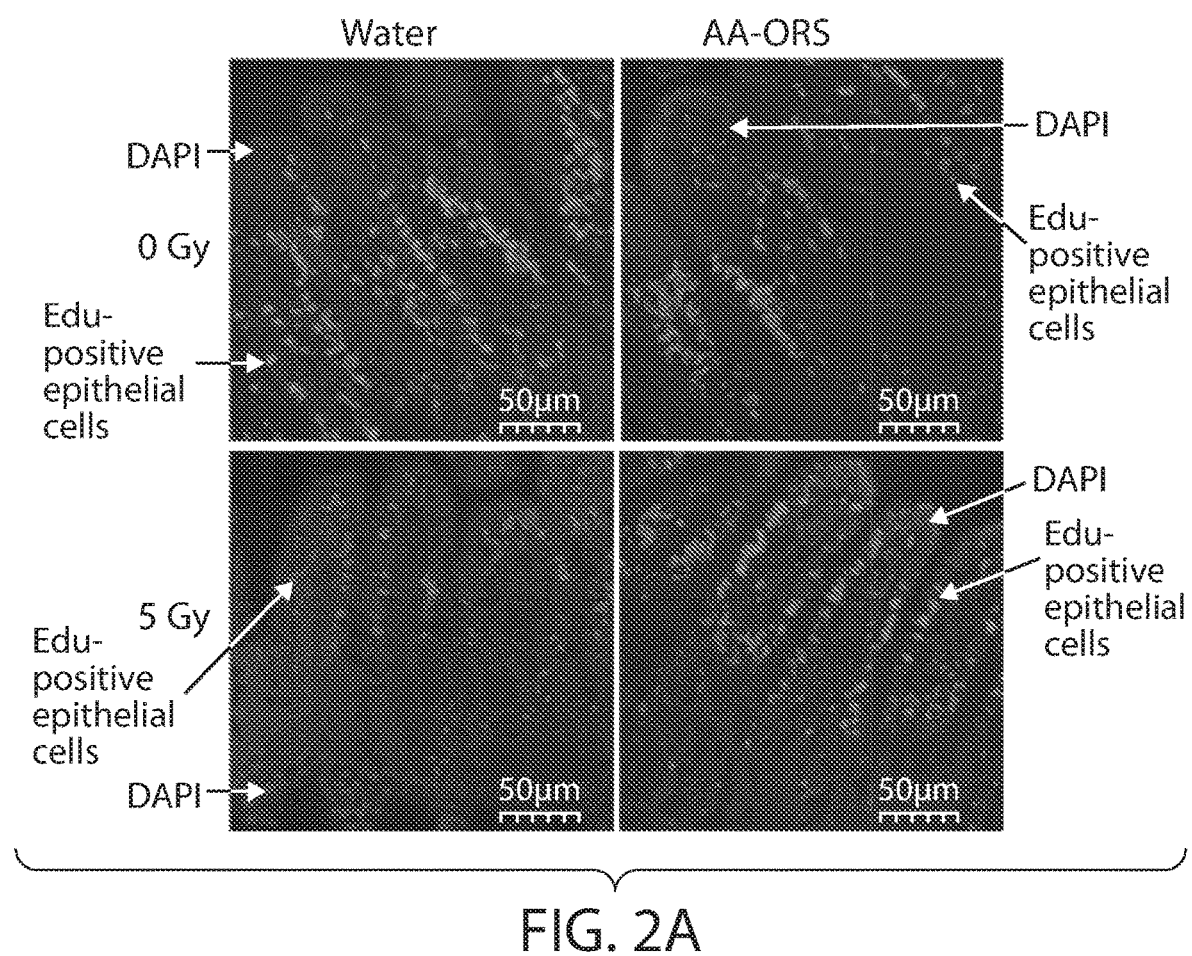
FIG. 2A shows confocal microscopy of longitudinal ileal section with prominently stained epithelial cells along the villus length. Paraffin embedded tissues at 5-μm thickness were used. Cell nuclei were stained with DAPI (dark gray), and Edu-positive epithelial cells were stained light gray. Image Pro Plus software was used for measurements of distance migrated by the Edu-positive cells along the villus height. Bar-50 μm. A minimum of five well-oriented villi were counted per tissue section, and the results were averaged. Edu-positive cells were seen all the way to the tip of the villus in 5 Gy irradiated tissues but not in AA-ORS-treated mice.
Figure 2B:
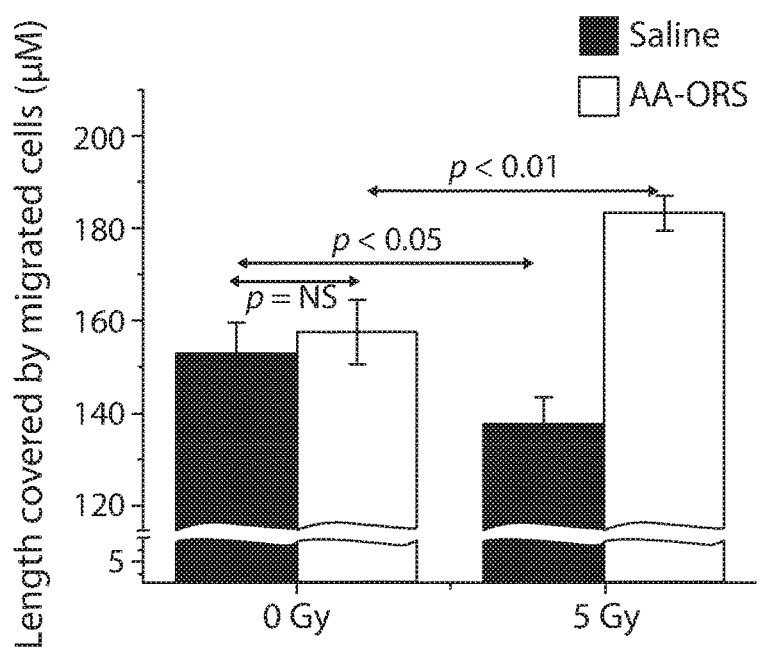
FIG. 2B shows EdU-positive cell migration distance measured at 72 hours. The 5 Gy irradiated saline-treated mice had a significant decrease in cell migration distance (black bar) compared to 0 Gy; the AA-ORS-treated mice had increased migration distance when compared to non-irradiated and irradiated saline-treated. Values are means±SEM for 6 mice per group.

Cells were found to migrate from the crypt base to the villus tip in ~72 hours. Ileal sections from nonirradiated mice showed that cells (EdU-incorporated) reached the villus tip at different times (75±0.9 hours; n=10 mice) with a mean of 76.5 hours. AA-ORS treatment for 6 days did not lead to a significant difference in the length covered by the migrated cells between 0 and 5 Gy irradiated mice (153.5±7 mm vs 158.1±7 mm; n=10 mice). However, AA-ORS treatment for 6 days led to a significant difference in 5 Gy irradiated mice (15 8.1±7 mm vs 183.1±4 mm; p<0.01, n=10 mice) (FIGS. 2A & B). These studies show that AA-ORS increases proliferation and is responsible for the length covered.

Example 3—AA-ORS Increased Sodium and Chloride Absorption

AA-ORS increased villus height and proliferation in the crypt cell region. To determine if the increased villus height resulted in functionally mature and differentiated villus epithelial cells, isotope flux studies were undertaken to determine sodium and chloride absorption.

Figure 3A:
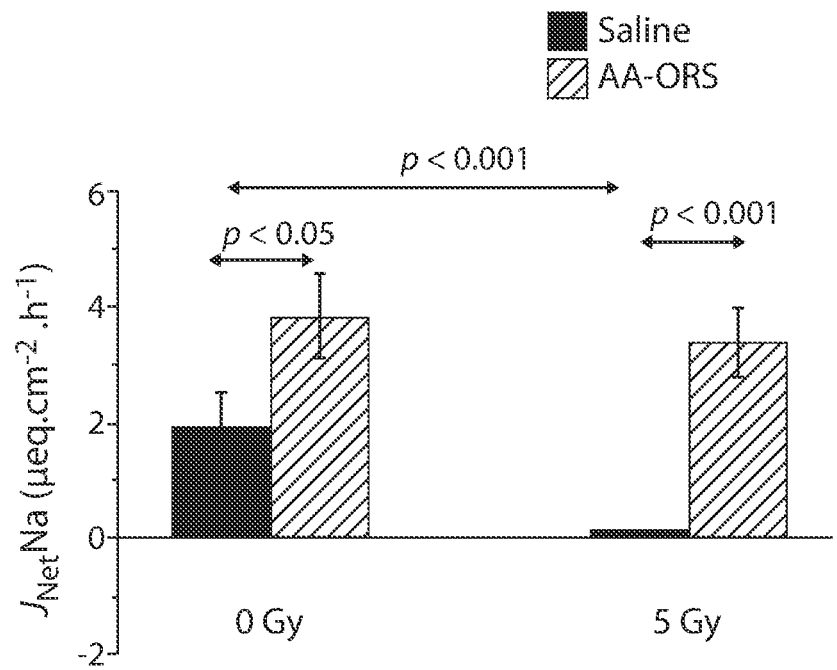
FIGS. 3A-3B show Ussing chamber flux studies using $^{22}$Na and $^{36}$Cl showing the effect of AA-ORS on sodium and chloride absorption. AA-ORS increased net sodium (JnetNa) and chloride ($J_{net}Cl$) absorption in 0 Gy and 5 Gy irradiated tissues (n=8).
Figure 3B:
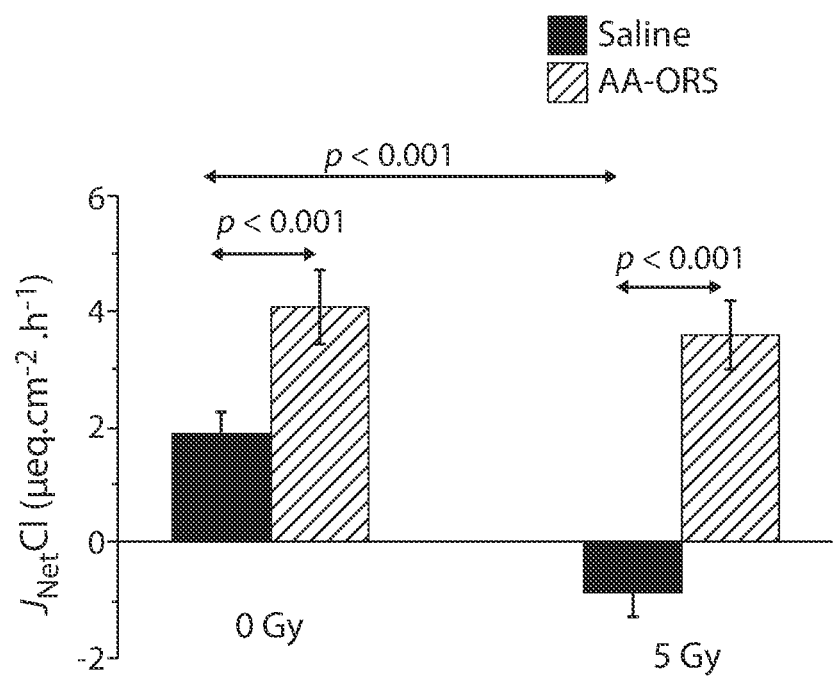

Non-irradiated mice had a net sodium absorption ($J_{Net}Na$) of 1.9±0.6 ueq·cm$^{2}$·h$^{-1}$ and a net chloride absorption ($J_{Net}Cl$) of 1.9±0.4 ueq·cm$^{2}$·h$^{-1}$ (FIGS. 3A-3B). The ileum of 5 Gy irradiated mice had a decrease in $J_{Net}Na$ (1.9±0.6 µeq·cm$^{2}$·h$^{-1}$ vs 0.1±0.0 µeq·cm$^{2}$·h$^{-1}$; P<0.001, n=8) and $J_{Net}Cl$ (1.9±0.4 µeq·cm$^{2}$·h$^{-1}$ vs −0.9±0.4 µeq·cm$^{2}$·h$^{-1}$). AA-ORS treatment led to a significant increase in net sodium absorption in the ileum of 0 Gy (3.9±0.7 ueq·cm$^{2}$·h$^{-1}$; p<0.05, n=8) and 5 Gy (3.4±0.7 ueq·cm$^{2}$·h$^{-1}$; p<0.001, n=8) mice (FIG. 3A). Similarly, AA-ORS treatment led to increased chloride absorption in the ileum of 0 Gy (4.1±0.6 ueq·cm$^{2}$·h$^{-1}$; p<0.05, n=8) and 5 Gy (3.6±0.6 ueq·cm$^{2}$·h$^{-1}$; p<0.001, n=8) mice (FIG. 3B).

These studies suggest that AA-ORS-induced increase in villi heights are functional, by showing that electrolyte absorptive capacity and sodium-coupled glucose absorption are increased, which is a function of mature and differentiated villus epithelial cells.

Figure 3C:
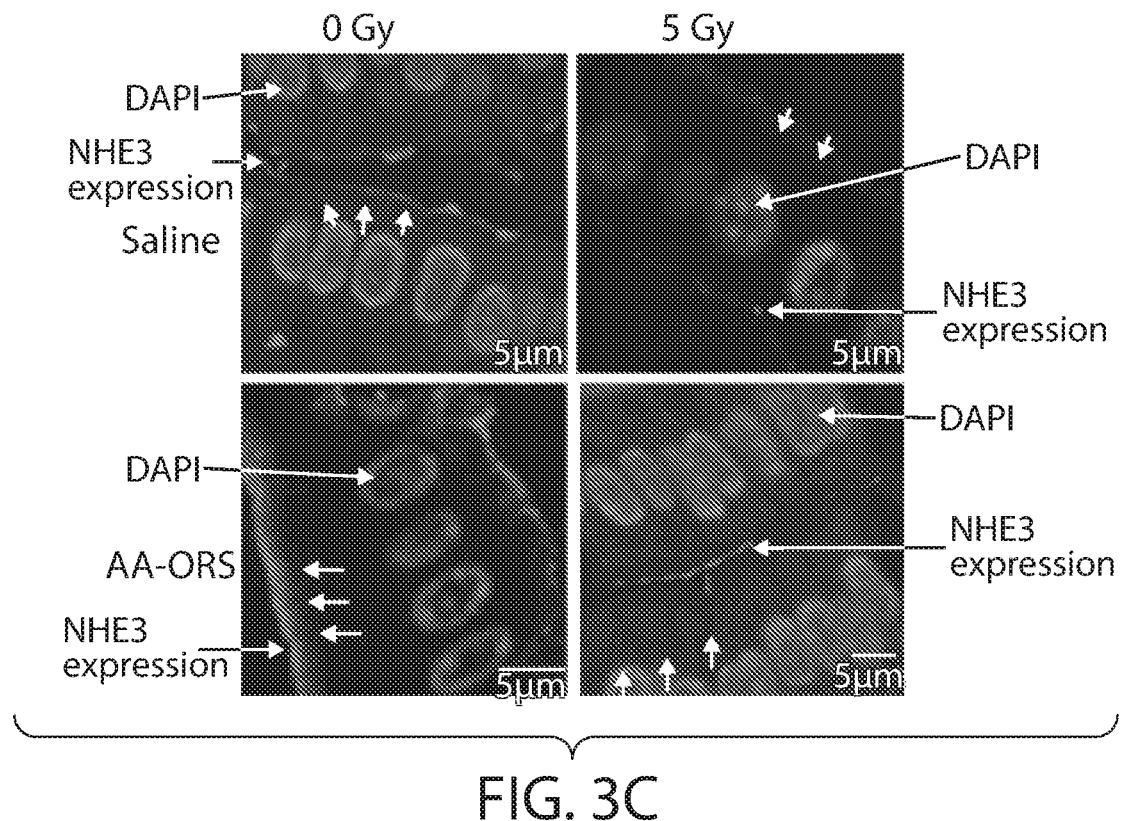
FIG. 3C is immunohistochemistry showing a magnified view of NHE3 expression (light gray) along the brush border membrane (BBM) of villus epithelial cells (white arrows). Paraffin-embedded tissues at 5-μm thickness were used. Cell nuclei were stained with DAPI (dark gray). A minimum of five well-oriented villi were used.
Figure 3D:
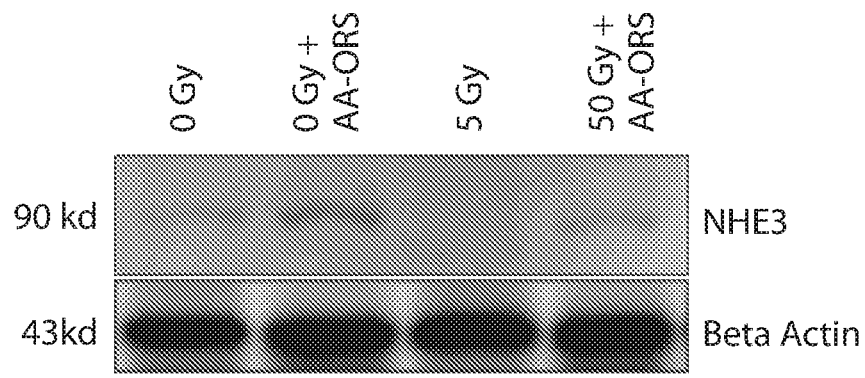
FIG. 3D shows a Western blot analysis for NHE3 protein.
Figure 3E:
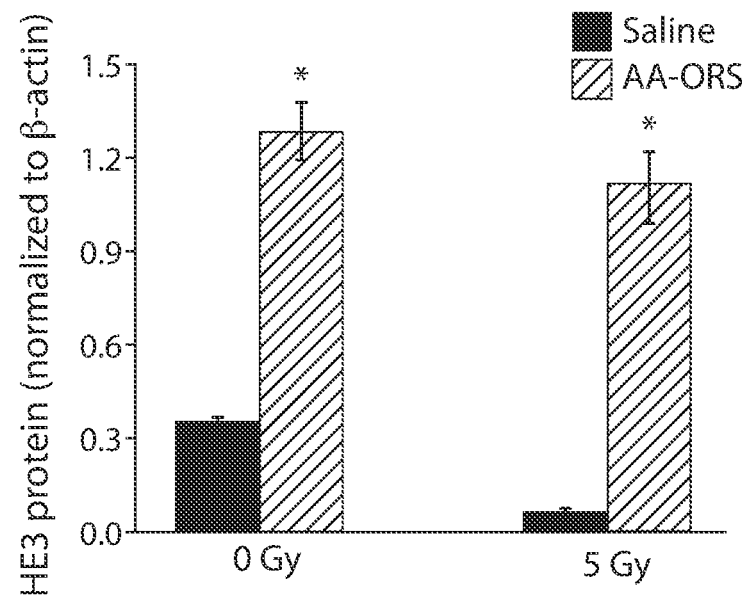
FIG. 3E shows a graphical representation of NHE3 protein density in intestinal tissues from mice treated with saline (black bars) or AA-ORS (hatched bars) following 0 or 5 Gy irradiation. Immunoblots were repeated four times. Values are means±SEM from n=4; * indicates statistically significant difference (P<0.05) from saline-treated animals.
Figure 3F:
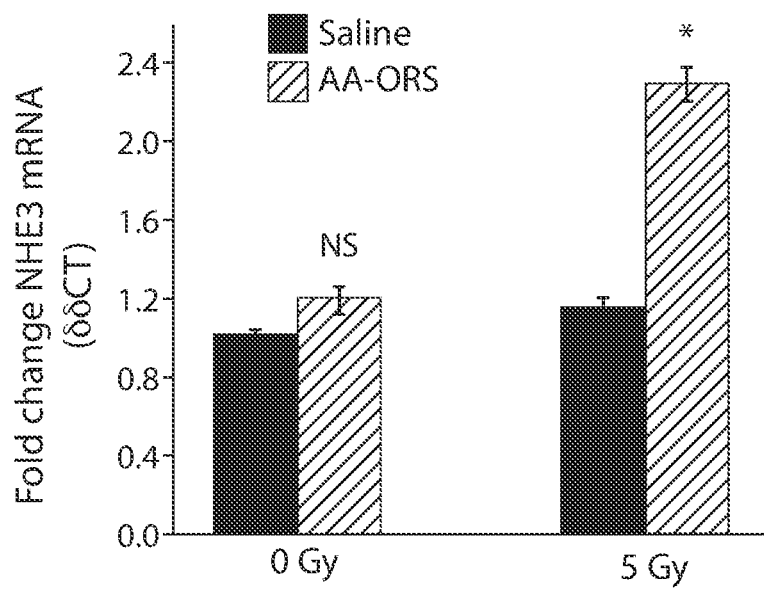
FIG. 3F shows NHE3 transcript levels in intestinal tissues from mice treated with saline (black bars) or AA-ORS (hatched bars) following 0 or 5 Gy irradiation. Values are means±SEM from n=6; * indicates statistically significant difference (P<0.05) from saline-treated animals. Saline or AA-ORS was given for 6 days.

Immunohistochemistry for the NHE3 protein showed NHE3 antibody recognition along the brush border region of villus epithelial cells (FIG. 3C). Villus cells from 5 Gy irradiated animals showed little or no expression along the brush border membrane. Treatment with AA-ORS increased NHE protein expression along the border region in epithelial cells from 0 Gy and 5 Gy irradiated mice (FIG. 3C). Western blot analysis showed increased NHE3 protein expression in the intestinal tissues of AA-ORS-treated mice irradiated at 0 Gy (3.5-fold) and 5 Gy (15.5-fold) compared to saline-treated irradiated mice (FIG. 3D-3E). These studies suggest an increase in NHE3 protein in the brush border membrane of the villus epithelial cells. To determine if the increase in NHE3 protein resulted from an increase in NHE3 mRNA, its levels in intestinal tissues were determined using qPCR (FIG. 3F). Unlike NHE3 protein levels, NHE3 mRNA levels were only significantly different at 5 Gy when compared to saline-treated 5 Gy irradiated mice. Protein levels did not correlate well with the changes in NHE3 mRNA levels and similar observation has been reported previously.

Example 4—AA-ORS Increased Glucose-Stimulated Sodium Absorption

Glucose stimulates sodium absorption via a specific transporter located in the apical membrane of mature and differentiated epithelial cells located in the villus. To determine if the AA-ORS-induced increase in villus height resulted in improved glucose absorption, the glucose-stimulated sodium absorption using $^{22}$Na flux studies were assessed.

Figure 4A:
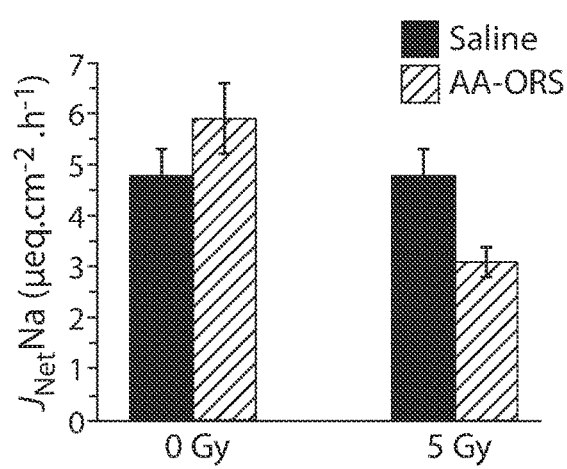
FIGS. 4A-4D show a glucose-stimulated sodium absorption and SGLT1 protein levels: (4A) Ussing chamber flux studies using 22Na showing the effect of AA-ORS on glucose-coupled sodium absorption. AA-ORS treatment increased JnetNa absorption in 5 Gy irradiated tissues (n=8). (4B) Western blot analysis for SGLT1 protein and beta-galactosidase showed increased protein levels with AA-ORS treatment in villus cells from 0 Gy and 5 Gy mice. Immunoblots were repeated four times. (4C) Normalized SGLT1 protein levels for western analysis. Significant difference in SGLT1 protein levels was observed in 5 Gy irradiated mice treated with AA-ORS when compared to 5 Gy mice. (4D) SGLT1 transcript levels in intestinal tissues from mice treated with saline (black bars) or AA-ORS (hatched bars) following 0 or 5 Gy irradiation. Values are means±SEM from n=6; * indicates statistically significant difference (P<0.05) from saline-treated animals. Saline or AA-ORS was given for 6 days.
Figure 4B:
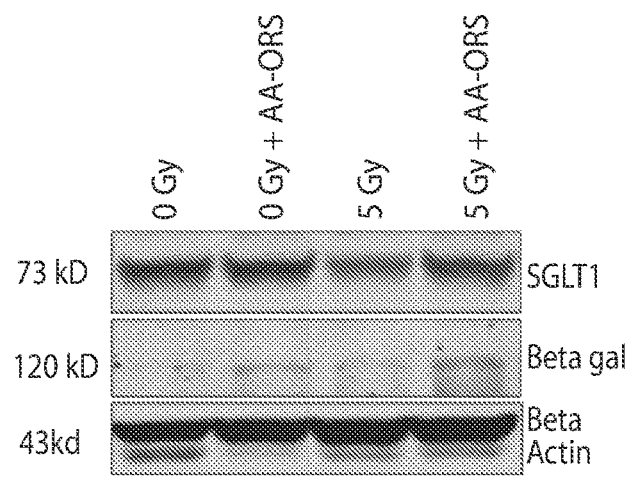
Figure 4C:
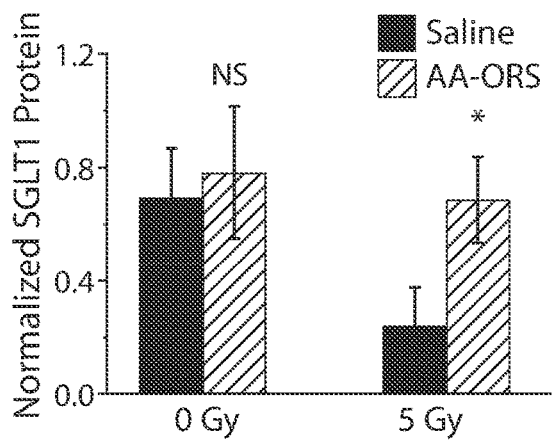
Figure 4D:
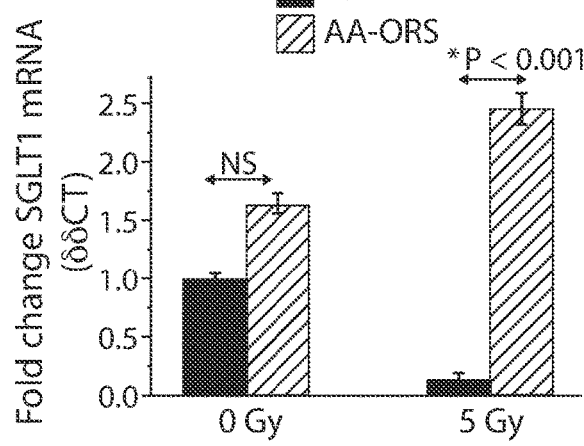

Ileal tissues from 5 Gy irradiated mice showed a significant reduction m glucose-stimulated sodium absorption (4.8±0.5 ueq·cm$^{2}$·h$^{-1}$ vs 0.3±0.1 ueq·cm$^{2}$·h$^{-1}$; p<0.001, n=6). Ileal tissues from AA-ORS-treated 5 Gy irradiated mice showed a significant increase in glucose-stimulated sodium absorption (0.3±0.1 ueq·cm$^{2}$·h$^{-1}$ vs 3.1±0.3 ueq·cm$^{2}$·h$^{-1}$; p<0.001, n=6), whereas 0 Gy irradiated mice did not exhibit this increase (4.8±0.5 ueq·cm$^{2}$·h-1 vs 5.9±0.7 ueq·cm$^{2}$·h$^{-1}$; p=ns, n=6) (FIG. 4A). AA-ORS treatment enhanced SGLT1 expression at the transcription and translational levels in 0 Gy and 5 Gy irradiated mice compared to saline-treated mice (FIGS. 4B-4D). These studies suggest that AA-ORS-induced increase in villi heights are functional, by showing that electrolyte absorptive capacity during inter-digestive phase (NHE3-mediated Na$^{+}$ absorption) and digestive phase (glucose-stimulated Na$^{+}$ absorption) are increased, both of which are a function of mature and differentiated villus epithelial cells.

Beta-galactosidase (lactose protein) levels were measured in isolated villus cells using Western blot analysis. Primarily, beta-galactosidase expression occurs in mature and differentiated villus epithelial cells. AA-ORS treatment increased beta-galactosidase protein levels in villus cells in 0 Gy and 5 Gy irradiated mice (FIG. 4B).

Example 5—Effect of AA-ORS on Intestinal Stem Cells and Proliferation Markers

At least three distinct crypt cell types are postulated to represent intestinal stem cells (ISC).[14] Each member of the population has distinct proliferation kinetics and sensitivities to radiation; therefore, each is thought to serve a unique function.[28] They are believed to dynamically switch from one type to the other in response to inhibitory and stimulatory signals caused by cytokines, hormones, or growth factors.[29] In contrast, slow-cycling intestinal epithelial stem cells (IESC) [label-retaining cells (LRC)] at the "+4 crypt position" contribute to homeostatic regenerative capacity, particularly during recovery from injury.[30] These LRC express various markers, such as BMI1, HOPX, LRIG1, and/or DCLK1, and can change to rapidly cycling IESCs in response to injury.[31] Lgr5 can mark both cells, whereas Bmil and HopX were reported to preferentially mark+4 cells.[14] Lgr5$^{+}$ ISC are necessary for intestinal regeneration following radiation injury.[32] Lgr5$^{-}$ and BMI1 are thought to be reserve cells that mount regenerative response following injury or radiation-induced damage. Studies have shown that the loss of Lgr5$^{+}$ cells is tolerated due to activation of the BM1-expressing stem cell pool.[14,32]

To determine if an increase in stem cell number and proliferation was responsible for the increased villus height observed with AA-ORS, the effect of AA-ORS on markers for stem cells and proliferation were studied.

Irradiation resulted in a significant decrease in Lgr5 protein levels (FIG. 5A). AA-ORS increased Lgr5 protein levels in 0 Gy and 5 Gy irradiated mice when compared to saline-treated control groups. However, intestinal tissues from 5 Gy irradiated mice showed no significant change in BMI1 protein levels when compared to 0 Gy. Similarly, AA-ORS did not bring about a change in BMI1 protein levels in 0 Gy and 5 Gy irradiated mice (FIG. 5A). Lgr5 transcript levels, but not BMI1 levels, significantly increased in AA-ORS-treated 0 Gy and 5 Gy mice (FIGS. 5C-5D).

It was found that 5 Gy resulted m a significant decrease in Lgr5 transcript and protein levels without much change in Bmil levels when compared to 0 Gy. A significant enhancement in the Lgr5 mRNA and protein levels without much change in Bmi1 with AA-ORS treatment was found, suggesting increased Lgr5-positive stem cells. These results also showed that the length covered by the migrating cells was significantly greater in intestinal sections from AA-ORS-treated irradiated mice when compared with saline-treated mice. Since transcription is halted in cells undergoing apoptosis, it is plausible that increased cell survival preferentially elevates short-lived transcripts, such as Lgr5, over the long-lived transcripts. BMI1 protein levels in intestinal tissues did not change in response to radiation or AA-ORS, thereby suggesting that the reserve populations of ISC are not affected at the radiation dose studied. Also, the increase in Lgr5 protein levels with AA-ORS supports these observations in the crypt count study that AA-ORS treatment following increasing doses of radiation, when fit in as a single-hit, multi-target model, leads to an increase in ISC number.

Western blot analysis of ERK1/2 and pERK1/2 were studied using the whole cell fraction to assess the effect of radiation and AA-ORS on proliferation. To determine the transcript levels of ERK and AKT, qPCR studies were undertaken in epithelial cells isolated from 0 Gy and 5 Gy irradiated tissues both in the absence and presence of treatment. ERK1/2 and AKT are phosphorylated when activated. Western blot analysis showed a significant difference in p-ERK protein levels at 0 Gy and 5 Gy (FIG. 5A). Total ERK protein levels were not significantly different in the AA-ORS-treated and saline-treated mice at 0 Gy or 5 Gy. Similarly, with ERK, 0 and 5 Gy mice treated with AA-ORS did not exhibit significant differences in AKT levels, whereas they did exhibit an increase in p-AKT protein levels when compared to the corresponding saline-treated irradiated groups. Intestinal tissues from 5 Gy mice showed a significant decrease in p-AKT when compared to 0 Gy mice.

Figure 5E:
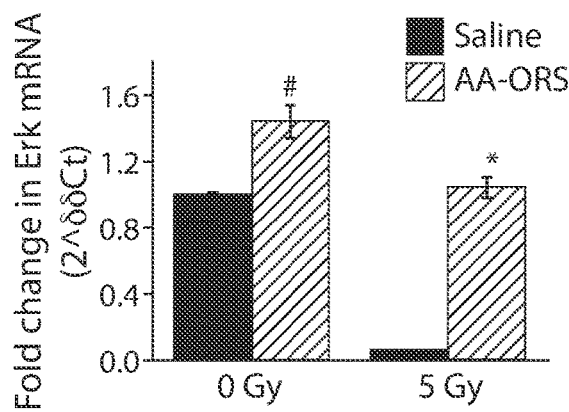
Figure 5F:
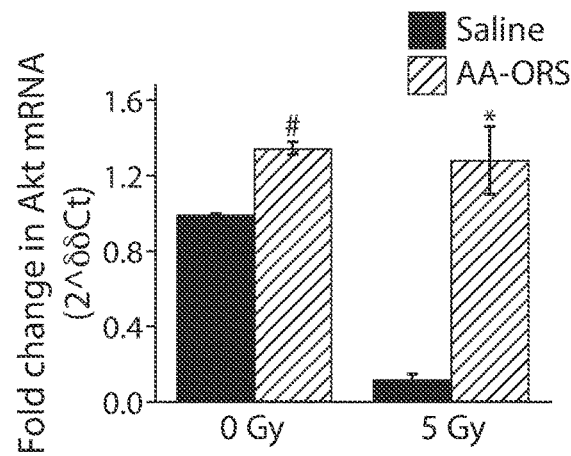

These studies suggest an increased phosphorylation level of the protein with AA-ORS treatment without a change in total protein expression. Since the effect of MAPK is dependent on it downstream effector the activating transcription factor 4 (Atf4), the Atf4 protein levels were measured using western blot analysis. 5 Gy irradiation reduced protein levels of Atf4, but AA-ORS treatment increased Atf4 protein levels in 0 Gy and 5 Gy irradiated mice. Studying ERK and AKT transcript levels using qPCRindicated that 5 Gy irradiation resulted in a significant decrease in mRNA levels when compared to 0 Gy. AA-ORS treatment resulted in a significant increase when compared to saline-treated mice at 0 Gy and 5 Gy (FIGS. 5E-5F). Early changes in normal cell proliferation within the intestinal tract serve as an indication of deviation from normal gastrointestinal function. Changes in the expression of proliferating cell nuclear antigen (PCNA), a 36 kD protein is recognized as one such marker for changes in the gut. AA-ORS increased PCNA protein levels in 0 Gy and 5 Gy irradiated mice (FIG. 5A).

The effect of AA-ORS on B-cell lymphoma-2 protein (Bcl-2), a downstream target for Erk1/2 was also studied. Bcl-2 prevents cell death rather than promoting cell proliferation by regulating the expression levels of the pro-apoptotic Bcl-2 associated X-protein (Bax) in the intrinsic caspase cascade. Bcl-2 levels increased with AA-ORS treatment in 0 Gy mice. Irradiation resulted in significant increase in Bcl-2 protein levels. Treatment using AA-ORS did not show further increase in Bcl2 protein levels in 5 Gy irradiated mice (FIG. 5B). Increased Bcl-2 protein levels with irradiation may suggest a protective mechanism to prevent apoptosis. However, western blot analysis using Bax specific antibodies did not show a significant difference in protein levels (FIG. 5B). The studies agree with previous observations that interventions targeting Bcl-2 not necessarily change protein levels of Bax4.

Since AA-ORS increased p-ERK, this study suggest that the amino acids help maintain the mitogenic stimulus until late G 1 for successful S-phase entry.[38]

This study showed that radiation increased caspase-3 and that AA-ORS treatment decreased cleaved caspase-3 in the villus epithelial cells of 0 Gy and 5 Gy mice. Increased pAKT in AA-ORS-treated mice suggests its action may be by activation of proliferation or inhibiting apoptosis (FIG. 5). Together with the effects seen on caspase-3, these results could explain the pro-survival effect and increased proliferation observed with AA-ORS treatment. However, further studies will be essential to characterize the mechanisms by which AA-ORS activates ERK1/2 and AKT or caspase-3.

Example 6—AA-ORS Decreased Cleaved Caspase-3 and Caspase-3 Transcript Levels

Figure 5G:
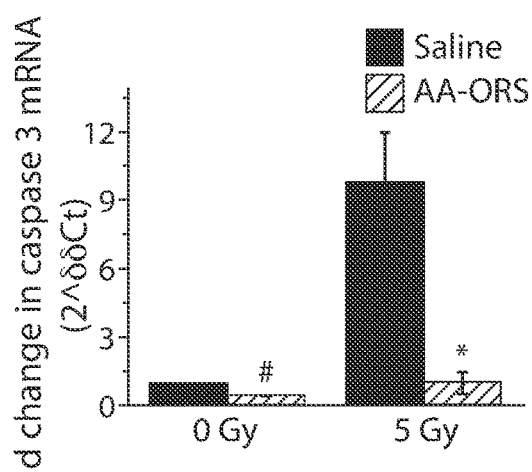
Figure 5H:
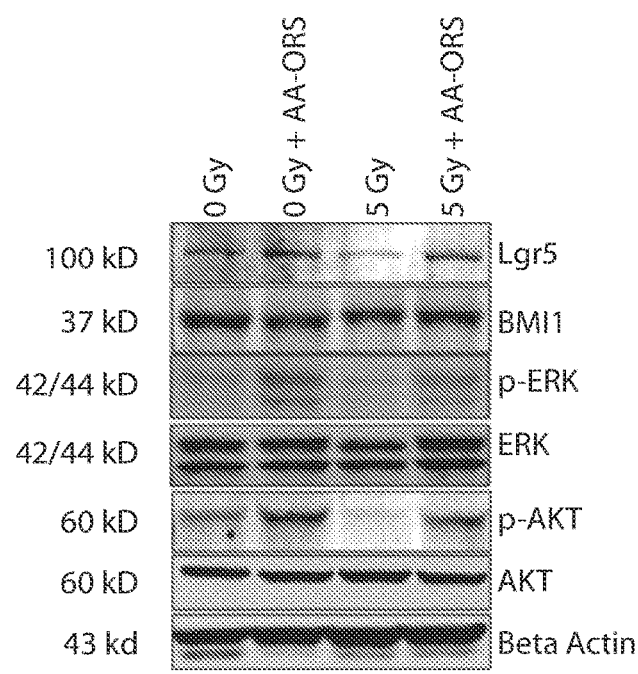
FIG. 5H shows Western blot analysis for Lgr5, BMI1, p-AKT, AKT, p-ERK, and ERK. Immunoblots were repeated at least four times, and q-PCRs were repeated at least 6 times. (5A) Western blot analysis for stem cell and proliferation markers (Lgr5, BMI1, p-AKT, AKT, p-ERK, ERK, and PCNA). The protein band of interest was normalized to the total amount of protein in each lane using Coomassie blue stain. (5B) Western blot analysis for apoptotic proteins (Bcl2, Bax, cleaved caspase-3, caspase-3 and p53). (5C) Lgr5 mRNA levels in mice treated with saline or AA-ORS and 0 Gy or 5 Gy irradiation. (5D) Changes in BMI1 mRNA levels in mice treated with saline or AA-ORS and 0 Gy or 5 Gy irradiation. (5E) Changes in ERK mRNA levels in mice treated with saline or AA-ORS and 0 Gy or 5 Gy irradiation. (5F) Changes in AKT mRNA levels in mice treated with saline or AA-ORS and 0 Gy or 5 Gy irradiation. (5G) mRNA expression for caspase-3. Values are means±SEM from n=6 different mice repeated in triplicate. #P<0.05 and *P<0.001 compared with saline control. (5H) Western blot analysis for Lgr5, BMI1, p-AKT, AKT, p-ERK, and ERK. The protein band of interest was normalized to the total amount of protein in each lane using Ponsceau S stain.

Activation of caspase-3 results in the formation of a 19 kD cleaved caspase-3. Cleaved caspase-3 increases with apoptosis. Western blot analysis showed no significant difference in total caspase-3 following irradiation and with treatment when compared to the control. Intestinal tissues from 5 Gy mice showed a significant increase in cleaved caspase-3 when compared to tissues from the 0 Gy mice. However, cleaved capase-3 decreased with AA-ORS when compared to the corresponding irradiation controls (FIG. 5B). Caspase 3 mRNA levels measured using qPCR showed a significant increase in caspase 3 transcript levels following 5 Gy irradiation when compared to 0 Gy. Treatment using AA-ORS resulted in a significant decrease in caspase 3 transcript levels in intestinal tissues from 0 Gy and 5 Gy irradiated mice (FIG. 5G).

Together with Lgr5, p-ERK, and p-AKT, the changes in cleaved caspase-3 suggest that AA-ORS increased villus height in intestinal tissues from nonirradiated and irradiated mice not only through proliferation but also through decreased apoptosis and increased cell survival.

To assess if the villous epithelial cells resulting from increased proliferation and/or decreased apoptosis are mature, differentiated and are functionally active, the sodium absorptive capacity and glucose-stimulated sodium absorption was measured. Both NHE3, the predominant transporter of sodium absorption in small intestine and SGLT1, the transporter for sodium-coupled sodium absorption occurs only in mature and differentiated villous cells and were shown to have increased function (FIGS. 3A-3F and 4A-4D), mRNA and protein levels. These studies therefore suggested that the treatment with AA-ORS following radiation increased electrolyte and glucose absorption (FIG. 5A-5G).

Example 7—Western Blot Analysis of Total p53 p53 is a tumor suppressor protein and its activity stops the formation of tumors. Mutations in p53 tumor-suppressor gene are the most frequently observed genetic lesions in human cancers. Mice homozygous for the null allele appear normal but are prone to the spontaneous development of a variety of tumors. p53 has been shown to play an important role in the response of irradiation. The level of p53 accumulation in response to irradiation is primarily results from the intensity of DNA damage. It has been demonstrated that loss of stem cells plays an important role in radiation-induced acute intestinal injury and lethality, and is regulated by the p53 pathway and its transcriptional targets PUMA and p21. PUMA-dependent apoptosis quickly reduce ISCs and its progenitors in hours following high dose radiation, and deficiency of PUMA leads to improved animal survival and crypt regeneration by enhancing p21-dependent DNA repair and is crucial for radiation-induced intestinal damage.

Western blot analysis showed no significant difference in the p53 (a tumor suppressor protein) level in intestinal tissues from 0 Gy and 5 Gy mice. AA-ORS showed a small but consistent increase in p53 protein levels (FIG. 5B).

These studies suggest that the proliferative effect associated with AA-ORS may not be associated with tumorigenesis.

Example 8—Immunohistochemistry

Figure 6A:
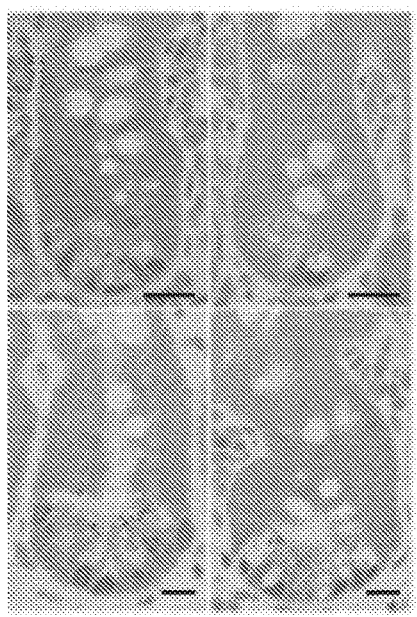
FIGS. 6A-6G show representative microphotographs of the distribution of $Lgr5^+$, $Ki\text{-}67^+$ and $PCNA^+$ cells within ileal mucosa of 0 Gy (left) and 5 Gy (right) after treatment with saline (top) or AA-ORS (bottom). (6A) lmmunostaining for Lgr5: $Lgr5^+$ cells were seen in the lower ⅓rd of the crypt. Mice irradiated with 5 Gy resulted in a significant decline of $Lgr5^+$ stem cells in ileal crypts, and AA-ORS increased $Lgr5^+$ stem cells. Scale bars represent 25 (6B) Mean number of $Lgr5^+$ cells expressed in crypt. Error bars indicate S.E.M. (6C) Immunostaining for Ki-67: The number of Ki-67-expressing cells, a proliferation marker, showed no significant difference in 0 Gy radiated mice treated with AA-ORS when compared to saline-treated groups. 5 Gy irradiated mice showed significant increase in $Ki\text{-}67^+$ cells with AA-ORS treatment. Scale bars represent 100 (6D) Mean number of Ki-67 expressing cells in crypt and/or villus cells. Error bars indicate S.E.M. (6E) Immunostaining for PCNA: The number and distribution of $PCNA^+$ cells. $PCNA^+$ cells were reduced in mice after 5 Gy radiation, but increased with AA-ORS treatment. Scale bars represent 100 (6F) Mean number of PCNA expressing cells in crypt and/or villus cells. Error bars indicate S.E.M. (6G) Protein levels and mRNA expression of cleaved caspase 3, total caspase 3 and p53 in villous epithelial cells from mice treated with normal saline and AA-ORS following 0 and 5 Gy irradiated mice. Immunoblots were repeated at least four times and q-PCR were repeated at least 6 times. Western blot analysis for cleaved caspase 3, total caspase 3, and p53. The protein band of interest was normalized to the total amount of protein in each lane using Ponsceau S stain and beta actin.
Figure 6B:
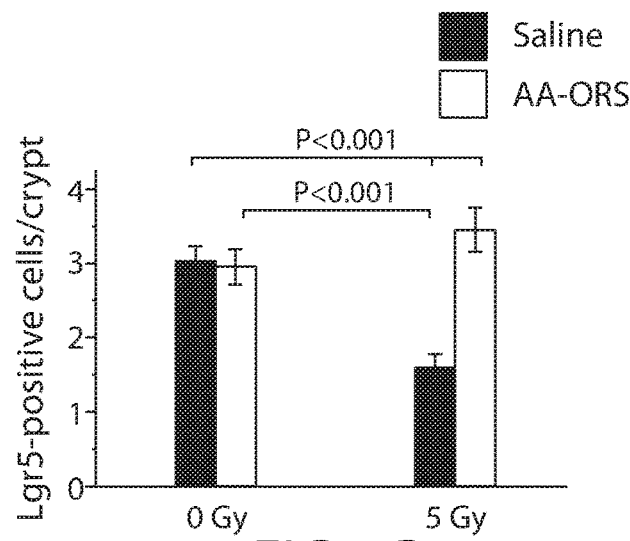

Avidin-biotin detection method using a polyclonal antibody against Lgr5+, intestinal stem cells showed a decrease in Lgr5+ cells with radiation (3.0±0.2 vs 1.6±0.2; P<0.001, n=50 crypts). Treatment using AA-ORS did not show a significant difference in Lgr5+ in 0 Gy irradiated mice. However, in 5 Gy irradiated mice AA-ORS increased Lgr5+ cells (1.6±0.2 vs 3.4±0.3; P<0.001, n=50 crypts) (FIGS. 6A-6B).

Figure 6C:
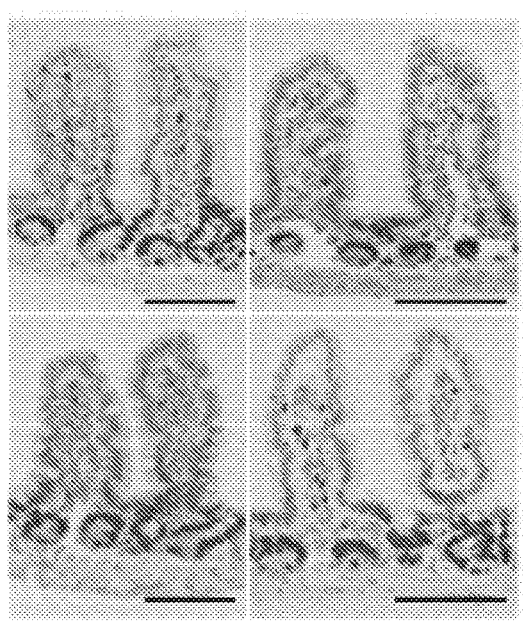
Figure 6D:
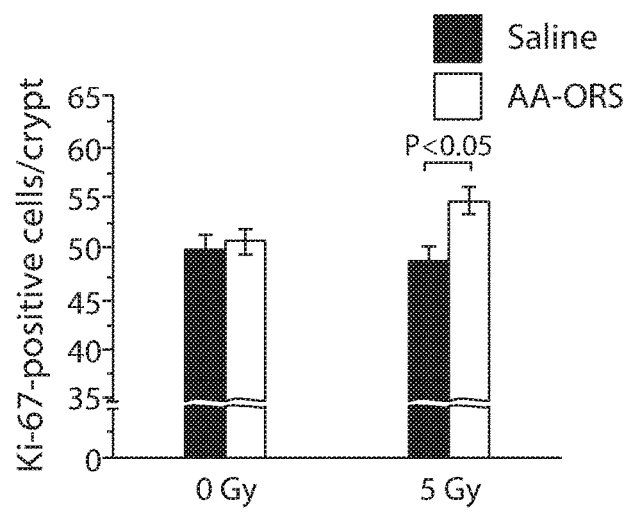

The Ki-67 is a nuclear protein, cellular marker for proliferation and is associated with ribosomal RNA transcription. The Ki-67 is also present in the cell during all active phases of cells cycle ($G_1$, S, $G_2$, and mitosis), but absent from resting cells ($G_0$). Ileal sections showed Ki-67 expression along the crypt except its lower pole and the expression extended into the lower ⅓rd of the villi. There was no significant difference in Ki-67 expression with radiation, however treatment using AA-ORS resulted in significant increase in Ki-67 expressed cells (50.7±1.3 vs 54.6±1.4; P<0.05, n=50 crypts) (FIGS. 6C-6D).

Figure 6E:
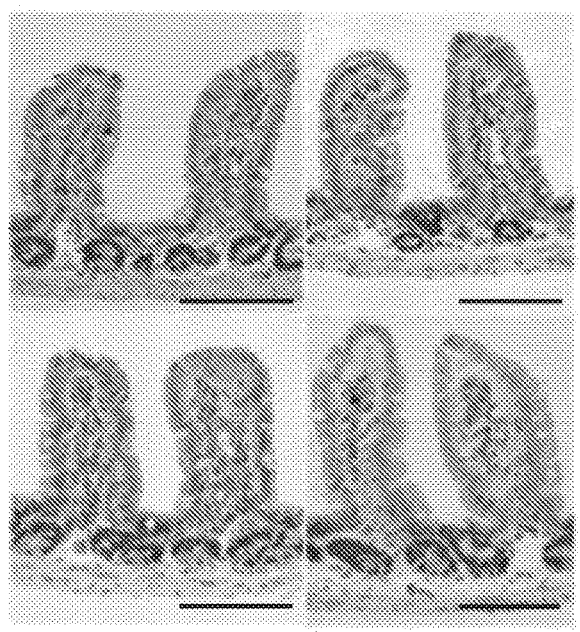
Figure 6F:
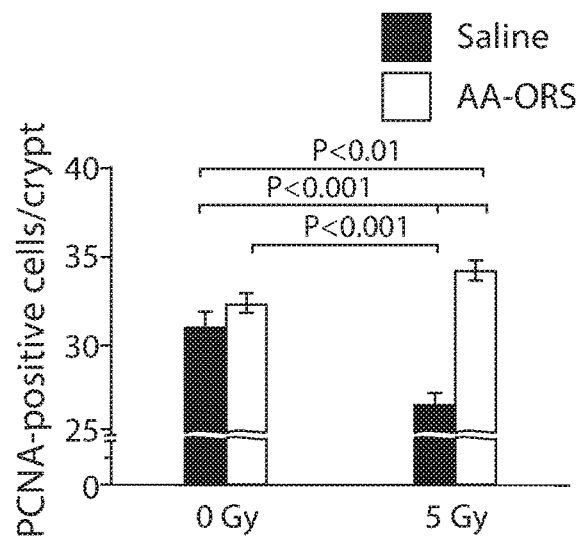
Figure 6G:
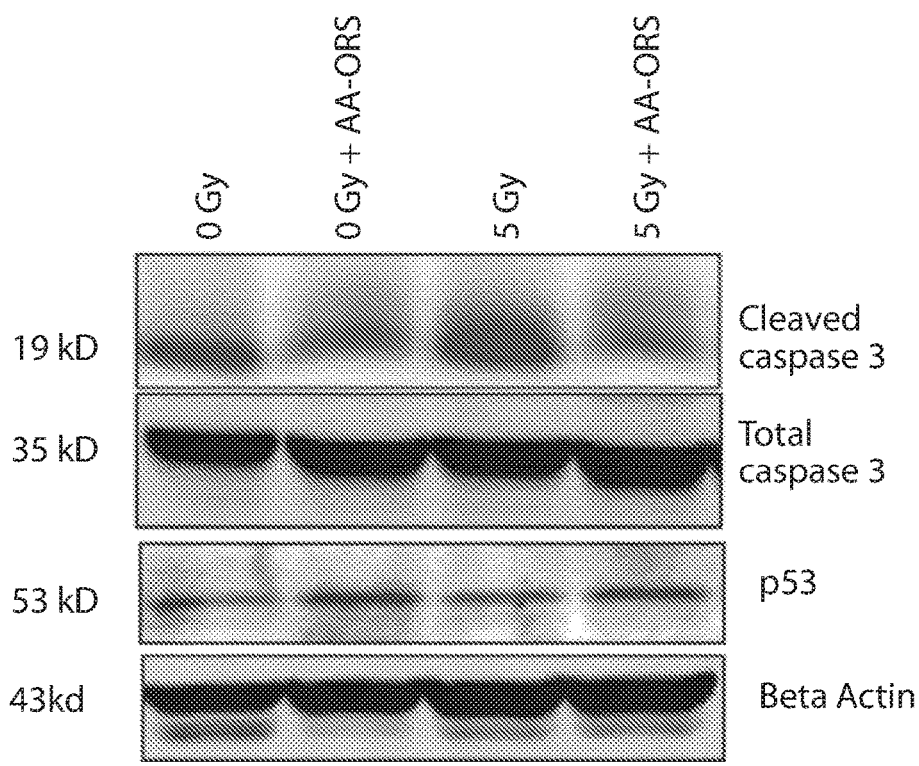

Immunostaining for PCNA in ileal sections showed its expression along the crypt except its lower pole. Irradiation resulted in a significant decrease in PCNA expression in both the crypt and in the lower regions of the villi (31.1±0.8 vs 26.6±0.6; P<0.001, n=50 crypts). Treatment using AA-ORS showed significant increase in 5 Gy mice (26.6±0.6 vs 34.2±0.5; P<0.001, n=50 crypts) and not in 0 Gy irradiated mice (FIGS. 6E-6F).

Western blot analysis showed that cell homogenates from small intestinal mice irradiated at 5 Gy showed significant increase when compared to 0 Gy. Mice treated with AA-ORS increased Ki67 protein levels in 0 Gy, but not did not further increase in 5 Gy. These studies suggest that AA-ORS-induced epithelial proliferation is mediated via Ki67 at 0 Gy not at 5 Gy.

This study signifies how a systematic selection of certain nutrients based on their beneficial effect on GI function helped to improve intestinal stem cell proliferation, maturation, and differentiation, leading to functionally active long villus epithelial cells whose function and height were initially compromised by irradiation (FIG. 7).

Example 9—AA-ORS Improved Gastrointestinal Function in Mice

Using electrophysiological techniques, it was shown that radiation-induced Cl-secretion can occur at radiation doses that are too low to cause obvious histopathological changes.[55] Radiation-induced enteric dysfunction was characterized by: (1) increased Cl-secretion that was responsible for increased fluid secretion; (2) decreased absorption of Na+, which led to decreased fluid absorption; and (3) increased paracellular permeability that resulted in increased translocation of luminal antigenic substances into the systemic compartment, generating a local and systemic immune response. Increased permeation of luminal contents into the systemic compartment increased plasma endotoxin and proinflammatory cytokines (e.g., IL1β).[51]

As outlined in a previous study, an amino acid-based oral rehydration solution (AA-ORS) was previously developed.[51] Particular amino acids were chosen based on the findings in intestinal tissues from irradiated mice that the selected amino acids: (1) increased Na+ absorption via amino acids coupled Na+ absorption; (2) did not stimulate Cl- secretion and, therefore, fluid secretion; and (3) decreased paracellular permeability or tightening of the mucosal barrier. Treatment with AA-ORS for a period of 14 days improved electrolyte absorption, decreased paracellular permeability as well as plasma endotoxin and proinflammatory cytokine levels, better preserved body weight, and improved survival in mice exposed to an otherwise lethal dose of total-body irradiation (8.5 Gy TBI)[51]. The subsequent studies showed that these improvements occurred as early as 7 days after AA-ORS treatment; however, the exact mechanisms for these effects were unknown.

In summary, AA-ORS comprising a select set of amino acids was identified as an intestinal radio-mitigator in mice by selectively enhancing stem cell markers such as Lgr5 & BMI1 and by blocking caspase-3 mediated apoptosis in intestinal stem and progenitor cells. This study therefore signifies the effect of simple amino acids on intestinal stem cell proliferation, maturation, and differentiation leading to functionally active long villous epithelial cells whose function and height was compromised by irradiation.

The examples and embodiments described herein are for illustrative purposes only and various modifications or changes in light thereof will be suggested to persons skilled in the art and are included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. Adams, P. D. et al. Identification of a cyclin-cdk2 recognition motif present in substrates and p21-like cyclin-dependent kinase inhibitors. *Mol Cell Biol* 16, 6623-6633 (1996).
2. Barker, N., van Oudenaarden, A. & Clevers, H. Identifying the stem cell of the intestinal crypt: strategies and pitfalls. *Cell Stem Cell* 11, 452-460, doi:10.1016/j.stem.2012.09.009 (2012).
3. Bullwinkel J, Baron-Luhr B, Ludemann A, et al. Ki-67 protein is associated with ribosomal RNA transcription in quiescent and proliferating cells. J Cell Physiol 2006; 206:624-35.
4. Cheng, H. & Leblond, C. P. Origin, differentiation and renewal of the four main epithelial cell types in the mouse small intestine. V. Unitarian Theory of the origin of the four epithelial cell types. *Am J Anat* 141, 537-561 (1974).
5. Citrin, D. et al. Radioprotectors and mitigators of radiation-induced normal tissue injury.
6. Crosnier, C., Stamataki, D. & Lewis, J. Organizing cell renewal in the intestine: stem cells, signals and combinatorial control. *Nat Rev Genet* 7, 349-359, doi:10.1038/nrg1840 (2006).

7. Cryns, V. & Yuan, J. Proteases to die for. *Genes Dev* 12, 1551-1570 (1998).
8. Danial, N. N. & Korsmeyer, S. J. Cell death: critical control points. *Cell* 116, 205-219 (2004).
9. Datta, S. R., Brunet, A. & Greenberg, M. E. Cellular survival: a play in three Akts. *Genes Dev* 13, 2905-2927 (1999).
10. Davis, N. M. et al. Deregulation of the EGFR/PBK/PTEN/Akt/mTORC1 pathway in breast cancer: possibilities for therapeutic intervention. *Oncotarget* 5, 4603-4650, doi: 10.18632/oncotarget.2209 (2014).
11. Donehower, L. A. et al. Mice deficient for p53 are developmentally normal but susceptible to spontaneous tumours. *Nature* 356, 215-221, doi:10.1038/356215a0 (1992).
12. Fei, P. & El-Deiry, W. S. P53 and radiation responses. *Oncogene* 22, 5774-5783, doi: 10.1038/sj.onc.1206677 (2003).
13. Fukuda, M., Gotoh, Y. & Nishida, E. Interaction of MAP kinase with MAP kinase: its possible role in the control of nucleocytoplasmic transport of MAP kinase. *EMBO J* 16, 1901-1908, doi:10.1093/emboj/16.8.1901 (1997).
14. Gopal, R. et al. The relationship between local dose and loss of function for irradiated lung. *Int J Radiat Oneal Biol Phys* 56, 106-113 (2003).
15. Greenberger, J. S. Radioprotection. *In Vivo* 23, 323-336 (2009).
16. Hahn, S. M. et al. Identification of nitroxide radioprotectors. *Radiat Res* 132, 87-93 (1992).
17. Hall, P. A. & Lane, D. P. Tumor suppressors: a developing role for p53? *Curr Biol* 7, R1 44-14 7 (1997).
18. Hauer-Jensen, M., Wang, J. & Denham, J. W. Bowel injury: current and evolving management strategies. *Semin Radiat Oncol* 13, 357-371 (2003). *Health Phys* 106, 734-744, doi:10.1097/HP.0000000000000117 (2014).
19. Houghton, J. et al. Gastric cancer originating from bone marrow-derived cells. *Science* 306, 1568-1571, doi:10.1126/science.1099513 (2004).
20. Kahan, C., Seuwen, K., Meloche, S. & Pouyssegur, J. Coordinate, biphasic activation of p44 mitogen-activated protein kinase and S6 kinase by growth factors in hamster fibroblasts. Evidence for thrombin-induced signals different from phosphoinositide turnover and adenylylcyclase inhibition. *J Biol Chem* 267, 13369-13375 (1992).
21. Kandel, E. S. et al. Activation of Akt/protein kinase B overcomes a 0(2)/m cell cycle checkpoint induced by DNA damage. *Mol Cell Biol* 22, 7831-7841 (2002).
22. Karam, S. M. Lineage commitment and maturation of epithelial cells in the gut. *Front Biosci* 4, D286-298 (1999).
23. Komarova, E. A. et al. Dual effect of p53 on radiation sensitivity in vivo: p53 promotes hematopoietic injury, but protects from gastro-intestinal syndrome in mice. *Oncogene* 23, 3265-3271, doi: 10.1038/sj.onc.1207494 (2004).
24. Leibowitz, B. J. et al. Uncoupling p53 functions in radiation-induced intestinal damage via PUMA and p21. *Mol Cancer Res* 9, 616-625, doi:10.1158/1541-7786.MCR-11-0052 (2011).
25. Li L, Clevers H. Coexistence of quiescent and active adult stem cells in mammals. Science 2010; 327:542-5.
26. Li, X. M., Hu, Z., Jorgenson, M. L., Wingard, J. R. & Slayton, W. B. Bone marrow sinusoidal endothelial cells undergo nonapoptotic cell death and are replaced by proliferating sinusoidal cells in situ to maintain the vascular niche following lethal irradiation. *Exp Hematol* 36, 1143-1156, doi:10.1016/j.exphem.2008.06.009 (2008).
27. Lu, Z. & Xu, S. ERK1/2 MAP kinases in cell survival and apoptosis. *IUBMB Life* 58, 621-631, doi: 10.1080/15216540600957438 (2006).
28. Marks, L. B. Dosimetric predictors of radiation-induced lung injury. *Int J Radiat Oneal Biol Phys* 54, 313-316 (2002).
29. Meloche, S. Cell cycle reentry of mammalian fibroblasts is accompanied by the sustained activation of p44mapk and p42mapk isoforms in the G 1 phase and their inactivation at the Gl/S transition. *J Cell Physiol* 163, 577-588, doi:10.1002/jcp.1041630319 (1995).
30. Metcalfe, C., Kljavin, N. M., Ybarra, R. & de Sauvage, F. J. Lgr5+ stem cells are indispensable for radiation-induced intestinal regeneration. *Cell Stem Cell* 14, 149-159, doi:10.1016/j.stem.2013.11.008 (2014).
31. Nair, C. K., Parida, D. K. & Nomura, T. Radioprotectors in radiotherapy. *J Radiat Res* 42, 21-37 (2001).
32. Niu, Y. et al. Intraesophageal MnSOD-plasmid liposome enhances engraftment and selfrenewal of bone marrow derived progenitors of esophageal squamous epithelium. *Gene Ther* 15, 347-356, doi: 10.1038/sj.gt.3303089 (2008). *Oncologist* 15, 360-371, doi: 10.1634/theoncologist.2009-S 104(2010).
33. Pageot, L. P. et al. Human cell models to study small intestinal functions: recapitulation of the crypt-villus axis. *Microsc Res Tech* 49, 394-406, doi:10.1002/(SICI)1097-0029(20000515)49:4<394::AID-JEMT8>3.0.00;2-K (2000).
34. Potten, C. S. A comprehensive study of the radiobiological response of the murine (BDF1) small intestine. *Int J Radiat Biol* 58, 925-973, doi:7AQN1HHQNKSERATM [pii] (1990).
35. Potten, C. S. Radiation, the ideal cytotoxic agent for studying the cell biology of tissues such as the small intestine. *Radiat Res* 161, 123-136 (2004).
36. Potten, C. S., Booth, C. & Pritchard, D. M. The intestinal epithelial stem cell: the mucosal governor. *Int Exp Pathol* 78, 219-243 (1997).
37. Pritchard, D. M., Potten, C. S., Korsmeyer, S. J, Roberts, S. & Hickman, J. A. amageinduced apoptosis in intestinal epithelia from bc1-2-null and bax-null mice: investigations of the mechanistic determinants of epithelial apoptosis in vivo. *Oncogene* 18, 7287-7293, doi: 10.1038/sj.onc.1203150 (1999).
38. Qiu, W. et al. PUMA regulates intestinal progenitor cell radiosensitivity and gastrointestinal syndrome. *Cell Stem Cell* 2, 576-583, doi:10.1016/j.stem.2008.03.009 (2008).
39. Ramaswamy, S. et al. Regulation of G 1 progression by the PTEN tumor suppressor protein is linked to inhibition of the phosphatidylinositol 3-kinase/Akt pathway. *Proc Natl Acad Sci USA* 96, 2110-2115 (1999).
40. Reszka, A. A., Seger, R., Diltz, C. D., Krebs, E. G. & Fischer, E. H. Association of mitogen-activated protein kinase with the microtubule cytoskeleton. *Proc Natl Acad Sci USA* 92, 8881-8885 (1995).
41. Rubin, P. & Casarett, G. W. Clinical radiation pathology as applied to curative radiotherapy. *Cancer* 22, 767-778 (1968).
42. Sarbassov, D. D., Guertin, D. A., Ali, S. M. & Sabatini, D. M. Phosphorylation and regulation of Akt/PKB by the rictor-mTOR complex. *Science* 307, 1098-1101, doi: 10.1126/science.1106148 (2005). *Science* 327, 542-545, doi:10.1126/science.1180794 (2010).

43. Shivdasani, R. A. Radiation redux: reserve intestinal stem cells miss the call to duty. *Cell Stem Cell* 14, 135-136, doi:10.1016/j.stem.2014.01.015 (2014).
44. Stephens, L. et al. Protein kinase B kinases that mediate phosphatidylinositol 3,4,5-trisphosphate-dependent activation of protein kinase B. *Science* 279, 710-714 (1998).
45. Takeda, N. et al. Interconversion between intestinal stem cell populations m distinct niches. *Science* 334, 1420-1424, doi:10.1126/science.1213214 (2011).
46. Thornberry, N. A. & Lazebnik, Y. Caspases: enemies within. *Science* 281, 1312-1316 (1998).
47. Tucker, S. L., Withers, H. R., Mason, K. A. & Thames, H. D., Jr. A dose-surviving fraction curve for mouse colonic mucosa. *Eur J Cancer Clin Oncol* 19, 433-437 (1983).
48. Vidyasagar, S., Barmeyer, C., Geibel, J., Binder, H. J. & Rajendran, V. M. Role of shortchain fatty acids in colonic $HCO_3-$ secretion. *Am J Physiol Gastrointest Liver Physiol* 288, G 1217-1226 (2005).
49. Yamamoto, T. et al. Continuous ERK activation downregulates antiproliferative genes throughout G 1 phase to allow cell-cycle progression. *Curr Biol* 16, 1171-1182, doi: 10.1016/j.cub.2006.04.044 (2006).
50. Yan, K. S. et al. The intestinal stem cell markers Bmi 1 and Lgr5 identify two functionally distinct populations. *Proc Natl Acad Sci USA* 109, 466-471, doi: 10.1073/pnas.1118857109(2012).
51. Yin L, Vijaygopal P, Menon R, et al. An amino acid mixture mitigates radiation-induced gastrointestinal toxicity. Health Phys 2014; 106:734-44.
52. Yin, L. et al. Glucose stimulates calcium-activated chloride secretion in small intestinal cells. *Am J Physiol Cell Physiol* 306, C687-696, doi:10.1152/ajpce11.00174.2013 (2014).
53. Yu, J. Intestinal stem cell injury and protection during cancer therapy. *Transl Cancer Res* 2, 384-396 (2013).
54. Zhang, H., Ameen, N., Melvin, J. E. & Vidyasagar, S. Acute inflammation alters bicarbonate transport m mouse ileum. *J Physiol* 581, 1221-1233, doi:10.1113/jphysiol.2007.129262 (2007).
55. Zhang, K. et al. Radiation decreases murine small intestinal $HCO_3-$ secretion. *Int J Radiat Biol* 87, 878-888, doi: 10.3109/09553002.2011.583314 (2011).

What is claimed is:

1. A method for treating asthma in a subject in need thereof, the method comprising administering to the subject a formulation comprising a therapeutically effective combination of free amino acids,
    wherein the therapeutically effective combination of free amino acids consists of:
        a therapeutically effective amount of free amino acids of threonine, valine, tyrosine, aspartic acid, and serine; and
    wherein the therapeutically effective combination of free amino acids is sufficient to reduce symptoms associated with asthma in the subject.

2. The method of claim 1, wherein the therapeutically effective amount of threonine is a concentration ranging from 0.4 grams/liter to 1.5 grams/liter or 0.7 grams/liter to 1.3 grams/liter;
    the therapeutically effective amount of valine is a concentration ranging from 0.7 grams/liter to 1.7 grams/liter or 0.9 grams/liter to 1.5 grams/liter;
    the therapeutically effective amount of tyrosine is a concentration ranging from 0.05 grams/liter to 0.4 grams/liter;
    the therapeutically effective amount of aspartic acid is a concentration ranging from 0.4 grams/liter to 3.6 grams/liter; or
    the therapeutically effective amount of serine is a concentration ranging from 0.6 grams/liter to 1.6 grams/liter or 0.8 grams/liter to 1.4 grams/liter; or
    any combination thereof.

3. The method of claim 1, wherein the therapeutically effective amount of threonine is a concentration ranging from 0.9 grams/liter to 1.1 grams/liter;
    the therapeutically effective amount of valine is a concentration ranging from 1.1 grams/liter to 1.3 grams/liter;
    the therapeutically effective amount of tyrosine is a concentration ranging from 0.1 grams/liter to 0.3 grams/liter;
    the therapeutically effective amount of aspartic acid is a concentration ranging from 0.4 grams/liter to 3.6 grams/liter; or
    the therapeutically effective amount of serine is a concentration ranging from 1.0 to about 1.2 grams/liter; or
    any combination thereof.

4. The method of claim 1, wherein the therapeutically effective amount of threonine is 1.0 g/l;
    the therapeutically effective amount of valine is 1.2 g/l; and
    the therapeutically effective amount of tyrosine is 0.2 g/l.

5. The method of claim 1, wherein
    the therapeutically effective amount of threonine is 8 mM,
    the therapeutically effective amount of valine is 10 mM,
    the therapeutically effective amount of tyrosine is 1.2 mM,
    the therapeutically effective amount of aspartic acid is 8 mM, and
    the therapeutically effective amount of serine is 10 mM.

6. The method of claim 1, wherein at least one of the free amino acids or each of the free amino acids is an L-form.

7. The method of claim 1, wherein the formulation further comprises a pharmaceutically acceptable carrier, buffer, adjuvant, or excipient.

8. The method of claim 1, wherein the formulation does not include, or comprises only negligible amounts of electrolytes.

9. The method of claim 1, wherein the subject is a human.

10. The method of claim 1, wherein the formulation is administered to the subject via oral or pulmonary administration.

11. A method for treating asthma in a subject in need thereof, the method comprising administering to the subject a formulation comprising a therapeutically effective combination of free amino acids,
    wherein the therapeutically effective combination of free amino acids consists of:
        a therapeutically effective amount of free amino acids of threonine, valine, tyrosine, serine, and tryptophan; and
    wherein the therapeutically effective combination of free amino acids is sufficient to reduce symptoms associated with asthma in the subject.

12. The method of claim 11, wherein the therapeutically effective combination of free amino acids is administered via inhalation.

13. The method of claim 11, wherein the therapeutically effective amount of threonine is a concentration ranging from 0.4 grams/liter to 1.5 grams/liter or 0.7 grams/liter to 1.3 grams/liter;

the therapeutically effective amount of valine is a concentration ranging from 0.7 grams/liter to 1.7 grams/liter or 0.9 grams/liter to 1.5 grams/liter;

the therapeutically effective amount of tyrosine is a concentration ranging from 0.05 grams/liter to 0.4 grams/liter;

the therapeutically effective amount of tryptophan is a concentration ranging from 1.1 grams/liter to 2.1 grams/liter or 1.3 grams/liter to 1.9 grams/liter; or the therapeutically effective amount of serine is a concentration ranging from 0.6 grams/liter to 1.6 grams/liter or 0.8 grams/liter to 1.4 grams/liter;

or any combination thereof.

14. The method of claim 11, wherein the therapeutically effective amount of threonine is a concentration ranging from 0.9 grams/liter to 1.1 grams/liter;

the therapeutically effective amount of valine is a concentration ranging from 1.1 grams/liter to 1.3 grams/liter;

the therapeutically effective amount of tyrosine is a concentration ranging from 0.1 grams/liter to 0.3 grams/liter;

the therapeutically effective amount of tryptophan is a concentration ranging from 1.5 grams/liter to 1.7 grams/liter; or the therapeutically effective amount of serine is a concentration ranging from 1.0 to about 1.2 grams/liter; or any combination thereof.

15. The method of claim 11, wherein the therapeutically effective amount of threonine is 1.0 g/l; the therapeutically effective amount of valine is 1.2 g/l;

the therapeutically effective amount of tyrosine is 0.2 g/l; and the therapeutically effective amount of tryptophan is 1.6 g/l.

16. The method of claim 11, wherein the therapeutically effective amount of threonine is 8 mM, the therapeutically effective amount of valine is 10 mM, the therapeutically effective amount of tyrosine is 1.2 mM, the therapeutically effective amount of tryptophan is 8 mM, and the therapeutically effective amount of serine is 10 mM.

17. The method of claim 11, wherein at least one of the free amino acids or each of the free amino acids is an L-form.

18. The method of claim 11, wherein the formulation further comprises a pharmaceutically acceptable carrier, buffer, adjuvant, or excipient.

19. The method of claim 11, wherein the formulation does not include, or comprises only negligible amounts of electrolytes.

20. The method of claim 11, wherein the subject is a human.

21. The method of claim 11, wherein the formulation is administered to the subject via oral or pulmonary administration.

* * * * *